(12) United States Patent
Minea et al.

(10) Patent No.: US 8,338,365 B2
(45) Date of Patent: Dec. 25, 2012

(54) INHIBITING INTEGRIN RECEPTOR BINDING WITH NON-NATIVE MONOMERIC DISINTEGRIN OR MONOMERIC DISINTEGRIN DOMAINS

(75) Inventors: Radu O. Minea, Arcadia, CA (US); Francis S. Markland, Jr., Manhattan Beach, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/367,267

(22) Filed: Feb. 6, 2012

(65) Prior Publication Data
US 2012/0301453 A1 Nov. 29, 2012

Related U.S. Application Data

(60) Division of application No. 12/831,226, filed on Jul. 6, 2010, now Pat. No. 8,110,542, which is a continuation of application No. 11/351,311, filed on Feb. 9, 2006, now Pat. No. 7,754,850.

(60) Provisional application No. 60/652,529, filed on Feb. 11, 2005.

(51) Int. Cl.
| A61K 38/00 | (2006.01) |
| A61K 38/36 | (2006.01) |
| A61P 35/00 | (2006.01) |
| A61P 7/02 | (2006.01) |
| A61P 35/04 | (2006.01) |
| C07K 14/705 | (2006.01) |

(52) U.S. Cl. ...... 514/1.1; 514/13.3; 514/13.7; 514/19.1; 514/19.3; 514/19.8

(58) Field of Classification Search ............... None
See application file for complete search history.

(56) References Cited

U.S. PATENT DOCUMENTS

| 4,610,879 | A | 9/1986 | Markland et al. |
| 5,731,288 | A | 3/1998 | Markland et al. |
| 5,814,609 | A | 9/1998 | Markland et al. |
| 6,387,664 | B1 | 5/2002 | Ikemoto |
| 6,537,988 | B2 | 3/2003 | Lee |
| 6,710,030 | B1 | 3/2004 | Markland et al. |
| 7,220,724 | B2 | 5/2007 | Markland et al. |
| 2003/0186334 | A1 | 10/2003 | Marcinkiewicz |
| 2003/0186884 | A1 | 10/2003 | Markland et al. |
| 2004/0029781 | A1 | 2/2004 | Hernan et al. |
| 2004/0043387 | A1 | 3/2004 | Liu et al. |
| 2004/0052785 | A1 | 3/2004 | Goodman et al. |
| 2007/0093878 | A1 | 4/2007 | Edge et al. |
| 2007/0123458 | A1 | 5/2007 | Markland et al. |
| 2008/0306611 | A1 | 12/2008 | Rowley et al. |
| 2008/0317763 | A1 | 12/2008 | Lackmann et al. |

FOREIGN PATENT DOCUMENTS

| DE | 19713213 | 10/1998 |
| JP | 2000-245467 | 9/2000 |
| JP | 2004-217535 | 8/2004 |
| WO | WO-00/18421 | 4/2000 |
| WO | WO-01/041791 | 6/2001 |
| WO | WO-2010/093468 | 8/2010 |

OTHER PUBLICATIONS

Aslund et al., "The Thioredoxin Superfamily: Redundancy, Specificity and Gray-Area Genomics, " Journal of Bacteriology, 181(5):1375-1379 (1999).
Bader et al., "Disulfide Bonds are Generated by Quinone Reduction," The Journal of Biological Chemistry, 275(34):26082-26088 (2000).
Bader et al., "Oxidative Protein Folding is Driven by the Electron Transport System," Cell, 98:217-227 (1999).
Bader et al., "Reconstitution of a Protein Disulfide Catalytic System, The Journal of Biological Chemistry," 273(17):10302-10307 (1998).
Bader et al., "Turning a Disulfide Isomerase into an Oxidase: DsbC Mutants that Imitate DsbA," The EMBO Journal, 20(7):1555-1562 (2001).
Baneyx, "Recombinant Protein Expression in *Escherichia coli*," Current Opinion in Biotechnology, 10:411-421 (1999).
Bardwell et al., "A Pathway for Disulfide Bond Formation in Vivo," PNAS, 90:1038-1042 (1993).
Bardwell et al., "Identification of a Protein Required for Disulfide Bond Formation in Vivo," Cell, 67:581589 (1991).
Becker et al., "Expression, Secretion and Folding of Human Growth Hormone in *Escherichia coli*," FEBS, 204(1):145-150 (1986).
Bessette et al., "Effect of Sequences of the Active-Site Dipeptides of DsbA and DsbC on in Vivo Folding of Multidisulfide Proteins in *Escherichia coli*," Journal of Bacteriology, 183(3):980-988 (2001).
Bessette et al., "Efficient Folding of Proteins with Multiple Disulfide Bonds in the *Escherichia coli* Cytoplasm," PNAS, 96:13703-13708 (1999).
Bessette et al., "In Vivo and in Vitro Function of the *Escherichia coli* Periplasmic Cysteine Oxidoreductase DsbG," The Journal of Biological Chemistry, 274(12):7784-7792 (1999).
Bilgrami et al., "Crystal Structure of Schistatin, a Disintegrin Homodimer from Saw-Scaled Viper (*Echis carinatus*) at 2.5 Å Resolution," J. Mol. Biol., 341:829-837 (2004).
Branden et al., Introduction to Protein Structure Second Edition, Garland Publishing Inc., New York, pp. 382 (1999).
Bridges et al., "Integrin $\alpha 4\beta 1$-Dependent adhesion to ADAM 28 (MDC-L) requires an extended surface of the disintegrin domain," Biochemistry, 42:3734-3741 (2003).

(Continued)

Primary Examiner — Suzanne M Noakes
Assistant Examiner — Jae W Lee
(74) Attorney, Agent, or Firm — Foley & Lardner LLP; Antoinette F. Konski

(57) ABSTRACT

This invention relates to methods of inhibiting binding between a cell expressing integrin receptors specific for one or more integrins selected from the group consisting of $\alpha IIb\beta 3$, $\alpha v\beta 3$, $\alpha v\beta 5$, or $\alpha 5\beta 1$, said method comprising contacting the cell with a monomeric disintegrin or monomeric disintegrin domain which comprises a C-terminal sequence non-native to the disintegrin or disintegrin domain, said C-terminal sequence encoding a functional integrin-binding loop.

5 Claims, 23 Drawing Sheets

OTHER PUBLICATIONS

Calvete et al., "Disulphide-Bond Pattern and Molecular Modelling of the Dimeric Disintegrin EMF-10, a Potent and Selective Integrin $\alpha_5\beta_1$ Antagonist from *Eristocophis macmahoni* Venom," Biochem. J., 345:573-581 (2000).
Chao et al., "*Agkistrodon piscivorus* piscivorus platelet aggregation inhibitor: a potent inhibitor of platelet activation," PNAS, 86:8050-8054 (1989).
Chen et al., "Chaperone Activity of DsbC," The Journal of Biological Chemistry, 274(28):19601-19605 (1999).
Chivers et al., "General Acid/Base Catalysis in the Active Site of *Escherichia coli* Thioredoxin," Biochemistry, 36:15810-15816 (1997).
Chivers et al., "The CXXC Motif: A Rheostat in the Active Site," Biochemistry, 36(14):4061-4066 (1997).
Chung et al., "Transfer of Electrons Across the Cytoplasmic Membrane by DsbD, a Membrane Protein Involved in Thiol-Disulphide Exchange and Protein Folding in the Bacterial Periplasm," Molecular Microbiology, 35(5):1099-1109 (2000).
Collet et al., "Disulfides Out of Thin Air," Nature Structural Biology, 9:2-3 (2002).
Collet et al., "Oxidative Protein Folding in Bacteria," Molecular Microbiology, 44(1):1-8 (2002).
Collet et al., "Reconstitution of a Disulfide Isomerization System," The Journal of Biological Chemistry, 277(30):26886-26892 (2002).
Darby et al., "Identifying and Characterizing a Second Structural Domain of Protein Disulfide Isomerase," FEBS Letters, 448:167-172 (1999).
Di Luccio et al., "Parameters Affecting in Vitro Oxidation/Folding of Maurotoxin, a Four-Disulphide-Bridged Scorpion Toxin," Biochem. J., 358:681-692 (2001).
Dubendorff et al., "Controlling Basal Expression in an Inducible T7 Expression System by Blocking the Target T7 Promoter with Lac Repressor," J. Mol. Biol., 219:45-59 (1991).
European Search Report dated Dec. 30, 2009 for EP Application No. 06849695.9.
Ferrero et al., "The Platelet Endothelial Cell Adhesion Molecule-1 (PECAM1) Contributes to Endothelial Barrier Function," FEBS Letters, 374:323-326 (1995).
Frydman, "Folding of Newly Translated Proteins in Vivo: The Role of Molecular Chaperones," Annu. Rev. Biochem., 70:603-647 (2001).
Fujii et al., "Crystal Structure of Trimestatin, a Disintegrin Containing a Cell Adhesion Recognition Motif RGD," J. Mol. Biol., 332:1115-1122 (2003).
Fujii et al., "The Formation of Amphotericin B Ion Channels in Lipid Bilayers," Biochemistry, 36:4959-4968 (1997).
Georgiou et al., "Expression of Correctly Folded Proteins in *Escherichia coli*," Current Opinion in Biotechnology, 7:190-197 (1996).
Goldstone et al., "DsbC Activation by the N-Terminal Domain of DsbD," PNAS, 98,(17):9551-9556 (2001).
Golubkov et al., "Anti-angiogenic activity of contortrostatin, a disintegrin from *Agkistrodon contortrix* contortrix snake venom," Angiogenesis, 6:213-224 (2003).
Gordon et al., "*Escherichia coli* DipZ: Anatomy of a Transmembrane Protein Disulphide Reductase in Which Three Pairs of Cysteine Residues, One in Each of Three Domains, Contribute Differentially to Function," Molecular Microbiology, 35(6):1360-1374 (2000).
Goulding et al., "Thiol-Disulfide Exchange in an Immunoglobulin-Like Fold: Structure of the N-Terminal Domain of DsbD," Biochemistry, 41:6920-6927 (2002).
Grauschopf, et al., "Why is DsbA Such an Oxidizing Disulfide Catalyst?," Cell, 83:947-955 (1995).
Gross et al., "A New FAD-Binding Fold and Intersubunit Disulfide Shuttle in the Thiol Oxidase Erv2p," Nature Structural Biology, 9(1):61-67 (2002).
Guddat et al., "Crystal Structures of Reduced and Oxidized DsbA: Investigation of Domain Motion and Thiolate stabilization," Structure, 6:757-767 (1998).
Guddat et al., "The Uncharged Surface Features Surrounding the Active Site of *Escherichia coli* DsbA are Conserved and are Implicated in Peptide Binding," Protein Science, 6:1148-1156 (1997).

Guerdoux-Jamet et al., "Using Codon Usage to Predict Genes Origin: Is the *Escherichia coli* Outer Membrane a Patchwork of Products form Different Genomes?," DNA Research, 4:257-265 (1997).
Haebel et al., "The Disulfide Bond Isomerase DsbC is Activated by an Immunoglobulin-Fold Thiol Oxidoreductase: Crystal Structure of the DsbC-DsbD? Complex," The EMBO Journal, 21(18):4774-4784 (2002).
Holmgren, "Thiroedoxin Structure and Mechanism: Conformational Changes on Oxidation of the Active-Site Sulfhydryls to a Disulfide," Structure, 3:239-243 (1995).
Hoshino et al., "Production of Brain-Derived Neurotrophic Factor in *Escherichia coli* by Coexpression of Dsb Proteins," Biosci. Biotechnol. Biochem., 66(2):344-350 (2002).
International Search Report and the Written Opinion dated May 21, 2010 for PCT Application No. PCT/US09/64256.
International Search Report dated Jun. 2, 2008 for PCT Application No. PCT/US06/04413.
Interview Summary dated Aug. 11, 2009 for U.S. Appl. No. 11/351,311.
Jurado et al., "Production of Functional Single-Chain Fv Antibodies in the Cytoplasm of *Escherichia coli*," J. Mol. Biol., 320:1-10 (2002).
Kadokura et al., "Protein Disulfide Bond Formation in Prokaryotes," Annu. Rev. Biochem., 72:111-135 (2003).
Kassab et al., "Cloning, expression, and structural analysis of recombinant BJcuL, a c-type lectin from the *Bothrops jararacussu* snake venom," Protein Expression and Purification, 35(2):344-352 (2004).
Katzen et al., "Role and Location of the Unusual Redox-Active Cysteines in the Hydrophobic Domain of the Transmembrane Electron Transporter DsbD," PNAS, 100(18):10471-10476 (2003).
Katzen et al., "Transmembrane Electron Transfer by the Membrane Protein DsbD Occurs Via a Disulfide Bond Cascade," Cell, 103:769-779 (2000).
Kemmink et al., "The Folding Catalyst Protein Disulfide Isomerase is Constructed of Active and Inactive Thioredoxin Molecules," Current Biology, 7:239-245 (1997).
Kim et al., "Efficient Production of a Bioactive, Multiple Disulfide-Bonded Protein Using Modified Extracts of *Escherichia coli*," Biotechnology and Bioengineering, 85:122-129 (2004).
Kisselev, "Polypeptide release factors in prokaryotes and eukaryotes: same function, different structure," Structure, 10:8-9 (2002).
Kurokawa et al., "Overexpression of Protein Disulfide Isomerase DsbC Stabilizes Multiple-Disulfide-Bonded Recombinant Protein Produced and Transported to the Periplasm in *Escherichia coli*," Applied and Environmental Microbiology, 66(9):3960-3965 (2000).
Kurokawa et al., "Overproduction of Bacterial Protein Disulfide Isomerase (DsbC) and Its Modulator (DsbD) Markedly Enhances Periplasmic Production of Human Nerve Growth Factor in *Escherichia coli*," Journal of Biological Chemistry, 276(17):14393-14399 (2001).
LaVallie et al., "A Thioredoxin Gene Fusion Expression System That Circumvents Inclusion Body Formation in the *E. coli* Cytoplasm," Bio/Technology, 11:187-193 (1993).
Levy et al., "Production of Correctly Folded Fab Antibody Fragment in the Cytoplasm of *Escherichia coli* trxB gor Mutants via the Coexpression of Molecular Chaperones," Protein Expression and Purification, 23:338-347 (2001).
Liu et al., "Disulfide-Dependent Folding and Export of *Escherichia coli* DsbC," The Journal of Biological Chemistry, 276(2):1146-1151 (2001).
Makrides, "Strategies for Achieving High-Level Expression of Genes in *Escherichia coli*," Microbiological Reviews, American Society for Microbiology, Washington, DC, US, 60(3):512-538 (1996).
Marcinkiewicz, "Functional characteristic of snake venom disintegrins: potential therapeutic implication," Current Pharmaceutical Design, 11(7):815-827 (2005).
Markland et al., "A Novel Snake Venom Disintegrin That Inhibits Human Ovarian Cancer Dissemination and Angiogenesis in an Orthotopic Nude Mouse Model," Haemostasis 31(3-6): 183-191 (2001).
Martin et al., "Crystal Structure of the DsbA Protein Required for Disulphide Bond Formation in Vivo," Nature, 365:464-468 (1993).
Martin, "Thioredoxin—A Fold for All Reasons," Structure, 3:245-250 (1995).

Maskos et al., "DsbA and DsbC-Catalyzed Oxidative Folding of Proteins with Complex Disulfide Bridge Patterns In Vitro and In Vivo," J. Mol. Biol., 325:495-513 (2003).

McCarthy et al., "Crystal Structure of the Protein Disulfide Bond Isomerase, DsbC, from *Escherichia coli*," Nature America Inc., 7(3):196-199 (2000).

McLane et al., "Proceedings of the Society for Experimental Biology and Medicine," Proc. Soc. Exp. Biol. Med., 219(2):109-119 (1998).

Minea et al., "Development of a novel recombinant disintegrin, contortrostatin, as an effective anti-tumor and anti-angiogenic agent," Pathophysical Haemost Thromb, 34(4-5): 177-183 (2005).

Missiakas et al., "Protein Folding in the Bacterial Periplasm," Journal of Bacteriology, 179(8):2465-2471 (1997).

Missiakas et al., "Protein Misfolding in the Cell Envelope of *Escherichia coli*: New Signaling Pathways," TIBS, 22:59-63 (1997).

Missiakas et al., "The *Escherichia coli* dsbC (xprA) Gene Encodes a Periplasmic Protein Involved in Disulfide Bond Formation," The EMBO Journal, 13(8):2013-2020 (1994).

Moiseeva et al., "Purification, Crystallization and Preliminary X-Ray Analysis of the Disintegrin Contortrostatin From Agkistrodon Contortrix Contortrix Snake Venom," Acta Cryst., D58:2122-2124 (2002).

Mössner et al., Characterization of *Escherichia coli* Thioredoxin Variants Mimicking the Active-Sites of Other Thiol/Disulfide Oxidoreductases, Protein Science, 7:1233-1244 (1998).

Mössner et al., "Importance of Redox Potential for the In Vivo Function of the Cytoplasmic Disulfide Reductant Thioredoxin from *Escherichia coli*," The Journal of Biological Chemistry, 274(36):25254-25259 (1999).

Mössner et al., "Influence of the pKa Value of the Buried, Active-Site Cysteine on the Redox Properties of Thioredoxin-Like Oxidoreductases," FEBS Letters, 477:21-26 (2000).

Moura-da-Silva et al., "Jararhagin ECD-Containing Disintegrin Domain: Expression in *Escherichia coli* and Inhibition of the Platelet-Collagen Interaction," Archives of Biochemistry and Biophysics, 369(2):295-301 (1999).

NCBI protein search result of "disintegrin", Retrieved from the Internet <URL:http://www.ncbi.nlm.nih.gov/sites/entrez>. Retrieved on May 6, 2009.

O'Brien et al., "The Adaptability of *Escherichia coli* Thioredoxin to Non-Convervative Amino Acid Substitutions," Protein Sci., 6:1325-1332 (1997).

Office Action dated Jul. 2, 2010 for Australian Application No. 2006336468.

Prinz et al., "The Role of the Thioredoxin and Glutaredoxin Pathways in Reducing Protein Disulfide Bonds in the *Escherichia coli* Cytoplasm," The Journal of Biological Chemistry, 272(25):15661-15667 (1997).

Raina et al., "Making and Breaking Disulfide Bonds," Annu. Rev. Microbiol., 51:179-202 (1997).

Rietsch et al., "An In Vivo Pathway for Disulfide Bond Isomerization in *Escherichia coli*," PNAS, 93:13048-13053 (1996).

Rietsch et al., "Reduction of the Periplasmic Disulfide Bond Isomerase, DsbC, Occurs by Passage of Electrons from Cytoplasmic Thioredoxin," Journal of Bacteriology, 179(21):6602-6608 (1997).

Ritz et al., "Roles of Thiol-Redox Pathways in Bacteria," Annu. Rev. Microbiol., 55:21-48 (2001).

Ritz et al., "Thioredoxin 2 is Involved in the Oxidative Stress Response in *Escherichia coli*," The Journal of Biological Chemistry, 275(4):2505-2512 (2000).

Rorrer et al., "Autocatalytic Activity of the Tobacco Etch Virus NIa Proteinase in Viral and Foreign Protein Sequences," Journal of General Virology, 73(4):775-783 (1992).

Schäfer et al., "Skp, a Molecular Chaperone of Gram-Negative Bacteria, is Required for the Formation of Soluble Periplasmic Intermediates of Outer Membrane Proteins," The Journal of Biological Chemistry, 274(35):24567-24574 (1999).

Stewart et al., "Disulfide Bond Formation in the *Escherichia coli* Cytoplasm: an in Vivo Role Reversal for the Thioredoxins," The EMBO Journal, 17(19):5543-5550 (1998).

Studier et al., "Use of T7 RNA Polymerase to Direct Expression of Cloned Genes," Methods in Enzymology, 185:60-89 (1990).

Studier, "Use of Bacteriophage T7 Lysozyme to Improve an Inducible T7 Expression System," J. Mol. Biol., 219:37-44 (1991).

Supplemental European Search Report dated Jun. 21, 2010 for EP Application No. 07776668.1.

Swartz, "Advances in *Escherichia coli* Production of Therapeutic Proteins," Current Opinion in Biotechnology, 12:195-201 (2001).

Swenson et al., "Chimeric derivative of fibrolase, a fibrinolytic enzyme from southern copperhead venom, possesses inhibitory activity on platelet aggregation," Arch. Biochem. Biophys., 384(2):227-237 (2000).

Swenson et al., "Intravenous Liposomal Delivery of the Snake Venom Disintegrin Contortrostatin Limits Breast Cancer Progression," Mol. Cancer Ther., 3(4):499-511 (2004).

US Notice of Allowance dated Feb. 4, 2010 for U.S. Appl. No. 11/351,311.

US Notice of Allowance dated Aug. 24, 2009 for U.S. Appl. No. 11/351,311.

US Office Action dated Feb. 19, 2008 for U.S. Appl. No. 11/351,311.

US Office Action dated May 8, 2009 for U.S. Appl. No. 11/351,311.

US Office Action dated Jun. 9, 2010 for U.S. Appl. No. 11/742,389.

US Office Action dated Sep. 4, 2008 for U.S. Appl. No. 11/351,311.

Vella et al., "A Recombinant Chimeric Epidermal Growth Factor-like Module with High Binding Affinity for Integrins," J Bioi Chem., 278(22):19834-19843 (2003).

Venturi et al., "High Level Production of Functional Antibody Fab Fragments in an Oxidizing Bacterial Cytoplasm," J. Mol. Biol., 315:1-8 (2002).

Walker et al., "Effect of Redox Environment on the in Vitro and in Vivo Folding of RTEM-1 β-Lactamase and *Escherichia coli* Alkaline Phosphatase," The Journal of Biological Chemistry, 269(45):28487-28493 (1994).

Wang et al., "A Unique Approach for High Level Expression and Production of a Recombinant Cobra Neurotoxin in *Escherichia coli*," Journal of Biotechnology, 94:235-244 (2002).

Wierzbicka-Patynowski et al., "Structural Requirements of Echistatin for the Recognition of $\alpha_v\beta_3$ and $\alpha_5\beta_1$ Integrins," The Journal of Biological Chemistry, 274(53):37809-37814 (1999).

Wishart et al., "A single mutation converts a novel phosphotyrosine binding domain into a dual-specificity phosphatase," Journal of Biological Chemistry, 270(45):26782-26785 (1995).

Witkowski et al., "Conversion of a beta-ketoacyl synthase to a malonyl decarboxylase by replacement of the active-site cysteine with glutamine," Biochemistry, 38:11643-11650 (1999).

Woycechowsky et al., "The CXC Motif: A Functional Mimic of Protein Disulfide Isomerase," Biochemistry, 42:5387-5394 (2003).

Yasukawa et al., "Increase of solubility of foreign proteins in *Escherichia coli* by coproduction of the bacterial thioredoxin," Journal of Biological Chemistry, 270(43):25328-25331 (1995).

Yuan et al., "The role of thioredoxin and disulfide isomerase in the expression of the snake venom thrombin-like enzyme calobin in *Escherichia coli* BL21 (DE3)," Protein Expression and Purification, 38(1):51-60 (2004).

Zapun et al., "Structural and Functional Characterization of DsbC, a Protein Involved in Disulfide Bond Formation in *Escherichia coli*," Biochemistry, 34:5075-5089 (1995).

Zapun et al., "The Reactive and Destabilizing Disulfide Bond of DsbA, a Protein Required for Protein Disulfide Bond Formation in Vivo," Biochemistry, 32:5083-5092 (1993).

Zhang et al., "Expression of Eukaryotic Proteins in Soluble Form in *Escherichia coli*," Prot. Exp. And Purif., 12:159-165 (1998).

Zhang et al., "Low-Usage Codons in *Escherichia coli*, Yeast, Fruit Fly and Primates," Gene, 105:61-72 (1991).

Zhao et al., "Dimerization by Domain Hybridization Bestows Chaperone and Isomerase Activities," The Journal of Biological Chemistry, 278(44):43292-43298 (2003).

Zhou et al., "Contortrostatin, a dimeric disintegrin from Agkistrodon contortrix contortrix, inhibits angiogenesis," Angiogenesis, 3(3):259-269 (1999).

Zhou et al., "Contortrostatin, a Dimeric Disintegrin from Agkistrodon Contortrix Contortrix, Inhibits Breast Cancer Progression," Breast Cancer Research and Treatment, 61(3):249-260 (2000).

Zhou et al., "Contortrostatin, a Homodimeric Disintegrin, Binds to Integrin αvβ5," Biochem. Biophys. Res. Commun., 267:350-355 (2000).

Zhou et al., "Molecular Cloning and Functional Expression of Contortrostatin, A Homodimeric Disintegrin From Southern Copperhead Snake Venom," Biochem. Biophys., 375(2): 278-288 (2000).

Ahmed et al., "The Extracellular Matrix Protein TGFB1 Induces Microtubule Stabilization and Sensitizes Ovarian Cancers to Paclitaxel," Cancer Cell., 12(6):514-527 (2007).

Beekman et al., "Phase II Evaluations of Cilengitide in Asymptomatic Patients with Androgen-Independent Prostate Cancer: Scientific Rationale and Study Design," Clinical Genitourinary Cancer, 4(4):299-302 (2006).

Bergstralh et al., "Microtubule stabilizing agents: Their molecular signaling consequences and the potential for enhancement by drug combination," Cancer Treatment Reviews, 32(3):166-179 (2006).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Journal of Cell Biology, 111:2129-2138 (1990).

Communication pursuant to Article 94(3) EPC dated Mar. 17, 2011 in EP Appl. No. 07776668.1.

Dyce et al., "Integrins in Head and Neck Squamous Cell Carcinoma Invasion," The Larygoscope, 112:2025-2032 (2002).

Inoue et al., "Docetaxel Enhances the Therapeutic Effect of the Angiogenesis Inhibitor TNP-470 (AGM-1470) in Metastatic Human Transitional Cell Carcinoma," Clinical Cancer Research: An Official Journal of the American Associate for Cancer Research, 9(2):886-899 (2003).

International Search Report and the Written Opinion dated May 11, 2010 for PCT Appl. No. PCT/US2010/024166.

International Search Report dated May 26, 2011 for PCT Appl. No. PCT/US2011/024243.

International Search Report dated Nov. 13, 2007 for PCT Appl. No. PCT/US2007/010707.

Juarez et al., "Evolution of Snake Venom Disintegrins by Positive Darwinian Selection," Mol Biol Evol, 25(11):2391-2407 (2008).

Kim et al., Combined anti-angiogenic therapy against VEGF and integrin $\alpha_v\beta_3$ in an orthotopic model of ovarian cancer, Cancer Biology & Therapy, 8(23):2261-2270 (2009).

Lazar et al., "Transforming Growth Factor alpha: Mutation of Aspartic Acid 47 and Leucine 48 Results in Different Biological Activities," Molecular and Cellular Biology, 8(3):1247 (1988).

Li et al., "Correlation of integrin β3 mRNA and vascular endothelial growth factor protein expression profiles with the clinicopathological features and prognosis of gastric carcinoma," World J Gastroenterology, 14(3):421-427 (2008).

Lutolf et al., "Synthetic biomaterials as instructive extracellular microenvironments for morphogenesis in tissue engineering," Nat Biotech, 23(1):47-55 (2005).

Mattern et al., "Giloma cell integrin expression and their interactions with integrin antagonists," Cancer Therapy, 3:325-340 (2005).

Miles et al., "Combination Versus Sequential Single-Agent Therapy in Metastatic Breast Cancer," The Oncologist, 7(suppl 6):13-19 (2002).

Niewiarowski et al., "Disintegrins and Other Naturally Occurring Antagonists of Platelet Fibrinogen Receptors," Seminars in Hematology, 31(4):289-300 (1994).

Notice of Allowance dated Feb. 4, 2010 for US Appl. No. 11/351,311.
Notice of Allowance dated Apr. 18, 2011 in US Appl. No. 11/742,389.
Notice of Allowance dated Oct. 4, 2011 in US Appl. No. 12/831,226.
Office Action dated Jan. 6, 2012 for JP Appl. No. 2007-556197.
Office Action dated Jan. 26, 2010 for US Appl. No. 11/742,389.
Office Action dated Feb. 19, 2008 for U.S. Appl. No. 11/351,311.
Office Action dated Sep. 4, 2008 for U.S. Appl. No. 11/351,311.
Office Action dated Dec. 3, 2010 for U.S. Appl. No. 11/742,389.

Skolnick et al., "From genes to protein structure and function: novel applications of computational approaches in the genomic era," Trends in Biotech, 18(1):34-39 (2000).

Takeda et al., Crystal structures of VAP1 reveal ADAMs' MDC domain architecture and its unique C-shaped scaffold, EMBO J, 25(11):2388-2396 (2006).

Yeh et al., "Rhodostomin, A Snake Venom Disintegrin, Inhibits Angiogenesis Elicited by Basic Fibroblast Growth Factor and Suppresses Tumor Growth by a Selective $\alpha_v\beta_3$ Blockade of Endothelial Cells," Molecular Pharmacology, 59(5):1333-1342 (2001).

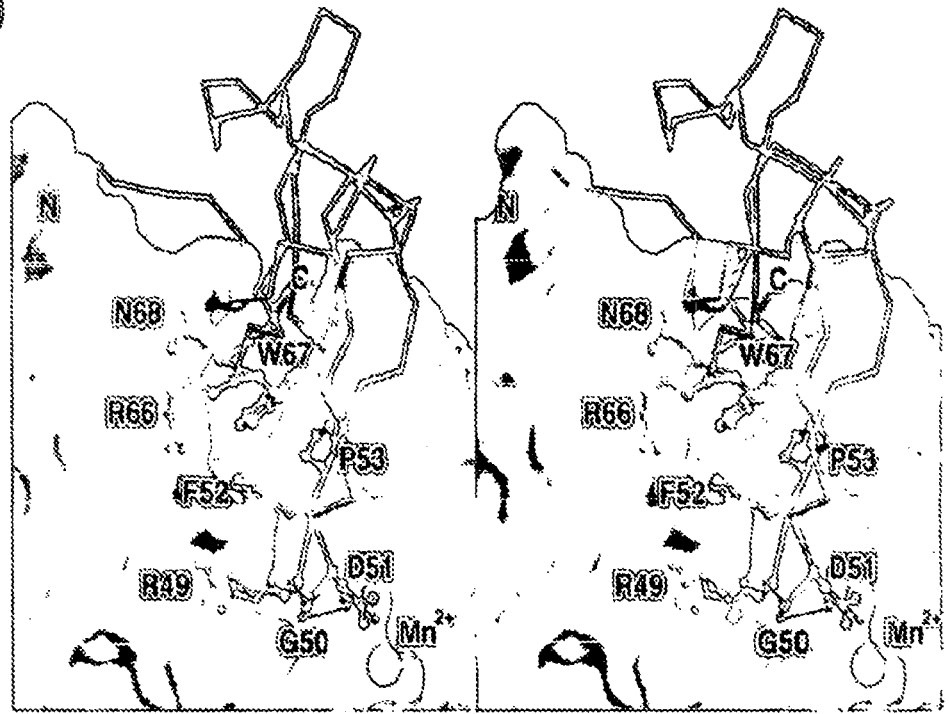
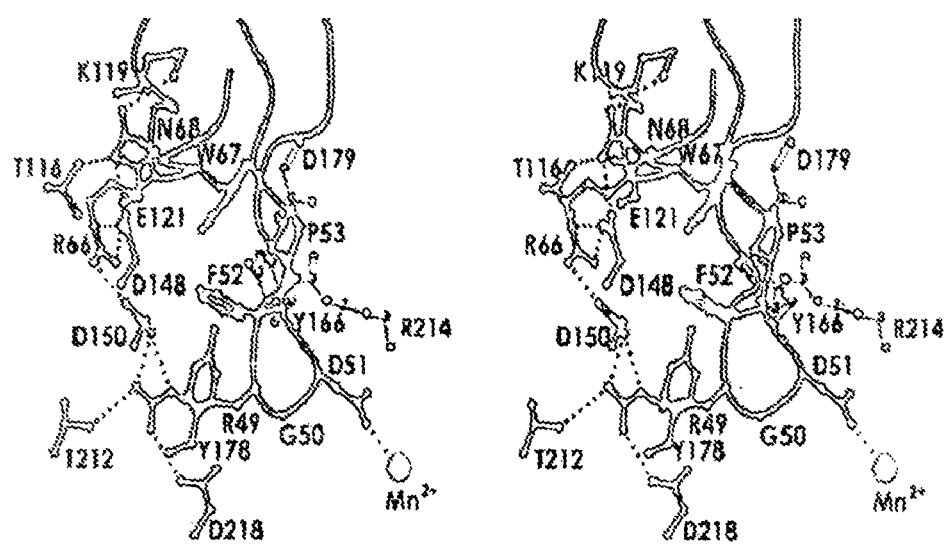
FIG. 7

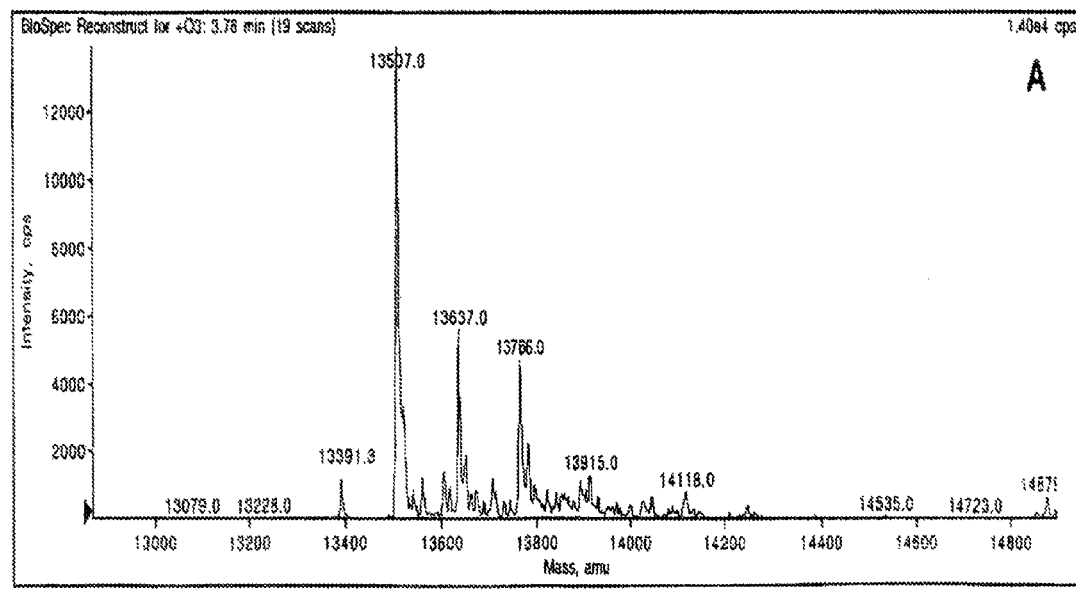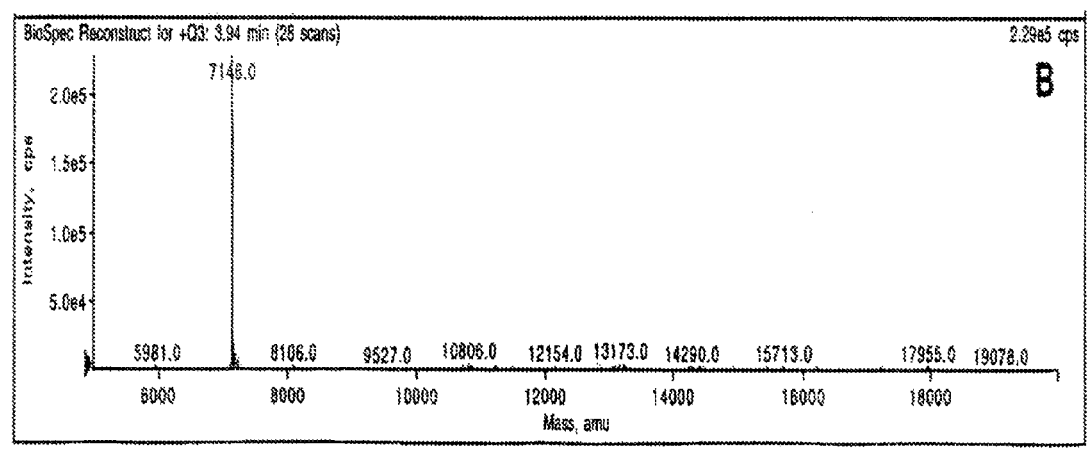
FIG. 15

Codon Usage in *E. coli*

| Amino Acid | Codon | Class I | Class II | Class III | Amino Acid | Codon | Class I | Class II | Class III |
|---|---|---|---|---|---|---|---|---|---|
| Phe | TTT | 55.09 | 29.08 | 67.14 | Leu | CTT | 9.70 | 5.56 | 19.00 |
| | TTC | 44.91 | 70.92 | 32.86 | | CTC | 10.40 | 8.03 | 9.04 |
| Leu | TTA | 10.99 | 3.44 | 20.09 | | CTA | 3.09 | 0.83 | 6.81 |
| | TTG | 13.02 | 5.47 | 15.05 | | CTG | 52.79 | 76.67 | 29.99 |
| Ser | TCT | 13.26 | 32.41 | 19.63 | Pro | CCT | 13.71 | 11.23 | 28.30 |
| | TCC | 15.02 | 26.56 | 11.34 | | CCC | 11.19 | 1.63 | 16.26 |
| | TCA | 10.83 | 4.79 | 22.09 | | CCA | 18.63 | 15.25 | 31.50 |
| | TCG | 16.88 | 7.39 | 10.60 | | CCG | 56.47 | 71.89 | 23.94 |
| Tyr | TAT | 54.42 | 35.23 | 69.60 | His | CAT | 56.80 | 29.77 | 61.69 |
| | TAC | 45.58 | 64.77 | 30.40 | | CAC | 43.20 | 70.23 | 38.31 |
| TER | TAA | | | | Gln | CAA | 33.40 | 18.65 | 37.06 |
| | TAG | | | | | CAG | 66.60 | 81.35 | 62.94 |
| Cys | TGT | 40.90 | 38.85 | 55.71 | Arg | CGT | 38.99 | 64.25 | 26.05 |
| | TGC | 59.10 | 61.15 | 44.29 | | CGC | 42.23 | 32.97 | 21.94 |
| TER | TGA | | | | | CGA | 5.52 | 1.07 | 12.80 |
| Trp | TGG | 100.00 | 100.00 | 100.00 | | CGG | 8.97 | 0.80 | 13.62 |
| Ile | ATT | 51.20 | 33.49 | 47.57 | Val | GTT | 23.74 | 39.77 | 34.33 |
| | ATC | 44.37 | 65.94 | 26.65 | | GTC | 22.48 | 13.45 | 18.95 |
| | ATA | 4.43 | 0.57 | 25.78 | | GTA | 14.86 | 19.97 | 21.78 |
| Met | ATG | 100.00 | 100.00 | 100.00 | | GTG | 38.92 | 26.81 | 24.94 |
| Thr | ACT | 14.85 | 29.08 | 26.83 | Ala | GCT | 14.52 | 27.54 | 22.86 |
| | ACC | 46.83 | 53.60 | 24.45 | | GCC | 27.62 | 16.14 | 23.67 |
| | ACA | 10.52 | 4.67 | 27.93 | | GCA | 19.63 | 24.01 | 31.27 |
| | ACG | 27.81 | 12.65 | 20.80 | | GCG | 38.23 | 32.30 | 22.19 |
| Asn | AAT | 40.87 | 17.25 | 64.06 | Asp | GAT | 62.83 | 46.05 | 70.47 |
| | AAC | 59.13 | 82.75 | 35.94 | | GAC | 37.17 | 53.95 | 29.53 |
| Lys | AAA | 75.44 | 78.55 | 72.21 | Glu | GAA | 68.33 | 75.35 | 66.25 |
| | AAG | 24.56 | 21.45 | 27.79 | | GAG | 31.67 | 24.65 | 33.75 |
| Ser | AGT | 13.96 | 4.52 | 18.73 | Gly | GGT | 32.91 | 50.84 | 31.79 |
| | AGC | 30.04 | 24.33 | 17.61 | | GGC | 43.17 | 42.83 | 24.51 |
| Arg | AGA | 1.75 | 0.62 | 15.63 | | GGA | 9.19 | 1.97 | 24.75 |
| | AGG | 1.54 | 0.29 | 9.96 | | GGG | 14.74 | 4.36 | 18.95 |

FIG. 16

The 8 least used codons in *E. coli*, yeast, *Drosophila*, and primates

| *E. coli* | yeast | *Drosophila* | primates | amino acid |
|---|---|---|---|---|
| AGG | AGG | | | arginine |
| AGA | | AGA | | arginine |
| AUA | | AUA | | isoleucine |
| CUA | | | | leucine |
| CGA | CGA | CGA | CGA | arginine |
| CGG | CGG | CGG | CGG | arginine |
| CCC | | | | proline |
| UCG | | | UCG | serine |
| | CGC | | CGC | arginine |
| | CCG | | CCG | proline |
| | CUC | | | leucine |
| | GCG | | GCG | alanine |
| | ACG | | ACG | threonine |
| | | UUA | | leucine |
| | | GGG | | glycine |
| | | AGU | | serine |
| | | UGU | | cysteine |
| | | | CGU | arginine |

FIG. 17

```
ATG ATC CAG GTT CTC TTG GTG ACT CTA TGC TTA GCA GCT TTT CCT TAT CAA
GGG AGC TCT ATA ATC CTG GAA TCT GGG AAT GTT AAT GAT TAT GAA GTA CTG
TAT CCA CAA AAA GTC ACT GCA TTG CCC AAA GGA GCA GTT CAG CCA AAG TAT
GAA GAC ACC ATG CAA TAT GAA TTT AAA GTG AAT GGA GAG CCA GTG GTC CTT
CAC CTG GAA AAA AAT AAA GGA CTT TTT TCA AAA GAT TAC AGC GAG ACT CAT
TAT TCC TCT GAT GGC AGA AAA ATT ACA ACA AAC CCT CCG GTT GAG GAT CAC
TGC TAT TAT CAT GGA CGC ATC CAG AAT GAT GCT GAC TCA ACT GCA AGC ATC
AGT GCA TGC AAC GGT TTG AAA GGA CAT TTC AAG CTT CAA GGG GAG ACG TAC
CTT ATT GAA CCC TTG AAG CTT TCC GAC AGT GAA GCC CAT GCA GTC TAC AAA
TAT GAA AAC GTA GAA AAA GAA GAT GAG GCC CCC AAA ATG TGT GGG GTA ACC
CAG ACT AAT TGG GAA TCA GAT GAG CCC ATC AAA AAG GCC TCT CAG TTA AAT
CTT ACT CCT GAA CAA CAA GGA TTC CCC CAA AGA TAC ATT GAG CTT GTT GTA
GTT GCA GAT CAC AGA ATG TTC ACG AAA TAC AAC GGC AAT TTA AAT ACT ATT
AGA ATA TGG GTA CAT GAA CTT GTC AAC ACT ATG AAT GTG TTT TAC AGA CCT
TTG AAT ATT CGT GTC TCA CTG ACT GAC CTA GAA GTT TGG TCA GAC CAA GAT
TTG ATC AAC GTG CAG CCA GCA GCG GCT GAT ACT TTG GAA GCA TTT GGA GAC
TGG AGA GAG ACA GTC TTG CTG AAT CGC ATA AGT CAT GAT AAT GCT CAG TTA
CTC ACG GCC ATT GAG CTT GAT GGA GAA ACT ATA GGA TTG CTA ACA GGG GCC
ACC ATG TGC GAC CCG AAG CTT TCT ACA GGA ATT GTT CAG GAT CAT AGT GCA
ATA AAT CTT TGG GTT GCA GTT ACA ATG GCC CAT GAG ATG GGT CAT AAT CTG
GGT ATT AGT CAC GAT GGA AAT CAG TGT CAT TGC GAT GCT AAC TCA TGC ATT
ATG AGT GAA GAA CTA AGA GAA CAA CTT TCC TTT GAG TTC AGC GAT TGT AGT
CAG AAT CAA TAT CAG ACA TAT CTT ACT GAT CAT AAC CCA CAA TGC ATG CTC
AAT GAA CCC TTG AGA ACA GAT ATT GTT TCA ACT CCA GTT TCT GGA AAT GAA
CTT TTG GAG ACG GGA GAA GAA AGT GAC TTT GAC GCT CCT GCA AAT CCG TGC
TGC GAT GCT GCA ACA TGT AAA CTG ACA ACA GGG TCA CAG TGT GCA GAT GGA
CTG TGT TGT GAC CAG TGC AAA TTT ATG AAA GAA GGA ACA GTA TGC CGG AGA
GCA AGG GGT GAT GAC CTG GAT GAT TAC TGC AAT GGC ATA TCT GCT GGC TGT
CCC AGA AAT CCC TTC CAT GCC
```

FIG. 18A

```
ATG ATC CAG GTT CTC TTG GTG ACT CTA TGC TTA GCA GCT TTT CCT TAT CAA
GGG AGC TCT ATA ATC CTG GAA TCT GGG AAT GTT AAT GAT TAT GAA GTA CTG
TAT CCA CAA AAA GTC ACT GCA TTG CCC AAA GGA GCA GTT CAG CCA AAG TAT
GAA GAC ACC ATG CAA TAT GAA TTT AAA GTG AAT GGA GAG CCA GTG GTC CTT
CAC CTG GAA AAA AAT AAA GGA CTT TTT TCA AAA GAT TAC AGC GAG ACT CAT
TAT TCC TCT GAT GGC AGA AAA ATT ACC ACC AAC CCT CCG GTT GAG GAT CAC
TGC TAT TAT CAT GGA CGC ATC CAG AAT GAT GCT GAC TCA ACT GCA AGC ATC
AGT GCA TGC AAC GGT TTG AAA GGA CAT TTC AAG CTT CAA GGG GAG ACG TAC
CTT ATT GAA CCC TTG AAG CTT TCC GAC AGT GAA GCC CAT GCA GTC TAC AAA
TAT GAA AAC GTA GAA AAA GAA GAT GAG GCC CCC AAA ATG TGT GGG GTA ACC
CAG ACT AAT TGG GAA TCA GAT GAG CCC ATC AAA AAG GCC TCT CAG TTA AAT
CTT ACT CCT GAA CAA CAA GGA TTC CCC CAA AGA TAC ATT GAG CTT GTT GTA
GTT GCA GAT CAC AGA ATG TTC ACG AAA TAC AAC GGC AAT TTA AAT ACT ATT
AGA ATA TGG GTA CAT GAA CTT GTC AAC ACT ATG AAT GTG TTT TAC AGA CCT
TTG AAT ATT CGT GTC TCA CTG ACT GAC CTA GAA GTT TGG TCA GAC CAA GAT
TTG ATC AAC GTG CAG CCA GCA GCG GCT GAT ACT TTG GAA GCA TTT GGA GAC
TGG AGA GAG ACA GTC TTG CTG AAT CGC ATA AGT CAT GAT AAT GCT CAG TTA
CTC ACG GCC ATT GAG CTT GAT GGA GAA ACT ATA GGA TTG CTA ACA GGG GC
ACC ATG TGC GAC CCG AAG CTT TCT ACC GGA ATT GTT CAG GAT CAT AGT GCA
ATA AAT CTT TGG GTT GCA GTT ACT ATG GCC CAT GAG ATG GGT CAT AAT CTG
GGT ATT AGT CAC GAT GGA AAT CAG TGT CAT TGC GAT GCT AAC TCA TGC ATT
ATG AGT GAA GAA CTA AGA GAA CAA CTT TCC TTT GAG TTC AGC GAT TGT AGT
CAG AAT CAA TAT CAG ACA TAT CTT ACT GAT CAT AAC CCA CAA TGC ATG CTC
AAT GAA CCC TTG AGA ACA GAT ATT GTT TCA ACT CCA GTT TCT GGA AAT GAA
CTT TTG GAG ACG GGA GAA GAA AGT GAC TTT GAC GCT CCT GCA AAT CCG TGC
TGC GAT GCT GCA ACC TGT AAA CTG ACC ACC GGG TCA CAG TGT GCA GAT GGA
CTG TGT TGT GAC CAG TGC AAA TTT ATG AAA GAA GGA ACC GTA TGC CGT AGA
GCA AGG GGT GAT GAC CTG GAT GAT TAC TGC AAT GGC ATA TCT GCT GGC TGT
CCC AGA AAT CCC TTC CAT GCC
```

FIG. 18B

```
                         SEQUENCE LISTING

<160> NUMBER OF SEQ ID NOS: 56

<210> SEQ ID NO 1
<211> LENGTH: 109
<212> TYPE: PRT
<213> ORGANISM: Escherichia coli

<400> SEQUENCE: 1

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 2
<211> LENGTH: 65
<212> TYPE: PRT
<213> ORGANISM: Agkistrodon contortrix

<400> SEQUENCE: 2

Asp Ala Pro Ala Asn Pro Cys Cys Asp Ala Ala Thr Cys Lys Leu Thr
 1               5                  10                  15

Thr Gly Ser Gln Cys Ala Asp Gly Leu Cys Cys Asp Gln Cys Lys Phe
            20                  25                  30

Met Lys Glu Gly Thr Val Cys Arg Arg Ala Arg Gly Asp Asp Leu Asp
        35                  40                  45

Asp Tyr Cys Asn Gly Ile Ser Ala Gly Cys Pro Arg Asn Pro Phe His
    50                  55                  60

Ala
 65

<210> SEQ ID NO 3
<211> LENGTH: 216
<212> TYPE: PRT
<213> ORGANISM: Escherichia coli
<220> FEATURE:
<221> NAME/KEY: MOD_RES
<222> LOCATION: (206)..(206)
<223> OTHER INFORMATION: Any amino acid
```

<400> SEQUENCE: 3

Asp Asp Ala Ala Ile Gln Gln Thr Leu Ala Lys Met Gly Ile Lys Ser
1               5                   10                  15

Ser Asp Ile Gln Pro Ala Pro Val Ala Gly Met Lys Thr Val Leu Thr
            20                  25                  30

Asn Ser Gly Val Leu Tyr Ile Thr Asp Asp Gly Lys His Ile Ile Gln
        35                  40                  45

Gly Pro Met Tyr Asp Val Ser Gly Thr Ala Pro Val Asn Val Thr Asn
    50                  55                  60

Lys Met Leu Leu Lys Gln Leu Asn Ala Leu Glu Lys Glu Met Ile Val
65                  70                  75                  80

Tyr Lys Ala Pro Gln Glu Lys His Val Ile Thr Val Phe Thr Asp Ile
                85                  90                  95

Thr Cys Gly Tyr Cys His Lys Leu His Glu Gln Met Ala Asp Tyr Asn
            100                 105                 110

Ala Leu Gly Ile Thr Val Arg Tyr Leu Ala Phe Pro Arg Gln Gly Leu
        115                 120                 125

Asp Ser Asp Ala Glu Lys Glu Met Lys Ala Ile Trp Cys Ala Lys Asp
    130                 135                 140

Lys Asn Lys Ala Phe Asp Asp Val Met Ala Gly Lys Ser Val Ala Pro
145                 150                 155                 160

Ala Ser Cys Asp Val Asp Ile Ala Asp His Tyr Ala Leu Gly Val Gln
                165                 170                 175

Leu Gly Val Ser Gly Thr Pro Ala Val Val Leu Ser Asn Gly Thr Leu
            180                 185                 190

Val Pro Gly Tyr Gln Pro Pro Lys Glu Met Lys Glu Phe Xaa Asp Glu
        195                 200                 205

His Gln Lys Met Thr Ser Gly Lys
    210                 215

<210> SEQ ID NO 4
<211> LENGTH: 132
<212> TYPE: PRT
<213> ORGANISM: Escherichia coli

<400> SEQUENCE: 4

Gly Leu Phe Asp Ala Pro Gly Arg Ser Gln Phe Val Pro Ala Asp Gln
1               5                   10                  15

Ala Phe Ala Phe Asp Phe Gln Gln Asn Gln His Asp Leu Asn Leu Thr
            20                  25                  30

Trp Gln Ile Lys Asp Gly Tyr Tyr Leu Tyr Arg Lys Gln Ile Arg Ile
        35                  40                  45

Thr Pro Glu His Ala Lys Ile Ala Asp Val Gln Leu Pro Gln Gly Val
    50                  55                  60

Trp His Glu Asp Glu Phe Tyr Gly Lys Ser Glu Ile Tyr Arg Asp Arg
65                  70                  75                  80

Leu Thr Leu Pro Val Thr Ile Asn Gln Ala Ser Ala Gly Ala Thr Leu
                85                  90                  95

Thr Val Thr Tyr Gln Gly Cys Ala Asp Ala Gly Phe Cys Tyr Pro Pro
            100                 105                 110

Glu Thr Lys Thr Val Pro Leu Ser Glu Val Val Ala Asn Asn Glu Ala
        115                 120                 125

Ser Gln Pro Val
    130

<210> SEQ ID NO 5
<211> LENGTH: 69
<212> TYPE: PRT
<213> ORGANISM: Agkistrodon contortrix

<400> SEQUENCE: 5

Gly Asp Ala Pro Ala Asn Pro Cys Cys Asp Ala Ala Thr Cys Lys Leu
1               5                   10                  15

Thr Thr Gly Ser Gln Cys Ala Asp Gly Leu Cys Cys Asp Gln Cys Lys
            20                  25                  30

Phe Met Lys Glu Gly Thr Val Cys Arg Arg Ala Arg Gly Asp Asp Leu
        35                  40                  45

Asp Asp Tyr Cys Asn Gly Ile Ser Ala Gly Cys Pro Arg Asn Pro His
    50                  55                  60

Lys Gly Pro Ala Thr
 65

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttccagatc tcgagaatct ttacttccaa ggagacgctc ctgcaaatcc gtgctgcgat    60
gctgca                                                              66

<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gttattcgcc atggcttagg catggaaggg atttctggga cagccagcag a             51

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttattcgcc atggcttaag tagctggacc cttgtgggga tttctgggac agccagcaga    60
tatgcc                                                              66

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accgtatgcc gtagagcaag gggtgatgac ctggatgatt ac                      42

-continued

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgctctacgg catacggttc cttctttcat aaatttgcac tg                           42

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgcgatgctg caacctgtaa actgaccacc gggtcacagt gtgcagat                     48

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagtttacag gttgcagcat cgcagcacgg atttgc                                  36

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tctgatggca gaaaaattac caccaaccct ccggttgag                               39

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14 aattttctg ccatcagagg aataatg                                             27

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catagtgcaa taaatctttg ggttgcagtt actatggccc atgag                        45

<210> SEQ ID NO 16
<211> LENGTH: 45

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atttattgca ctatgatcct gaacaattcc ggtagaaagc ttcgg            45

<210> SEQ ID NO 17
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gttccccatg gatgagaatc tttacttcca aggagacgct cctgcaaatc cgtgctgcga   60
tgctgca                                                             67

<210> SEQ ID NO 18
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gttccccatg gatgagaatc tttacttcca aggaatgatc caggttctct tggtgactct   60
atgctta                                                             67

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttattcgga attcttaggc atggaaggga tttctgggac agccagcaga            50

<210> SEQ ID NO 20
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttattcgga attcttaagt agctggaccc ttgtggggat ttctgggaca gccagcagat   60
atgcc                                                               65

<210> SEQ ID NO 21
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gttattcgga attcatatta cagaatttgg ataccatctg gaagcta              47
```

```
<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttattcgga attcgaatga gaatagtttg tttattgacg gaagcag                    47

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cccctctaga aataattttg tttaact                                          27

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tacccagatc tgggctgtcc atgtgct                                          27

<210> SEQ ID NO 25
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttctgggcag agtggtgccc gtattgcaaa atgatcgccc cg                         42

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcaccactct gcccagaaat c                                                21

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttctgggcag agtggtgcgg tcattgcaaa atgatcgccc cg                         42
```

```
<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcaccactct gcccagaaat c                                               21

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttccccatg gatgaccctg caaatccgtg ctgcgatgct gcaaca                    46

<210> SEQ ID NO 30
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gttccccatg gatgacccta tgatccaggt tctcttggtg actctatgct ta             52

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtattcatat ggatgacgcg gcaattcaac aaacgtta                             38

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gttccctcga gttatttacc gctggtcatt ttttggtg                             38

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gttattcgcc atgggattat tcgacgcgcc gggacgttca                           40

<210> SEQ ID NO 34
<211> LENGTH: 41
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtctacgaat tcgcttaagg ctgtggcgct gcgttgttgg c                          41

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tttactgata ttacctgtac cttctgccac aaactgcatg ag                         42

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tttactgata ttacctgtgg tttctgccac aaactgcatg ag                         42

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acaggtaata tcagtaaaca c                                                21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggatctcgac gctctcccatt a                                               21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttgtacacgg ccgcataatc g                                                21

<210> SEQ ID NO 40
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 40
cgattatgcg gccgtgtaca a                                              21

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggaattgtga gcggataaca attc                                           24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgcggttctg gtatgaaaga aacc                                           24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gttatgctag ttattgctca gcgg                                           24

<210> SEQ ID NO 44
<211> LENGTH: 4
<212> TYPE: PRT
<213> ORGANISM: Escherichia coli

<400> SEQUENCE: 44

Cys Gly Tyr Cys
 1

<210> SEQ ID NO 45
<211> LENGTH: 4
<212> TYPE: PRT
<213> ORGANISM: Escherichia coli

<400> SEQUENCE: 45

Cys Gly Phe Cys
 1

<210> SEQ ID NO 46
<211> LENGTH: 4
<212> TYPE: PRT
<213> ORGANISM: Escherichia coli

<400> SEQUENCE: 46

Cys Thr Phe Cys
 1
```

```
<210> SEQ ID NO 47
<211> LENGTH: 6
<212> TYPE: PRT
<213> ORGANISM: Agkistrodon contortrix

<400> SEQUENCE: 47

His Lys Gly Pro Ala Thr
 1               5

<210> SEQ ID NO 48
<211> LENGTH: 4
<212> TYPE: PRT
<213> ORGANISM: Escherichia coli

<400> SEQUENCE: 48

Cys Gly Pro Cys
 1

<210> SEQ ID NO 49
<211> LENGTH: 4
<212> TYPE: PRT
<213> ORGANISM: Escherichia coli

<400> SEQUENCE: 49

Cys Pro Tyr Cys
 1

<210> SEQ ID NO 50
<211> LENGTH: 4
<212> TYPE: PRT
<213> ORGANISM: Escherichia coli

<400> SEQUENCE: 50

Cys Gly His Cys
 1

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Gly or Ser

<400> SEQUENCE: 51

Glu Asn Leu Tyr Phe Gln Xaa
 1               5

<210> SEQ ID NO 52
<211> LENGTH: 4
<212> TYPE: PRT
<213> ORGANISM: Escherichia coli

<400> SEQUENCE: 52

Cys Pro His Cys
 1

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued

```
                peptide

<400> SEQUENCE: 53

Glu Asn Leu Tyr Phe Gln Gly
  1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Asn Leu Tyr Phe Gln Ser
  1               5

<210> SEQ ID NO 55
<211> LENGTH: 1449
<212> TYPE: DNA
<213> ORGANISM: Agkistrodon contortrix

<400> SEQUENCE: 55
atgatccagg ttctcttggt gactctatgc ttagcagctt ttccttatca agggagctct      60
ataatcctgg aatctgggaa tgttaatgat tatgaagtac tgtatccaca aaaagtcact     120
gcattgccca aggagcagt  tcagccaaag tatgaagaca ccatgcaata tgaatttaaa     180
gtgaatggag agccagtggt ccttcacctg gaaaaaaata aaggactttt ttcaaaagat     240
tacagcgaga ctcattattc ctctgatggc agaaaaatta caacaaaccc tccggttgag     300
gatcactgct attatcatgg acgcatccag aatgatgctg actcaactgc aagcatcagt     360
gcatgcaacg gtttgaaagg acatttcaag cttcaagggg agacgtacct tattgaaccc     420
ttgaagcttt ccgacagtga agcccatgca gtctacaaat atgaaaacgt agaaaaagaa     480
gatgaggccc ccaaaatgtg tgggtaacc  cagactaatt gggaatcaga tgagcccatc     540
aaaaaggcct ctcagttaaa tcttactcct gaacaacaag gattccccca agatacatt      600 gagcttgttg tagttgcaga tcacagaatg ttcacgaaat acaacggcaa tttaaatact     660
attagaatat gggtacatga acttgtcaac actatgaatg tgttttacag acctttgaat     720
attcgtgtct cactgactga cctagaagtt tggtcagacc aagatttgat caacgtgcag     780
ccagcagcgg ctgatacttt ggaagcattt ggagacttga gagacagt   cttgctgaat     840 cgcataagtc atgataatgc tcagttactc acggccattg agcttgatgg agaaactata     900
ggattggcta caggggcac  catgtgcgac ccgaagcttt ctacaggaat tgttcaggat     960
catagtgcaa taaatctttg ggttgcagtt acaatggccc atgagatggg tcataatctg    1020
ggtattagtc acgatggaaa tcagtgtcat tgcgatgcta actcatgcat tatgagtgaa    1080
gaactaagag aacaactttc ctttgagttc agcgattgta gtcagaatca atatcagaca    1140
tatcttactg atcataaccc acaatgcatg ctcaatgaac ccttgagaac agatattgtt    1200
tcaactccag tttctggaaa tgaacttttg gagacgggag aagaaagtga ctttgacgct    1260
cctgcaaatc cgtgctgcga tgctgcaaca tgtaaactga acacagggtc acagtgtgca    1320
gatggactgt gttgtgacca gtgcaaattt atgaaagaag aacagtatg  ccggagagca    1380 agggggtgatg acctggatga ttactgcaat ggcatatctg ctggctgtcc cagaaatccc    1440
ttccatgcc                                                            1449
```

```
<210> SEQ ID NO 56
<211> LENGTH: 1449
<212> TYPE: DNA
<213> ORGANISM: Agkistrodon contortrix

<400> SEQUENCE: 56
atgatccagg ttctcttggt gactctatgc ttagcagctt ttccttatca agggagctct      60
ataatcctgg aatctgggaa tgttaatgat tatgaagtac tgtatccaca aaaagtcact     120
gcattgccca aaggagcagt tcagccaaag tatgaagaca ccatgcaata tgaatttaaa     180
gtgaatggag agccagtggt ccttcacctg gaaaaaaata aaggactttt ttcaaaagat     240
tacagcgaga ctcattattc ctctgatggc agaaaaatta ccaccaaccc tccggttgag     300
gatcactgct attatcatgg acgcatccag aatgatgctg actcaactgc aagcatcagt     360
gcatgcaacg gtttgaaagg acatttcaag cttcaagggg agacgtacct tattgaaccc     420
ttgaagcttt ccgacagtga agcccatgca gtctacaaat atgaaaacgt agaaaaagaa     480
gatgaggccc ccaaaatgtg tgggtaacc cagactaatt gggaatcaga tgagcccatc      540
aaaaaggcct ctcagttaaa tcttactcct gaacaacaag gattccccca aagatacatt     600
gagcttgttg tagttgcaga tcacagaatg ttcacgaaat acaacggcaa tttaaatact     660
attagaatat gggtacatga acttgtcaac actatgaatg tgttttacag acctttgaat     720
attcgtgtct cactgactga cctagaagtt tggtcagacc aagatttgat caacgtgcag     780
ccagcagcgg ctgatacttt ggaagcattt ggagactgga gagagacagt cttgctgaat     840
cgcataagtc atgataatgc tcagttactc acggccattg agcttgatgg agaaactata     900
ggattggcta acagggcac catgtgcgac ccgaagcttt ctaccggaat tgttcaggat      960
catagtgcaa taaatctttg ggttgcagtt actatggccc atgagatggg tcataatctg    1020
ggtattagtc acgatggaaa tcagtgtcat tgcgatgcta actcatgcat tatgagtgaa    1080
gaactaagag aacaactttc ctttgagttc agcgattgta gtcagaatca atatcagaca    1140
tatcttactg atcataaccc acaatgcatg ctcaatgaac ccttgagaac agatattgtt    1200
tcaactccag tttctggaaa tgaacttttg gagacgggag aagaaagtga ctttgacgct    1260
cctgcaaatc cgtgctgcga tgctgcaacc tgtaaactga ccaccgggtc acagtgtgca    1320
gatggactgt gttgtgacca gtgcaaattt atgaaagaag gaaccgtatg ccgtagagca    1380
aggggtgatg acctggatga ttactgcaat ggcatatctg ctggctgtcc cagaaatccc    1440
ttccatgcc                                                            1449
```

INHIBITING INTEGRIN RECEPTOR BINDING WITH NON-NATIVE MONOMERIC DISINTEGRIN OR MONOMERIC DISINTEGRIN DOMAINS

CROSS REFERENCE TO RELATED PATENT APPLICATIONS

The present application is a divisional application of U.S. application Ser. No. 12/831,226 (now U.S. Pat. No. 8,110,542), filed Jul. 6, 2010, which is a continuation of U.S. application Ser. No. 11/351,311 (now U.S. Pat. No. 7,754,850) filed Feb. 9, 2006, which claims the benefit under 35 USC §119(e) of U.S. Application Ser. No. 60/652,529 filed Feb. 11, 2005, the entire contents of which including all figures and tables are incorporated herein by reference.

STATEMENT OF GOVERNMENT SUPPORT

This invention was supported in whole or in part with funding from the United States Army and the National Institutes of Health. The United States government may have certain rights in the invention.

SEQUENCE LISTING

The instant application contains a Sequence Listing which has been submitted via EFS-Web and is hereby incorporated by reference in its entirety. Said ASCII copy, created on Jan. 12, 2010, is named 75405602.txt, and is 20,658 bytes in size.

BACKGROUND OF THE INVENTION

This invention relates to methods of expressing proteins in recombinant hosts and more particularly to expressing in microbial hosts heterologous eukaryotic proteins that require formation of disulfide bridges for biological activity.

A variety of proteins are known which have commercial and medical application and which are characterized in having a complex molecular structure stabilized by disulfide bridging. One such class of the proteins, the disintegrins, include a class of cysteine-rich proteins that are the most potent known soluble ligands of integrins (Gould, Polokoff et al. 1990; Niewiarowski, McLane et al. 1994). The tri-peptide motif RGD (Arg-Gly-Asp) is conserved in most monomeric disintegrins (Niewiarowski, McLane et al. 1994). The RGD sequence is at the tip of a flexible loop, the integrin-binding loop, stabilized by disulfide bonds and protruding from the main body of the peptide chain. Disintegrins bind to the fibrinogen receptor $\alpha IIb\beta3$, which results in the inhibition of fibrinogen-dependent platelet aggregation (Savage, Marzec et al. 1990). Except for barbourin, a KGD-containing disintegrin, which is a relatively specific ligand for $\alpha IIb\beta3$ integrin (Scarborough, Rose et al. 1991), other disintegrins are rather nonspecific and can block or disturb the signaling pathways associated with the function of other $\beta3$ integrins, as well as $\beta1$ integrins (McLane, Marcinkiewicz et al. 1998).

Contortrostatin (CN) is the disintegrin isolated from *Agkistrodon contortrix contortrix* (southern copperhead) venom (Trikha, Rote et al. 1994). CN displays the classical RGD motif in its integrin-binding loop. Unlike other monomeric disintegrins, CN is a homodimer with a molecular mass (Mr) of 13,505 for the intact molecule and 6,750 for the reduced chains as shown by mass spectrometry (Trikha, Rote et al. 1994).

Receptors of CN identified so far include integrins $\alpha IIb\beta33$, $\alpha v\beta3$, $\alpha v\beta5$, and $\alpha 5\beta1$ (Trikha, De Clerck et al. 1994; Trikha, Rote et al. 1994; Zhou, Nakada et al. 1999; Zhou, Nakada et al. 2000). Interactions between CN and integrins are all RGD-dependent. As an anti-cancer agent, CN has shown to be a powerful anti-angiogenic and anti-metastatic molecule in in vitro cell-based functional assays and in vivo animal models (Trikha, De Clerck et al. 1994; Trikha, Rote et al. 1994; Schmitmeier, Markland et al. 2000; Zhou, Hu et al. 2000; Markland, Shieh et al. 2001; Swenson, Costa et al. 2004). CN also has the ability to directly engage tumor cells and suppress their growth in a cytostatic manner (Trikha, De Clerck et al. 1994; Trikha, Rote et al. 1994; Schmitmeier, Markland et al. 2000). The antitumoral activity of CN is based on its high affinity interaction with integrins $\alpha 5\beta1$, $\alpha v\beta3$ and $\alpha v\beta5$ on both cancer cells and newly growing vascular endothelial cells (Trikha, De Clerck et al. 1994; Zhou, Nakada et al. 1999; Zhou, Nakada et al. 2000; Zhou, Sherwin et al. 2000). This diverse mechanism of action provides CN with a distinct advantage over many antiangiogenic agents that only block a single angiogenic pathway and/or do not directly target tumor cells.

CN full-length DNA precursor has been cloned and sequenced (Zhou, Hu et al. 2000). CN is produced in the snake venom gland as a multidomain precursor of 2027 bp having a 1449 bp open reading frame (encoding proprotein, metalloproteinase and disintegrin domains), which is proteolytically processed, possibly autocatalytically, to generate mature CN. The CN disintegrin domain encodes 65 amino acids with a molecular weight equal to that of the CN subunit. The CN full-length precursor mRNA sequence can be accessed in the GeneBank database using accession number: AF212305. The nucleotide sequence encoding the 65 amino acid disintegrin domain of CN represents the segment from 1339 to 1533 in the mRNA. Plasmids encoding the CN full-length gene have been described (Zhou, Hu et al. 2000) and are available from the laboratory of Francis S. Markland at University of Southern California.

Structurally, CN is a cysteine-rich protein (10 cysteines per monomer) that displays no secondary structure and, like other disintegrins, has a complex folding pattern that relies on multiple disulfide bonds (four intrachain and two interchain disulfide bonds) to stabilize its tertiary structure (Zhou, Hu et al. 2000). By folding in a compact structure locked by multiple disulfide bonds, CN, like many other venom proteins, has a survival advantage, being less susceptible to a proteolytic attack and better equipped to survive in the harsher extracellular microenvironment. Its highly cross-linked structure and unique biological activity are barriers to producing biologically functional CN (or other disintegrin domain protein) using a recombinant expression system. A further difficulty is that the CN disintegrin domain of the multidomain precursor, from which dimeric CN is derived, displays no secondary structure, a feature that is known to facilitate the proper folding in most nascent proteins (Moiseeva, Swenson et al. 2002). The crystal structure of native CN has not been elucidated. CN's folding pattern is presumably as complex as other viperid dimeric disintegrins that have been studied (Calvete, Jurgens et al. 2000; Bilgrami, Tomar et al. 2004). Attempts to express snake venom disintegrins such as CN as functional native conformers and at a high level of expression suitable for mass production in eukaryotic and prokaryotic systems have been so far disappointing (e.g., see (Moura-da-Silva, Linica et al. 1999).

SUMMARY OF THE INVENTION

Provided are methods of expressing in prokaryotic hosts eukaryotic proteins, particularly for eukaryotic proteins that have multiple disulfide bridges. The methods are particularly suitable for expressing the eukaryotic proteins where a biologically activity is dependent on the formation of the one or more disulfide bridges (intra and interchain). In some cases, the method is applicable to expressing active eukaryotic proteins that require formation of multiple disulfide bridges (intra and interchain) and form little to no secondary structure.

In one approach, expression of a eukaryotic protein in host cells is achieved by expressing the protein as a genetic fusion with a fusion partner. The fusion partner may be a bacterial thioredoxin such as thioredoxin A (TrxA). This is achieved by cloning DNA sequence encoding the eukaryotic protein downstream (i.e. 3') to sequence encoding the thioredoxin. Sequence encoding the fusion protein may be contained within a suitable expression vector under control of appropriate regulatory control sequences such as a promoter, optional enhancer, repressor, and the like. In one embodiment, the vector is pET32a. In another embodiment the vector is the pET32a/pCDFDuet-1 combination. Host cells transformed with the expression vector encoding the thioredoxin/eukaryotic protein are cultured to produce the fusion protein containing the eukaryotic protein.

In still yet another embodiment, the prokaryotic host cells are engineered to cytoplasmically express a disulfide isomerase normally targeted to the periplasmic space in bacteria. In one embodiment, the disulfide isomerase is DsbC. In another embodiment, the cells are engineered to cytoplasmically express a redox catalyst such as the α-domain of the bacterial thiol-disulfide interchange protein DsbD. Cytoplasmic localization of DsbC or the α-domain of DsbD can be achieved by expressing the mature protein without a signal sequence. The host cells also may be modified to cytoplasmically express both DsbC and the α-domain of the DsbD.

In further embodiments, active site mutants of a disulfide isomerase with increased isomerase activity can be expressed cytoplasmically by the host cells in place of the wild type isomerase. For example, the active site of wild type DsbC in *E. coli* in which the sequence CGYC (SEQ ID NO: 44) is replaced with CGFC (SEQ ID NO: 45) or CTFC (SEQ ID NO: 46) results in a mutant enzyme with increased isomerase activity.

In another embodiment, the host cell may have a mutant trxB gene and/or a mutant gor gene, rendering the cell deficient in thioredoxin reductase activity and/or glutathione reductase activity. These mutations may be used separately or in combination with any other host cells variations described herein.

In a further embodiment, the host cells are made deficient in one or more proteases. Exemplary such proteases include those encoded by ompT and lon genes. For example, *E. coli* host cells AD494(DE3)pLysS are deficient in trxB gene as well as ompT and ion. *E. coli* strain Origami B(DE3)pLysS and Rosetta-gami B(DE3)pLysS are deficient in trxB, gor, ompT and ion gene products. These mutations may be used in combination with any other host cells variations described herein. Thus, the ompT and lon mutations may be used in combination with host cells deficient in trxB and/or gor as well as host cells modified to cytoplasmically express DsbC (wild type protein or active site mutant) and/or the DsbD α-domain.

Eukaryotic proteins expressed by the methods disclosed herein include those where a biological activity is dependent on the formation of at least one disulfide bridge. In another embodiment, a biological activity of the eukaryotic protein is dependent on the formation of at least two disulfide bridges. In yet another embodiment, a biological activity of the eukaryotic protein is dependent on the formation of at least three disulfide bridges. In a further embodiment, a biological activity of the eukaryotic protein is dependent on the formation of at least four disulfide bridges. In yet a further embodiment, a biological activity of the eukaryotic protein is dependent on the formation of at least five disulfide bridges. In yet a further embodiment, a biological activity of the eukaryotic protein is dependent on the formation of at least 10 disulfide bridges or at least 15 disulfide bridges.

As used herein, the term "eukaryotic protein" refers to a protein that is expressed naturally by a eukaryotic cell. The term eukaryotic protein also includes variations in the amino acid sequence of the naturally expressed eukaryotic protein provided that the protein retains at least one activity associated with the naturally expressed eukaryotic protein and the sequence of the eukaryotic protein is different from any procaryotic protein. In preferred embodiments, eukaryotic proteins are expressed as described herein so that they retain at least one activity or function characteristic with the native protein. Preferably, the expressed proteins retain all or substantially of the activity or functions of the native protein. In other preferred embodiments, the expressed protein retain at least one activity or function characteristic with the native protein which activity or function is dependent on the formation of at least one or more disulfide bridges. The term "substantially" as used herein means plus or minus 10% unless otherwise indicated.

The activity or function of a protein (i.e. its biological activity) reflects characteristics of the protein that result from its primary amino acid sequence and/or secondary and/or tertiary structure. For example, the biological activity of an eukaryotic enzyme includes the ability to catalyze a specific enzymatic reaction. The biological activity of a structural eukaryotic protein may include the ability of such protein to form appropriate subcellular structures in cells. Methods of assessing biological activity are well known in the art Eukaryotic proteins that can be expressed as described herein include monomeric or multimeric (e.g. dimeric) proteins and proteins from different classes such as ADAM proteins, disintegrins, toxins, vaccine components including bacterial or viral proteins, matrix metalloproteases (MMPs), immunoglobulins including antibodies and the T cell receptor extracellular domain, adhesive proteins belonging to the immunoglobulin superfamily of cell adhesion molecules (Ig-CAMs), cytokines, chemokines, interferons, growth factors, and plasminogen activators. Exemplary proteins include contortrostatin, jararhagin, disintegrin schistatin, snake metalloproteinase fibrolase, human interleukin-2 precursor, human interferon-γ, human transforming growth factor beta 2, human liver expression chemokine (LEC, CCL16), omega-conotoxin CVID precursor, scorpion chlorotoxin, human ADAM 9 precursor, human vascular endothelial factor A (VEGF-A), and human tissue-type plasminogen activator precursor (t-PA).

Active fragments of a eukaryotic protein also may be expressed using the invention methods. For example, in the case of snake venom disintegrin precursors (e.g. classes PII and PIII), which are multidomain proteins that include several biologically active domains (metalloprotease, disintegrin, disintegrin-like and/or cysteine-rich), the expressed product may be the full length preprotein (the full length precursor), or a biologically active fragment represented by the following possibilities: a metalloprotease domain, a disintegrin domain, a disintegrin-like domain, and a cysteine-rich domain either alone or combinations with the other domains (e.g. disintegrin and cysteine-rich domains expressed together). Other fragments of disintegrins also are possible. Other fragments are possible. In the case of an antibody, exemplary fragments include the F(ab')2 fragment, the Fab fragment, the Fv or single chain Fv fragments and the Fc fragment. Other antibody fragments also are possible.

In one embodiment, a cleavage site is engineered between thioredoxin and the eukaryotic protein to enable isolation of the eukaryotic protein from the fusion protein following expression. In another embodiment, the cleavage site is a proteolytic cleavage site. In another embodiment, the cleavage site is a chemical cleavage site. The cleavage site is preferably placed between the thioredoxin and the eukaryotic protein (e.g. downstream of the thioredoxin sequence and upstream of the N-terminal end of the disulfide containing eukaryotic protein) in order to obtain the eukaryotic protein free from thioredoxin.

In one embodiment, the expressed fusion protein with internal cleavage site may be substantially purified from other contaminating molecules. To assist in purification, the fusion protein may include a sequence encoding a ligand or receptor or a sequence of amino acids capable of coordinating a metal ion (i.e. a tag). The tag sequence may be any member of a ligand/receptor pair that is peptide in nature. In one embodiment, the tag sequence includes a His-tag (poly His) sequence. The tag sequence is preferably located at the N-terminal or C-terminal and more preferably N-terminal to disulfide containing eukaryotic protein and upstream of any cleavage site.

The disulfide containing eukaryotic protein expressed by the methods herein may include functionally useful sequences that are taken or modeled from other proteins of the same structural class. These functional sequences, non-native to the eukaryotic protein, may be located at either terminus of the eukaryotic protein or within the eukaryotic protein as dictated by the effect of the addition on the biological function of the eukaryotic protein. Such functional sequences include the amino acid residues located downstream from the most C-terminal Cys residue in mono- or dimeric disintegrin primary sequences. For example, a biologically active disintegrin domain may include sequence at its C-terminus that directs binding to a particular type of integrin. For example, the CN full-length disintegrin precursor or its disintegrin domain may be expressed with the C-terminal extension, HKGPAT (three letter code: His-Lys-Gly-Pro-Ala-Thr) (SEQ ID NO: 47), which represents the C-terminal amino acid sequence of echistatin, a disintegrin which is monomeric in its native state. The addition of the HKGPAT (SEQ ID NO: 47) at the C-terminus of CN can be used to increase the affinity of the expressed recombinant CN disintegrin domain for $\alpha5\beta1$ integrin. This C-terminal fusion also can facilitate the proper folding of nascent recombinant CN disintegrin domain in the C-terminal half of the molecule, wherein the integrin-binding loop key structural element resides.

In yet a further embodiment, the disulfide containing eukaryotic protein is a disintegrin, which may be expressed as a chimeric fusion protein with the sequence HKGPAT (SEQ ID NO: 47) at the C-terminal end. A fusion protein that includes a contortrostatin domain N-terminal to the sequence HKGPAT (SEQ ID NO: 47) is referred to as vicrostatin (VN).

In further embodiments, codon usage for nucleotide sequence encoding the eukaryotic protein may be optimized for expression in a particular host. For example, E. coli codon usage can be manipulated so as to optimize expression of disintegrins by supplementing the expression host's tRNA production with tRNA species encoded by engineered plasmids employed to transform such expression hosts. Codon usage may also be optimized for a thioredoxin or a disulfide isomerase encoding sequence which is non-native to the host cell by selecting codons more appropriate to the host cells.

In a further approach, the eukaryotic protein may be directly expressed without the upstream thioredoxin sequence. The eukaryotic protein may contain additional sequence as discussed above. The host cells which are transformed with a vector encoding the eukaryotic protein not fused to thioredoxin may have any combination of the modifications discussed above.

In accordance with any of the above methods, a level of expression of the fusion protein containing the eukaryotic protein is at least 1-3 mg/L, more preferably 4-6 mg/L, even more preferably 7-9 mg/L, yet even more preferably 8-10 mg/L or more, 11-14 mg/L or more, 15-19 mg/L or more, or 20 mg/L or more.

Also provided is a substantially purified eukaryotic protein (fused to thioredoxin or separated from thioredoxin) produced by any of the method described herein.

Further provided is a fusion protein which comprises an N-terminal segment encoding thioredoxin and a C-terminal segment encoding a eukaryotic protein that requires formation of at least two intrachain or interchain disulfide bridges for biological activity. Preferably, the eukaryotic protein includes a disintegrin. The fusion protein may be cleaved to yield the eukaryotic protein substantially purified from the thioredoxin. The fusion protein may be substantially purified.

Still further provided is a composition comprising the produced eukaryotic protein (or fusion protein) and prokaryotic material. Prokaryotic material in the composition may be derived from the prokaryotic cell used as the expression host. Prokaryotic material as used herein refers to protein, lipoprotein, lipid, nucleic acid, carbohydrate or any other molecule that is present in a prokaryotic cell but is absent from or different from what is present in a eukaryotic cell.

Additionally provided are expression vectors and prokaryotic host cells containing such expression vectors obtained by any of the methods described herein. For example, provided is an expression vector that contains an expression cassette that encodes thioredoxin fused to a disintegrin or disintegrin domain, and host cells transformed with such an expression vector.

Also provided is a monomeric disintegrin or monomeric disintegrin domain which comprises a C-terminal sequence non-native to the disintegrin or disintegrin domain, the C-terminal sequence encoding a functional integrin-binding loop. In one embodiment, integrin binding loop is selected from any of integrin $\alpha IIb\beta3$, $\alpha v\beta3$, $\alpha v\beta5$, or $\alpha5\beta1$. In another embodiment, the integrin binding loop C-terminal sequence comprises HKGPAT (SEQ ID NO: 47). In a further embodiment, the integrin binding loop is stabilized by at least one intramolecular disulfide bridge. In yet another embodiment, the monomeric disintegrin or monomeric disintegrin domain is from contortrostatin. The monomeric disintegrin or monomeric disintegrin domain may be obtained by expressing in host cells as described above. Following expression, the monomeric disintegrin or monomeric disintegrin domain may be obtained in substantially purified form.

Additionally provided are methods of inhibiting binding between a cell expressing integrin receptors specific for one or more integrins selected from the group consisting of $\alpha IIb\beta3$, $\alpha v\beta3$, $\alpha v\beta5$, or $\alpha5\beta1$ and, and one or more integrins selected from the group consisting of $\alpha IIb\beta3$, $\alpha v\beta3$, $\alpha v\beta5$, or $\alpha5\beta1$, the method comprising contacting the cell with a monomeric disintegrin or a monomeric disintegrin domain which comprises a C-terminal sequence non-native to the disintegrin or disintegrin domain, said C-terminal sequence encoding a functional integrin-binding loop. In a preferred embodiment, the integrin receptor is the vitronectin receptor.

Still further provided are methods of inhibiting in vivo platelet aggregation, cell growth, cell adhesion, metastasis, or neovascularization, the method comprising administering to an individual in need of such treatment an effective amount of a monomeric disintegrin or a monomeric disintegrin domain which comprises a C-terminal sequence non-native to the disintegrin or disintegrin domain, said C-terminal sequence encoding a functional integrin-binding loop.

BRIEF DESCRIPTION OF THE FIGURES

FIG. 7 shows the putative trimestatin-receptor interaction after docking trimestatin monomeric disintegrin into integrin αvβ3 binding pocket (from Fujii, Okuda et al. 2003).

FIG. 14 A shows a representative section of each treatment group stained for CD34 (brown color).

FIGS. 14A and 14B show MALDI-TOF mass spectrometry of native CN and VN, respectively. A single peak of Mr of 7143.41 for VN shows that it is monomeric.

FIGS. 15A and 15B show electron spray ionization (ESI) mass spectrometry of native CN and VN, respectively. A large peak of 13507.0 in 13C for CN indicates a dimer while the single peak of 7146.0, for VN indicates a monomer.

FIG. 16 is a chart summarizing codon usage in *E. coli* (from Guerdoux-Jamet, Henaut et al. 1977).

FIG. 17 is a chart showing the eight least used codons in various organisms (from Guerdoux-Jamet, Henaut et al. 1977).

FIG. 18A shows wild type CN gene sequence (SEQ ID NO: 55) with the rarely used codons in bacteria shown in bold.

FIG. 18B shows a mutated CN gene sequence (SEQ ID NO: 56) after replacing all CGG and most ACA rarely used codons. The ACA codons left unreplaced are highlighted in bold.

DETAILED DESCRIPTION OF THE INVENTION

Figure 1:
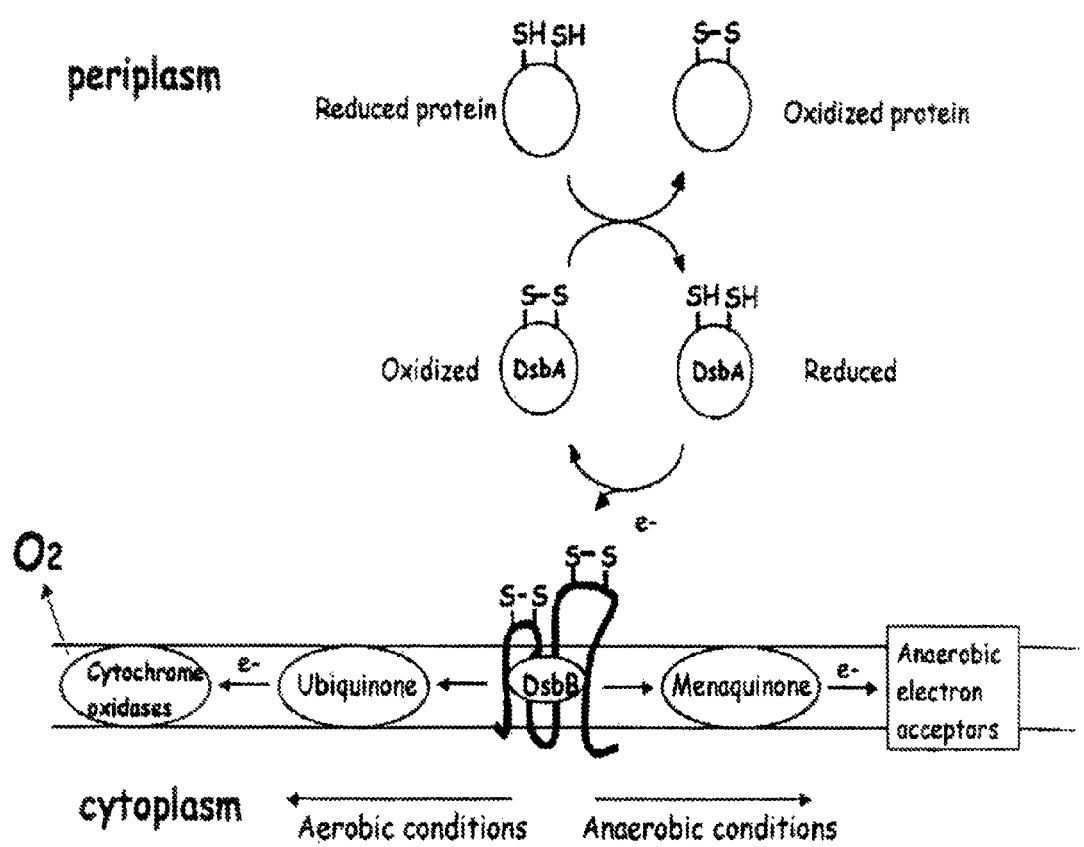
FIG. 1 depicts the oxidation pathway in *E. coli* periplasm (from Collet and Barwell 2002).

Methods of expressing in microbial hosts heterologous eukaryotic proteins that require formation of disulfide bridges for biological activity are provided. The methods are particularly suitable to expressing biologically active eukaryotic proteins that require formation of multiple disulfide bridges (intra and interchain), including such proteins which form little to no secondary structure.

In one approach, the eukaryotic protein is expressed as a fusion to a thioredoxin. As used herein, "thioredoxin" refers to a family of small (about 13 kD) electron carrier proteins with a dithiol/disulfide active site (CGPC) (SEQ ID NO: 48), which are the major cellular protein disulfide reductases which serve as electron donors for enzymes such as ribonucleotide reductases, thioredoxin peroxidases (peroxiredoxins) and methionine sulfoxide reductases. In bacteria, the redox potential of thioredoxin is maintained by thioredoxin reductase (thioredoxin B, TrxB).

Active site mutants of thioredoxin may be used in place of wild type thioredoxin in the fusion protein. Thus, thioredoxin active-site motif CXXC can be replaced with an active-site motif from another oxido-reductase. For example, active site mutants of wild type thioredoxin A may be used in place of wild type thioredoxin in the fusion construct with the eukaryotic protein. In this regard, thioredoxin A's active site motif CGPC (SEQ ID NO: 48) may be replaced with the active site motif CPYC (SEQ ID NO: 49), taken from another bacterial oxido-reductase, glutaredoxin A (also called glutaredoxin 1). This mutant may be referred to as a glutaredoxin-like thioredoxin. Another thioredoxin active site mutant is the PDI-like thioredoxin, generated by replacing the active site wild type motif CGPC (SEQ ID NO: 48) with the active site motif CGHC (SEQ ID NO: 50), taken from eukaryotic protein disulfide isomerase (PDI).

MSDKIIHLTDDSFDTDVLKADGAILVDFWAEW CGPCKMIAPILDEIADEYQGK LTVAKLNIDQN-PGTAPKYGIRGIPTLLLFKNGEVAATKV-GALSKGQLKEFLDAN LA (SEQ ID NO: 1).

In addition to full-length thioredoxin A, shorter segments may be used as the fusion with the eukaryotic protein.

Thioredoxin that is used in the fusion protein is preferably from the same type of host that is to be used for expression. For example, the encoded thioredoxin portion of the fusion protein is preferably from a particular bacterial host if that particular bacterial host is contemplated as the expression host.

Eukaryotic proteins that may be expressed by the methods herein encompass a wide range of disulfide bridge-containing proteins including monomeric and multimeric disintegrins, snake venom toxins (PI, PII or PIII class), antibody fragments (in scFv, Fab, or F(ab')2 formats), cytokines, chemokines, interferons, tumor growth factors, scorpion toxins, conotoxins, various domains of ADAM (A Disintegrin and A Metalloprotease) proteins, vaccines, growth factors, plasminogen activators, and combinations of the afore-mentioned proteins belonging to different classes and expressed as fusion proteins (for example a chemokine fused to a disintegrin etc), as well as other bio-active eukaryotic cysteine-rich proteins (e.g. jararhagin-C—GeneBank accession number AAB30855; disintegrin schistatin—GeneBank accession number P83658; snake metalloproteinase fibrolase—GeneBank accession number P83255; human interleukin-2 precursor—GeneBank accession number NP000577; human interferon-γ—GeneBank accession number NP000610; human transforming growth factor, beta 2—GeneBank accession number NP003229; human liver expression chemokine, CCL16—GeneBank accession number O15467; omega-conotoxin CVID precursor—GeneBank accession number P58920; scorpion chlorotoxin—GeneBank accession number P45639; human ADAM 9 precursor—GeneBank accession number Q13443; human vascular endothelial factor A, VEGF-A—GeneBank accession number P15692; human tissue-type plasminogen activator precursor, t-PA—GeneBank accession number P00750) etc.

As used herein "ADAM" (a disintegrin and a metalloprotease) is a family of transmembrane eukaryotic proteins that contain several different domains including a disintegrin domain and a metalloprotease domain.

As used herein, "disintegrin" refers to a class of cysteine-rich proteins that are potent soluble ligands of integrins and which are involved in regulating many processes such as cell-cell and cell-extracellular matrix adhesion, migration and invasion, cell cycle progression, differentiation and cell type specification during development of many metazoan organisms, and cell death and apoptosis. The tri-peptide motif RGD (Arg-Gly-Asp) is conserved in most monomeric disintegrins and is located at the tip of a flexible loop, the integrin-binding loop, which is stabilized by disulfide bonds and protruding from the main body of the peptide chain. All disintegrins purified from snake venoms bind to the fibrinogen receptor, integrin αIIbβ3, the binding of which results in the inhibition of fibrinogen-dependent platelet aggregation. Most disintegrins also bind to integrins αvβ3 (a vitronectin receptor) and α5β1 (a fibronectin receptor) in an RGD-dependent manner.

Most disintegrin domains of disintegrin proteins are structurally designed in a way that enables them to establish deep and extensive contacts with the integrin binding pocked that is created between the α-subunit β-propeller and β-subunit I-like domain displaying the crucial MIDAS (metal ion-dependent adhesion site) site that that coordinates the negatively charged Asp residue in the RGD tripeptide motif. Besides the flexible integrin-binding loop, disintegrins display other unique structural elements that have been shown to engage binding pockets adjacent to MIDAS in the integrin receptor. These additional structural elements contribute to the strength of interaction between the disintegrin and its receptor. One such structural element is located in the C-terminal end of disintegrins.

Figure 8:
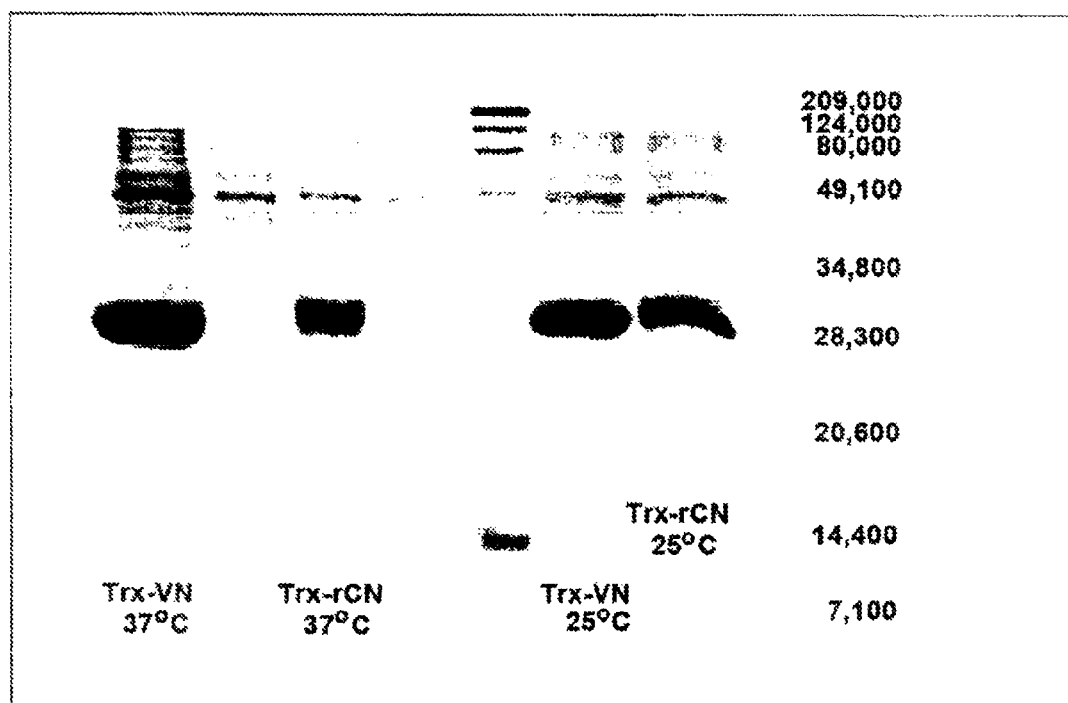
FIG. 8 depicts an SDS-PAGE Coomassie stained gel of soluble total protein fractions (TPF) collected from Origami B (DE3)pLysS *E. coli* host transformed with various Trx fusion constructs. Transformed and un-transformed Origami B *E. coli* in 1 L culture were induced with 1 mM IPTG and grown at 37° C. or 25° C. in shaken flasks at 250 rpm for 3 hours. Soluble total protein fractions (TPF) were collected in 4 ml of 20 mM Tris-HCl, pH 7.5, of which 101 were loaded and analyzed under non-reducing conditions. Lanes from the left to right: TPF from Trx-VN-expessing cells grown and induced at 37° C., TPF from non-transformed cells grown and induced at 37° C., TPF from Trx-rCN-expressing cells grown and induced at 37° C., TPF from non-transformed cells grown and induced at 25° C., broad-rage prestained protein standards (Bio-Rad), TPF from Trx-VN-expressing cells grown and induced at 25° C., and TPF from Trx-rCN-expressing cells grown and induced at 25° C.

The C-terminal tail of disintegrins stabilizes the integrin-binding loop of disintegrins so that it can interact with the binding pocked of its eukaryotic integrin. For this reason, the disintegrins make better ligands than cyclic RGD peptides and should outperform the latter as therapeutic agents. New structural studies suggest that the disintegrin integrin-binding loop of disintegrins comes into close contact with its C-terminal tail, folding together as a functional unit, and that the latter assists the integrin-binding loop in the binding pocket by making additional contacts (Fujii, Okuda et al. 2003). A putative trimestatin-receptor interaction after docking trimestatin into integrin αvβ3 binding pocket is shown in FIG. 8 (from Fujii, Okuda et al. 2003). The C-terminal tail of some disintegrins displays one or more key negatively charged residues that may be coordinated to additional binding pockets, the AMIDAS (additional metal ion-dependent adhesion site) found on the surface of the β-integrin subunit.

As used herein, "contortrostatin" (CN) refers to a disintegrin isolated from *Agkistrodon contortrix contortrix* (southern copperhead) venom (Trikha, Rote et al. 1994). CN is produced in the snake venom gland as a multidomain precursor of 2027 bp having a 1449 bp open reading frame encoding the proprotein, metalloproteinase and disintegrin domains. The precursor is proteolytically processed, possibly autocatalytically, to generate mature CN. The full length CN preprotein is encoded by the nucleotide sequence 85-1536 of the full length mRNA (GeneBank AF212305), whereas the disintegrin domain of CN represents 1339-1533 of the mRNA. The CN disintegrin domain, which contains 65 amino acids, is shown below with the RGD sequence underlined.

DAPANPCCDAATCKLTTGSQCADG-LCCDQCKFMKEGTVCRRARGDDLDDYC NGIS-AGCPRNPFHA (SEQ ID NO: 2).

Mature CN includes two 65aa disintegrin domains linked together by 2 disulfide bridges. Based on structural data from other homodimeric disintegrins (Bilgrami, Tomar et al. 2004), it is believed that the first and the third Cys residues of both 65aa subunits pair to form two interchain disulfide bridges in an antiparallel fashion (the first Cys residue of one subunit pairs with the third one of the other subunit and vice versa).

CN displays the classical tripeptide RGD motif in its integrin-binding loop. Unlike other monomeric disintegrins from crotalid venoms, CN is a homodimer with a molecular mass (Mr) of 13,505 for the intact molecule and 6,750 for the reduced chains as shown by mass spectrometry (Trikha, Rote et al. 1994).

Host cells transformed with the expression vector encoding the thioredoxin/eukaryotic protein are cultured to produce the fusion protein containing the eukaryotic protein in biologically active form. The expressed protein may be obtained directly from cells in a soluble form by routine cell lysis methods, from which it can be isolated in substantially pure form by routine purification methods.

As used herein, the term "purified" in reference to polypeptides (or proteins) does not require absolute purity. Instead, it represents an indication that the polypeptide(s) of interest is(are) in an environment in which the protein is more abundant (on a mass basis) than the environment from which the protein was initially produced. Purified polypeptides may be obtained by a number of methods including, for example, chromatography, preparative electrophoresis, centrifugation, precipitation, affinity purification, etc. The degree of purity is preferably at least 10%. One or more "substantially purified" polypeptides are at least 50% of the protein content of the environment, more preferably at least 75% of the protein content of the environment, and most preferably at least 95% of the protein content of the environment. Protein content may be determined using a modification of the method of Lowry et al. (Lowry, Rosebrough et al. 1951), described by Hartree (Hartree 1972), using bovine serum albumin as a protein standard.

In accordance with the methods herein, a cleavage site may be designed between the N-terminal thioredoxin sequence and the C-terminal containing the eukaryotic protein sequence in order to obtain the eukaryotic protein free from thioredoxin. The fusion protein may be purified prior to any cleavage step. Any number of well known cleavage sites may be used for this purpose. A suitable protease cleavage site is the TEV protease cleavage site, which comprises the amino acid sequence ENLYFQG/S (three letter code: Glu-Asn-Leu-Tyr-Phe-Gln-Gly/Ser) (SEQ ID NO: 51). The TEV site may be engineered just upstream of the N-terminus of the disulfide containing eukaryotic protein. A chemical cleavage site also may be used for this purpose. For example, a DP (Asp-Pro) dipeptide sequence can be engineered in a similar location to that of the TEV site in the fusion protein. Formic acid hydrolysis can then be used to cleave the protein at the DP site.

In some embodiments, the construct consists of a thioredoxin fused to the eukaryotic protein and a "tag" sequence to assist in detection of the fusion protein or in purification of the fusion protein or in purification of the eukaryotic protein following expression. A tag sequence can be a His-tag or poly His sequence or any sequence of amino acids that can coordinate a metal ion. The tag sequence also can be any part of a ligand/receptor binding relationship (e.g. antibody and peptide antigen). The tag sequence may be engineered into the fusion protein at the N-terminus, C-terminus or anywhere in between as dictated by constraints on the function of the expression system and the eukaryotic protein. The tag sequence is preferably upstream of any cleavage site in the fusion protein.

In accordance with the invention methods, sequence encoding the fusion protein is contained within a suitable expression vector under control of appropriate regulatory control sequences such as a promoter, optional enhancer, repressor, and the like. Suitable expression vectors for foreign protein expression in a microbial host are well known in the art. In one embodiment, the vector is pET32a. In another embodiment the vector is the pET32a/pCDFDuet-1 combination.

In another embodiment, bacterial host cells may be engineered to cytoplasmically express a disulfide isomerase normally targeted to the periplasmic space of the host. In one embodiment, the disulfide isomerase is DsbC. As used herein, "disulfide isomerase" refers to a prokaryotic protein which rearranges incorrect disulfide bonds during oxidative protein folding. DsbC is specifically activated by the periplasmic N-terminal domain (DsbD α-domain) of the transmembrane electron transporter DsbD. In the bacterial periplasm, the formation of protein disulfide bonds is catalyzed by DsbA and DsbC. DsbA is a monomer that is maintained in a fully oxidized state by the membrane enzyme DsbB, whereas DsbC is a dimer that is kept reduced by a different membrane protein, DsbD. Although the catalytic regions of DsbA and DsbC are composed of structurally homologous thioredoxin motif domains, DsbA serves only as an oxidase in vivo, whereas DsbC catalyzes disulfide reduction and isomerization and also exhibits significant chaperone activity.

Cytoplasmic localization of DsbC can be achieved by expressing the mature protein without a signal sequence. The sequence of E. coli DsbC is shown below without the signal sequence and with the active site CGYC (SEQ ID NO: 44) underlined and bolded.

DDAAIQQTLAKMGIKSSDIQPAPVAGMK-
   TVLTNSGVLYITDDGKHIIQGPMYDV SGTAPVN-
   VTNKMLLKQLNALEKEMIVYKAPQEKH-
   VITVFTDITCGYCHKLHEQ
   MADYNAL<u>GITVRY</u>LAFPRQGLDS-
   DAEKEMKAIWCAKDKNKAFDDVMAGKSV
   APASCDVDIADHYALGVQLGVSGTPAVV-
   LSNGTLVPGYQPPKEMKEFXDEHQ KMTSGK
   (SEQ ID NO: 3)

In further embodiments, active site mutants of the disulfide isomerase with increased isomerase activity can be used in place of the wild type sequence. For example, the DsbC active site CGYC (SEQ ID NO: 44) can be replaced with CGFC (SEQ ID NO: 45) or CTFC (SEQ ID NO: 46) for greater isomerase activity. Expression of signal sequenceless DsbC (or active site mutants) may be employed in host cells that are trxB and/or gor deficient. Double-mutant strain FA113 and its derivatives with both trxB and gor mutations can be used for this purpose.

In another embodiment, the host cells can be engineered to cytoplasmically express the α-domain of bacterial thiol-disulfide interchange protein DsbD (DsbD α-domain). As used herein, "DsbD" is a transmembrane E. coli enzyme that is normally targeted to the inner periplasmic membrane, with the α-domain facing the periplasmic space where it acts as a disulfide interchange catalyst (redox catalyst). Cytoplasmic localization of DsbD is achieved by expressing the domain without any signal sequence. Expression of the DsbD α-domain cytoplasmically may be combined with host cells which are trxB and/or gor deficient and which may express DsbC (signal-sequenceless wild type enzyme or an active site mutant). The DsbD α-domain represents the first 132 amino acids of mature DsbD from which a cleavable signal sequence of 19 aa is removed. The sequence of the DsbD α-domain without the leader sequence and with the catalytic site underlined is shown below.

GLFDAPGRSQFVPADQAFAFDFQQNQH-
   DLNLTWQIKDGYYLYRKQIRITPEHA KIAD-
   VQLPQGVWHEDEFYGKSEIYRDRLTLPV-

TINQASAGATLTVTYQG CADAGFCYPPETKTVPLSEVVANNEASQPV (SEQ ID NO: 4)

The DsbD α-domain without its leader sequence is designated ΔssDsbD α-domain. Host cells may be modified to cytoplasmically express DsbC and the α-domain of the DsbD.

In another embodiment, host cells are modified to be deficient in thioredoxin reductase and/or glutathione reductase activity. Thioredoxin reductase (thioredoxin B, TrxB) is a key E. coli enzyme that controls the first of the two major reductive pathways in the cytosol. A deficiency in thioredoxin reductase can be achieved by expressing a transdominant negative mutant product of the trxB gene from a separate plasmid in host's cytoplasm. Glutathione reductase (Gor) is another key enzyme that controls the second major reductive pathway in the cytosol. A deficiency in glutathione reductase can be achieved by expression of a transdominant negative mutant product of the gor gene from the same or a separate plasmid in host's cytoplasm. These mutations may be used together or alone and may be combined with any other host cells variations described herein.

In a further embodiment, host cells are deficient in one or more proteases. Exemplary such proteases include those encoded by ompT and lon genes. For example, E. coli host cells AD494(DE3)pLysS are deficient in trxB gene as well as ompT and lon gene products. E. coli strain Origami B(DE3) pLysS and Rosetta-gami B(DE3)pLysS are deficient in trxB, gor, ompT and lon gene products. These mutations may be used in combination with any other host cells variations described herein. Thus, the ompT and lon mutations may be used in combination with host cells deficient in trxB and/or gor as well as host cells modified to cytoplasmically express DsbC (wild type protein or active site mutant) and/or the DsbD α-domain.

Additional description of the methods of the invention follows.

A. Oxidative Protein Folding in Bacteria

During synthesis, the nascent polypeptide chain must fold into a unique stabilized three-dimensional structure for biological activity. In the process of generating active conformers, proteins are assisted by molecular chaperones that protect them from associating prematurely and forming insoluble aggregates. Moreover, folding catalysts (foldases) act to accelerate the rate-limiting steps in the folding pathway. The formation of correct disulfide bonds between cysteine residues in nascent proteins is a rate limiting step. The minimal enzymatic equipment needed to speed disulfide bond formation includes oxidase and isomerase activities (Collet and Bardwell 2002). In all cellular systems (from prokaryotes to eukaryotes), proteins that are destined for export into the extracellular space often exhibit multiple disulfide bonds with complex folding patterns. Having multiple disulfide bridges stabilizes the secondary and tertiary structures of these secreted proteins, conferring a survival advantage in the harsher microenvironment outside the intracellular compartment.

Cells have developed a unique enzymatic equipment to insure proper folding of multiple disulfide bond proteins because incorrect disulfide bond formation is likely to yield inactive and insoluble products (Walker and Gilbert 1994). In eukaryotes, disulfide bond formation and isomerization is catalyzed by protein disulfide isomerase (PDI) and related proteins and takes place in the endoplasmic reticulum. More than a decade ago, it was discovered that disulfide bond formation in the prokaryotic periplasmic space is also a catalyzed process (Bardwell, McGovern et al. 1991). As in the case of other organisms such as bacteria, proteins that are cysteine-rich and whose folding is dependent on correct disulfide-bridge formation primarily those destined for extracellular secretion. These proteins are usually important to cell survival and are involved in: key components of the locomotor apparatus, the respiratory chain, or virulence factors like exotoxins or antibiotic-resistance enzymes. To fold correctly and acquire biological activity, these proteins need to pass through the periplasmic space and be assisted in their folding by periplasmic oxido-reductases. The oxido-reductase enzymatic equipment in the periplasmic space consists of two pathways that work as a functional unit: the oxidation and the isomerization pathways. Both pathways are briefly described below.

B. The Oxidation Pathway in E. coli Periplasm

The oxidation pathway consists of DsbA, a powerful oxidase (the most oxidizing protein known) and its modulator, DsbB, that couples DsbA with the respiratory chain (in aerobic conditions) or with the anaerobic electron acceptors (in anaerobic conditions). DsbA is a small periplasmic protein (21 kDa) with a thioredoxin fold displaying the CXXC motif in its active site (CPHC (SEQ ID NO: 52) in DsbA) that is shared with several other oxido-reductases including all cytoplasmic thioredoxins, DsbC, γ-domain of DsbD and eukaryotic protein disulfide isomerase (PDI) (Raina and Missiakas 1997). DsbA's high oxidizing redox potential (−120 mV) agrees with the oxidant role of this protein. Oxidized DsbA is very unstable and reacts rapidly with unfolded proteins entering the periplasmic space (Zapun, Bardwell et al. 1993).

Figure 2:
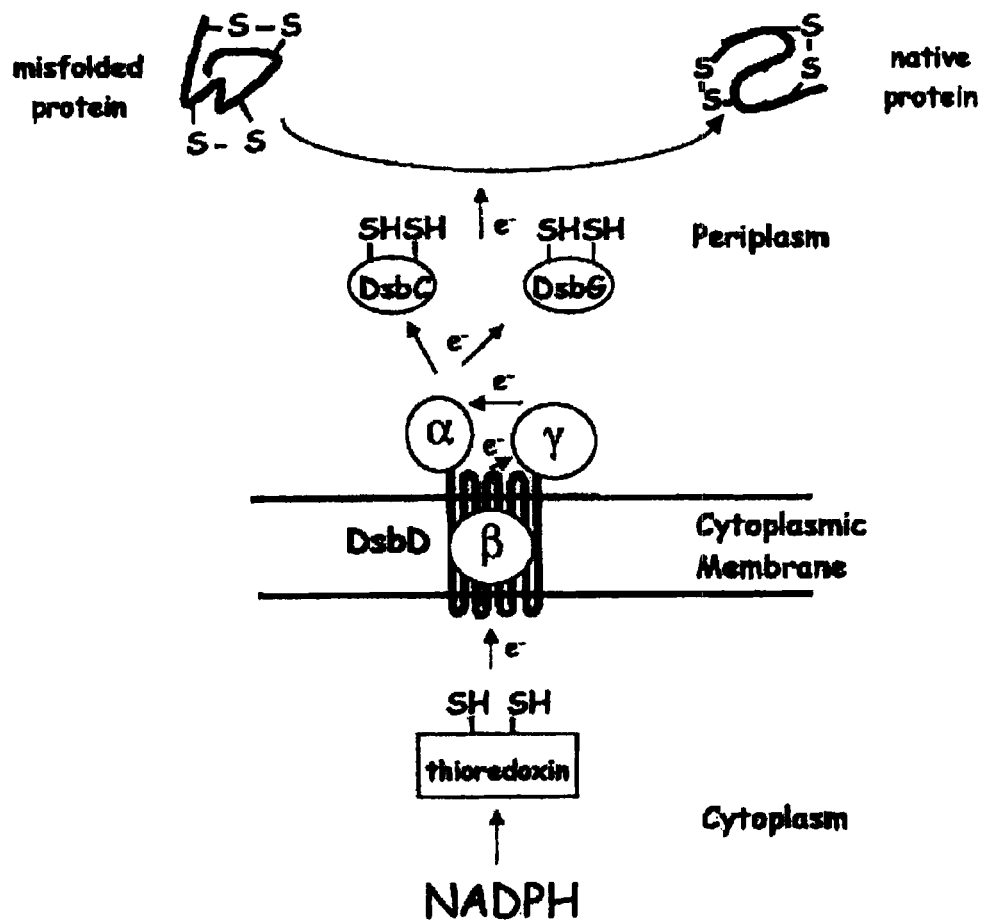
FIG. 2 depicts the isomerization pathway in *E. coli* periplasm (from Collet and Barwell 2002).

DsbA is reduced after the transfer of its active site disulfide bridge to the eukaryotic protein. In order to act catalytically, DsbA needs to be recharged. The protein responsible for DsbA's reoxidation is an inner membrane-embedded protein called DsbB, which is the only Dsb protein thought to not have a thioredoxin-like domain (Collet and Bardwell 2002). DsbB is a 21 kDa inner-membrane protein spanning the membrane four times. DsbB has two pairs of essential cysteine residues, one pair located in each of its two periplasmic domains. Only the first pair has the CXXC motif and although the three-dimensional DsbB structure has not yet been solved, DsbB is unlikely to contain a domain with a thioredoxin-like fold. The possibility that molecular oxygen and the electron transport chain could be involved in the reoxidation of DsbB was a hypothesis raised when DsbB was first isolated (Bardwell, Lee et al. 1993). Accumulating evidence and the in vitro reconstitution of the bacterial disulfide bond catalysis system using purified components verified the connection between electron transport and disulfide bond formation (Bader, Muse et al. 1999). It has been demonstrated that DsbB is linked with the quinone system of the inner membrane, and under aerobic conditions, DsbB transfers its electrons to oxidized ubiquinone, which then donates them to cytochrome oxidases, which reduce oxygen. Under anaerobic conditions, DsbB passes its electrons to menaquinone and then to anaerobic electron acceptors. There is a continuous flow of reducing equivalents from the periplasmic space and DsbA to the electron transfer quinone system, which is made possible by membrane-embedded DsbB which functions to regenerate DsbA. The oxidation pathway in the E. coli periplasm is illustrated in FIG. 2 (from (Collet and Bardwell 2002).

C. The Isomerization Pathway in E. coli Periplasm

For any protein that contains more than two cysteine residues, the possibility exists that incorrect disulfide bonds will occur during recombinant expression. This statement is especially true for DsbA which tends to match cysteines extremely fast (tens of seconds) in the periplasmic space with little respect for their native conformation. That DsbA can form non-native disulfides in a protein was demonstrated in vitro in RNase A refolding experiments. DsbA, in the presence of DsbB and quinones, completely oxidizes RNase A, but the oxidized RNase A, which has four disulfide bonds, shows no activity unless glutathione redox buffers are added (Bader, Xie et al. 2000).

For this reason, in the periplasmic space the highly-efficient oxidizing equipment is matched with a powerful isomerization system consisting of two more Dsb proteins: DsbC and its modulator, DsbD. Originally it was felt that DsbC had the ability to catalyze disulfide bond formation by acting as an oxidase (Missiakas, Georgopoulos et al. 1994), but it is now thought that DsbC acts mainly as a disulfide isomerase and chaperone in vivo. DsbC mutants, like DsbA and DsbB mutants, are defective in disulfide bond formation. DsbC mutations especially affect the folding of those proteins exhibiting multiple disulfide bonds: urokinase (12 disulfide bonds) is badly misfolded, whereas the production of alkaline phosphatase (2 disulfide bridges) is only slightly affected (Rietsch, Belin et al. 1996). Since the number of possible incorrect disulfides grows exponentially with the number of cysteine residues in a protein, the presence of an efficient isomerase is crucial for the proper folding of multiple disulfide-bond proteins.

DsbC is a V-shaped homodimer of two identical 23 kDa subunits. Each subunit has four cysteine residues. The active site contains the Cys-98-Cys-101 pair (the CXXC motif in DsbC is CGYC (SEQ ID NO: 44)) which is directly involved in DsbC's oxido-reductase activity (Zapun, Missiakas et al. 1995). The crystal structure of DsbC has been solved (McCarthy, Haebel et al. 2000), and it has been shown that each arm of the V-shaped homodimer is a DsbC monomer consisting of two separate domains connected by a hinged three-turn linker $\alpha$-helix. The N-terminal domains (residues 1-61) from each monomer join to form the dimer interface at the base of the V-shaped homodimer. The C-terminal catalytic domain (residues 78-216) has a thioredoxin fold as predicted. The two active site CXXC motifs face each other in the interior of the V-shaped homodimer. The surface of this V-shaped cleft is composed mainly of hydrophobic and uncharged residues, suggesting that it might be involved in the non-covalent binding of eukaryotic proteins conferring DsbC chaperone activity. DsbC is particularly efficient in rearranging buried, non-native disulfide bonds formed under oxidizing conditions (Maskos, Huber-Wunderlich et al. 2003). DsbC action is believed to work as follows: Cys-98 attacks an incorrect disulfide bridge in the substrate protein and a mixed disulfide is formed between DsbC and the misfolded protein. This mixed disulfide is then resolved either by attack of another cysteine of the misfolded protein, resulting in the formation of a more stable disulfide in the substrate and reduced DsbC, or, more often, by attack of Cys-101 of DsbC. In this case, DsbC becomes oxidized and needs to be reduced in order to be recycled (Collet and Bardwell 2002). It has been shown that, to function as an isomerase, DsbC needs to be kept reduced within the very oxidizing environment of the periplasm. If DsbC is not re-reduced at the end of its catalytic cycle, it tends to function as an oxidase, losing its isomerase activity. The enzyme that keeps DsbC reduced is an inner membrane-embedded protein called DsbD.

Figure 3A:
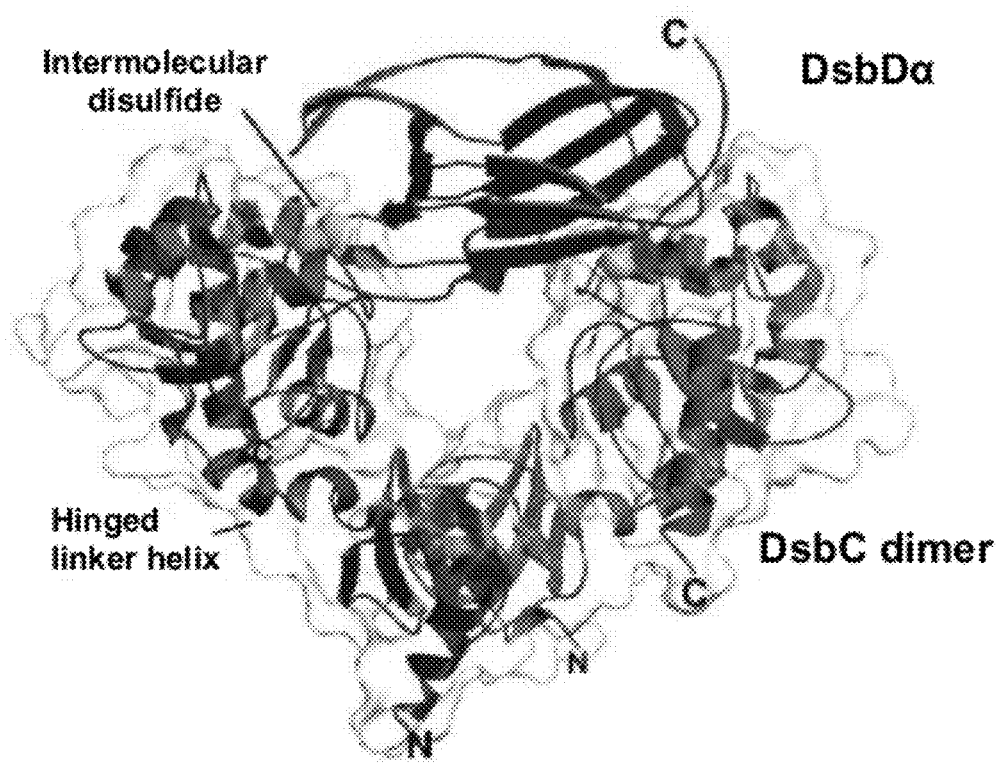
FIG. 3 shows the crystal structure of DsbC and DsbC-DsbDα interaction revealed after docking DsbDα into DsbC cleft (from Haebel, Goldstone et al. 2002).
Figure 3B:
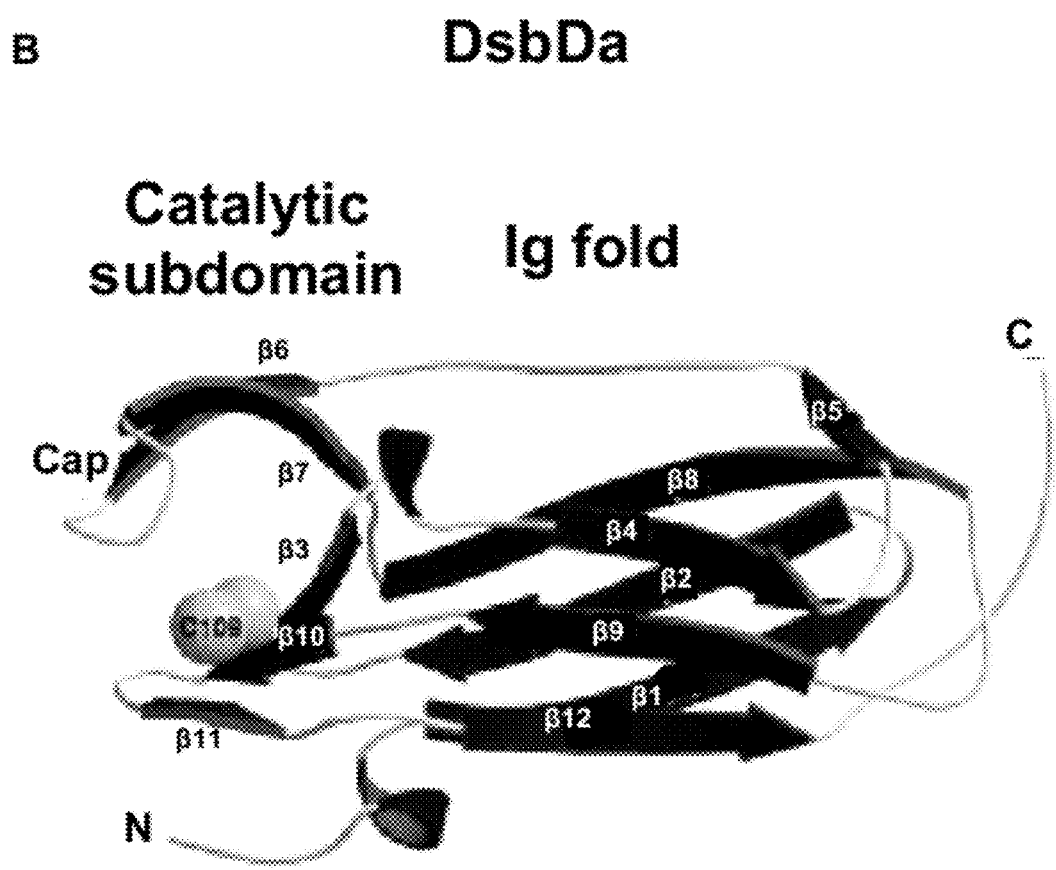
Figure 3C:
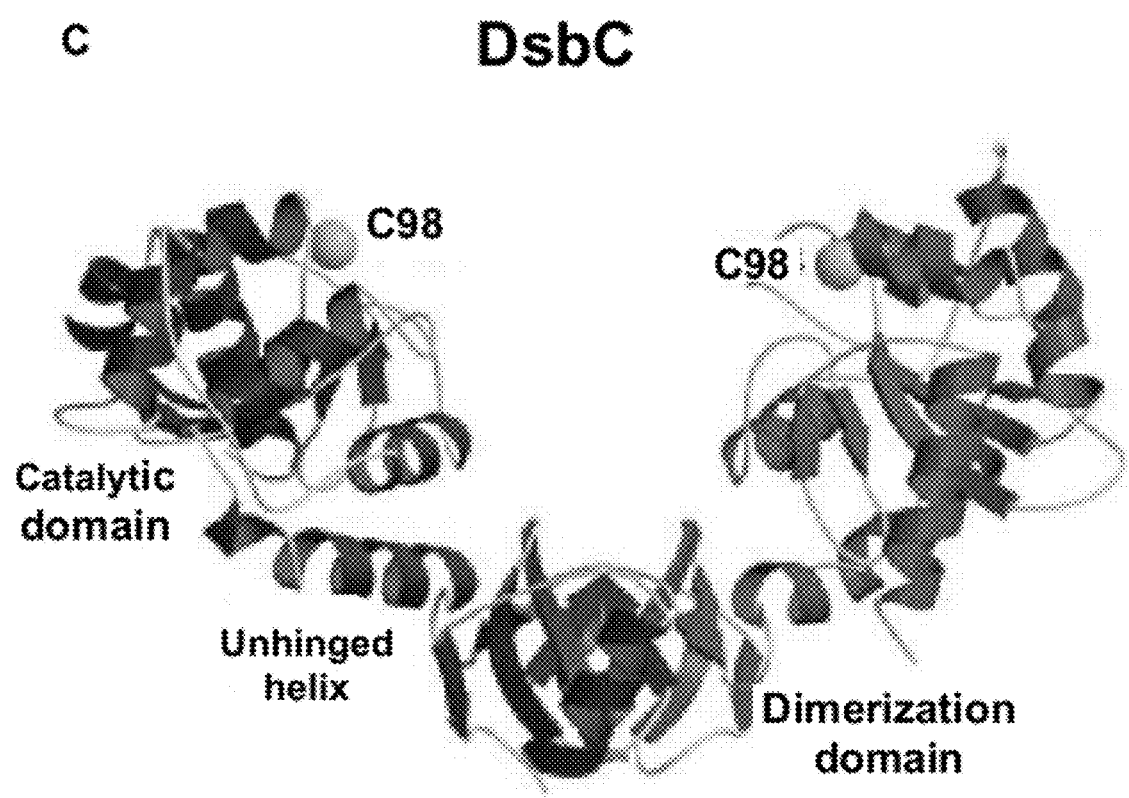

The thiol-disulfide interchange protein DsbD has a molecular mass of 59 kDa, making it the largest protein in the Dsb family. Topological studies have revealed that DsbD has three distinct domains: an N-terminal periplasmic domain ($\alpha$-domain) with a particular immunoglobulin fold (Haebel, Goldstone et al. 2002), followed by a hydrophobic core with eight transmembrane segments ($\beta$-domain), and a second periplasmic domain ($\gamma$-domain), which is predicted to have a thioredoxin-like fold (Katzen and Beckwith 2000). Each domain of DsbD has two conserved cysteine residues. Site-directed mutagenesis experiments showed that single cysteine-to-alanine active site mutants led to accumulation of oxidized DsbC and are unable to produce active urokinase, similar to DsbD null mutants (Gordon, Page et al. 2000). A model for the mechanism of DsbD action has recently proposed and involves the successive transfer of electrons from cytoplasmic thioredoxin to the $\beta$-domain of DsbD, then, across the membrane, successively to the $\gamma$- and $\alpha$-domains, and finally to DsbC. This mechanism of action is illustrated in FIG. 2. This model is based on the observation of disulfide cross-links between DsbC and the $\alpha$-domain of DsbD (Katzen and Beckwith 2000; Katzen and Beckwith 2003). In addition, purified $\alpha$-domain was recently shown to be able to interact with and reduce DsbC in vitro (Goldstone, Haebel et al. 2001). The crystal structure of DsbC and the DsbC-DsbD$\alpha$ interactions revealed after docking DsbD$\alpha$ into DsbC cleft are shown in FIG. 3 (from Haebel, Goldstone et al. 2002).

D. Bacterial Periplasmic Space—Considerations

Figure 4:
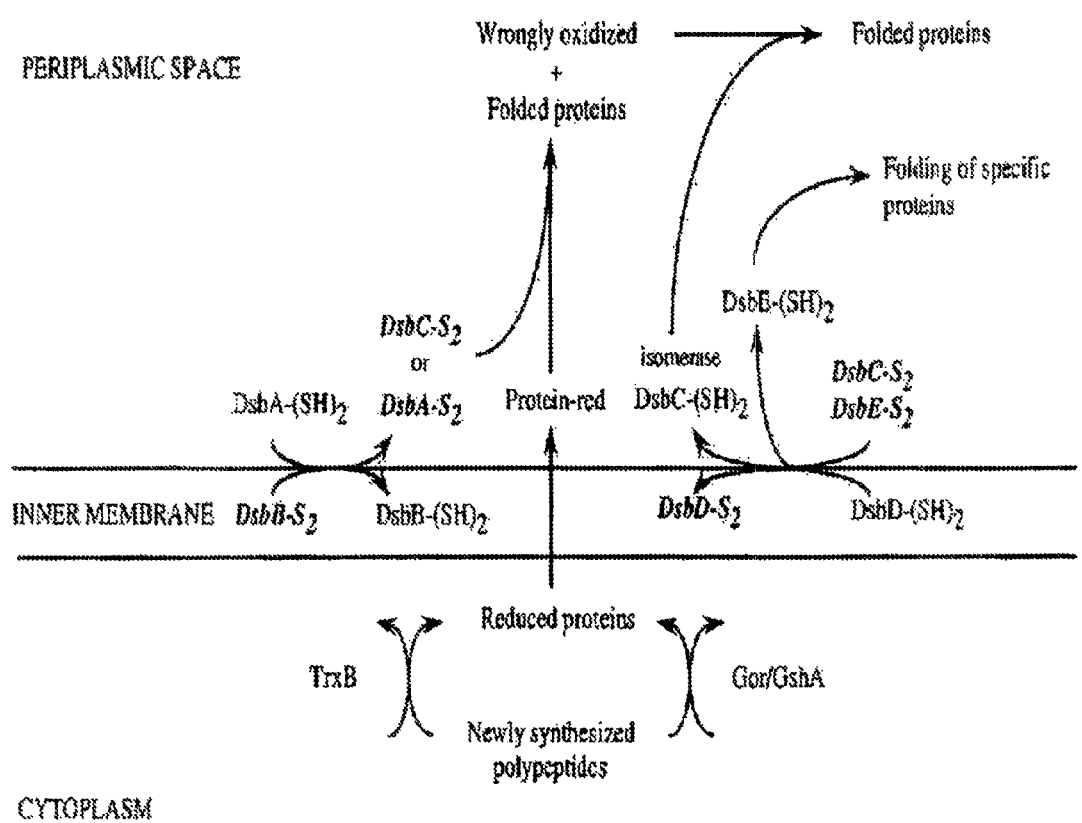
FIG. 4 shows a model of disulfide bond formation catalyzed by the various Dsb foldases in the periplasm of *E. coli*.

Based on the above description, the oxidation/isomerization enzymatic equipment of periplasmic space has two main characteristics. First, it is designed like an electrical circuit that has two arms and in order to close the circuit, both arms must come into contact with the folding cysteine-rich protein that is assisted by those foldases. By closing the circuit, the folding protein will ensure a continuous flow of reducing equivalents from cytoplasm (NADPH) through both enzymatic arms to the electron transfer chains in the membrane (respiratory chain in aerobic conditions or anaerobic electron acceptors in the absence of oxygen) in one direction, and a constant transfer of disulfide bonds in the other direction. This explains how the main enzymes of each pathway, DsbA oxidase and DsbC isomerase, constantly regenerate and assist protein folding in an uninterrupted fashion. Second, although both pathways coexist in the same oxidizing compartment, they are kept kinetically separate. DsbA needs to be kept oxidized in order to function as a disulfide donor, and DsbC needs to be kept reduced to work as an isomerase. This means two systems with opposite goals can coexist in the same periplasmic space. It has been shown that DsbB reoxidizes DsbC at least 500-fold more slowly than it does DsbA, suggesting that DsbB can distinguish between these two proteins (Bader, Xie et al. 2000). The reason for this behavior is the dimerization interface of DsbC, which protects the dimer from interacting with DsbB and keeps its active sites protected from DsbB oxidation. It has been demonstrated that mutated monomeric variants of DsbC interact with DsbB being able to rescue a dsbA$^-$ phenotype and substitute for DsbA oxidase. A model of disulfide bond formation in E. coli periplasm as described above is shown in FIG. 4 (from Raina and Missiakas 1997).

E. coli has the complete enzymatic equipment, reminiscent of the endoplasmic reticulum of eukaryotes, for catalyzing the correct folding of multiple cysteine-rich proteins in the periplasmic space. It has been demonstrated that complex multiple disulfide bond eukaryotic proteins can be expressed as biologically active native conformers through the periplasmic space. Further, the yield is significantly enhanced if DsbA and/or DsbC are also co-overexpressed (Becker and Hsiung 1986; Kurokawa, Yanagi et al. 2000; Kurokawa, Yanagi et al. 2001).

There are two main issues with recombinant protein production in periplasmic spaces. The main issue is that the periplasmic space was not designed to serve as a mass production site. Bacterial multiple disulfide bond proteins that follow this path are secretory proteins, like exotoxins or β-lactamase, that are active in small quantities, or key components of the locomotor apparatus which are assembled in the extracellular space. The second problem derives from the fact that protein transport to the bacterial periplasm is a particularly complex and incompletely understood process, and the presence of a signal peptide does not always ensure efficient protein translocation through the inner membrane (Makrides 1996). For instance, Hsiung et al. observed in their study (Becker and Hsiung 1986) intracellular accumulation of a greater amount of human growth hormone precursor including a signal sequence after isopropyl-beta-D-thiogalactopyranoside (IPTG) induction, but no increase in the amount of translocated human growth hormone.

E. Disulfide Bond Formation in the *E. coli* Cytoplasm and Thioredoxins

Figure 5:
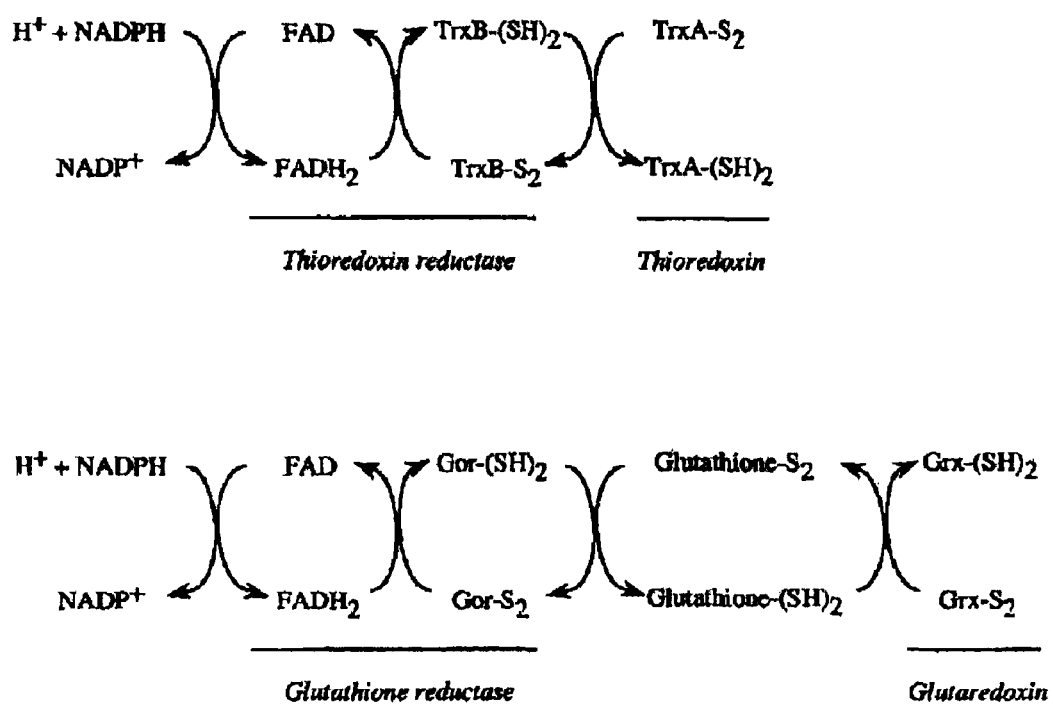
FIG. 5 shows the thioredoxin and glutaredoxin pathways in *E. coli* cytoplasm (from Raina and Missiakas 1977). TrxA: thioredoxin; TrxB: thioredoxin reductase; Grx: glutaredoxin; Gor: glutathione reductase.

Bacterial cytoplasmic proteins do not generally contain structural disulfide bonds, although certain cytoplasmic enzymes form such bonds as part of their catalytic cycles. The disulfide bonds in these latter enzymes are reduced in *E. coli* cytoplasm by two systems: the thioredoxin pathway and the glutathione/glutaredoxin pathway (Stewart, Aslund et al. 1998). Under physiological conditions, these two reductive pathways maintain the cytoplasm in a reduced state that strongly disfavors the formation of stable disulfide bonds in proteins. The main reductive pathways in *E. coli*, with thioredoxin reductase (encoded by trxB gene) and glutathione reductase (encoded by gor gene) as the key enzymes are illustrated in FIG. 5. However, mutants in which the reduction of one or both thioredoxins and glutathione is impaired (trxB or trxB/gor mutants) accumulate oxidized disulfide bond proteins, like enzymatically active human alkaline phosphatase in the cytoplasm (Stewart, Aslund et al. 1998; Bessette, Aslund et al. 1999). The formation of disulfide bond in these mutants is dependent on the presence of cytoplasmic thioredoxins that suffer a role reversal and actively assist the formation of disulfide bridges, thus functioning as oxidases in this case. The double mutants grow very poorly in the absence of an exogenous reductant (e.g. DTT) and accumulate extragenic suppressors at a high frequency: fast growing colonies that are DTT-independent. This suppressor mutation was mapped in ahpC gene, which encodes for a peroxiredoxin in its wild type form. The mutation borne by FA113 (one of the fast growing suppressors) makes this enzyme act as a disulfide reductase (Jurado, Ritz et al. 2002). In rich or defined media, *E. coli* FA113 grows almost as well as *E. coli* DHB4 with doubling times of approx. 35 minutes. A delay in the growth-rate of FA113 (doubling times of approx. 60 minutes) has been reported when some antibiotics such as chloramphenicol, kanamycin, or tetracycline were used for selection (Jurado, Ritz et al. 2002).

F. Prokaryotic System for Supporting Disulfide Bond Formation of Heterologous Proteins in Cytoplasm In the quest to further engineer the FA113 double mutant to make it more efficient in its ability to assist the correct folding of disulfide-rich proteins in cytoplasm, the activity of the periplasmic enzymatic equipment is imported into the cytoplasm to help the folding of heterologous recombinant proteins in this compartment. Previous descriptions of this approach have focused on heterologous proteins such as antibody fragments (in scFv or Fab format) or some other eukaryotic cysteine-rich proteins (Levy, Weiss et al. 2001; Jurado, Ritz et al. 2002; Venturi, Seifert et al. 2002; Maskos, Huber-Wunderlich et al. 2003).

Modified expression hosts reported previously contain either a signal sequenceless oxidase (ΔssDsbA or active site mutated variants) or a signal sequenceless isomerase (usually ΔssDsbC) imported from the periplasmic space and simultaneously co-overexpressed, along with the cysteine-rich recombinant protein, in the cytoplasm of the double mutant trxB⁻/gor⁻ strain (Levy, Weiss et al. 2001; Jurado, Ritz et al. 2002). This type of system has been used to generate Fab antibody fragments in *E. coli*, and has been shown to improve the yield of correctly folded antibodies compared to wild type strains (from nanograms to approx. 1 mg/L of recombinant protein). However, although considered as a step forward, such system failed to generate the yields expected. One problem with this approach is the oxidase/isomerase combination simultaneously co-overexpressed does not efficiently catalyze the disulfide bridge formation in the recombinant protein because such system lacks the extraordinary ability of the periplasmic space to regenerate its foldases. Based on the periplasmic space principle, the oxidase and the isomerase imported from the periplasmic space need be constantly recharged in order to function. For this reason, a third component is required to bridge the oxidase/isomerase enzymatic equipment imported into the cytoplasm. This component(s) should link the oxidase with the isomerase co-overexpressed in FA113 by recharging them constantly and keeping the flow of reducing equivalents in one direction, and disulfide bridge transfer in the other direction.

In accordance with the methods of the invention, the recombinant system uses key enzymes from both compartments (periplasmic and cytoplasmic) that are naturally interacting with each other, instead of molecules that are forced to artificially interact to reconstitute the system. A natural combination includes DsbA, DsbB, DsbC and DsbD, but to import all of them into the cytoplasm is difficult. Simultaneous co-overexpression in the cytoplasm of DsbA, DsbB, DsbC and DsbD has been reported. However the net gain from such expression was not impressive (DsbA/DsbB/DsbC/DsbD expression plasmid—CA2281035). This may be explained by the fact that DsbB and DsbD which physiologically function as membrane-embedded molecules might not function properly when expressed as soluble proteins in the bacterial cytoplasm. Second, DsbB, as described above, is coupled with the electron transfer chains. By expressing DsbB in the cytoplasm, the protein may be unable to recharge DsbA, compromising the expression system. On the other hand, the DsbC-DsbD partnership might not be affected assuming that the soluble form of DsbD can still function in the cytoplasm and react with thioredoxin, its upstream partner, and with DsbC, its downstream partner. For a system designed on DsbC-DsbD partnership in the cytoplasm to further become auto-regenerating, it would also need a third component—an oxidase partner. The idea of using cytoplasmic thioredoxin A (thioredoxin 1) as DsbC-DsbD oxidase partner is attractive because DsbD naturally interacts with both thioredoxin A and DsbC.

DsbD molecule is a large transmembrane protein displaying hydrophobic domains. Because of its size and membrane spanning hydrophobic β-domain, expression of the DsbD α-domain in the cytoplasm is preferred over expression of the full length DsbD molecule. The full-length DsbD protein is too big to be efficiently co-overexpressed in the same system with three other proteins. The DsbD α-domain represents amino acids 1-131 of DsbD following removal of a cleavable signal sequence of 19 aa. DsbD α-domain on its own interacts efficiently with DsbC in vitro, and is able to keep it reduced and to subsequently recharge its isomerase partner (Goldstone, Haebel et al. 2001; Goulding, Sawaya et al. 2002). When stoichiometric amounts of reduced DsbD α-domain and oxidized DsbC are mixed, a rapid reaction takes place and DsbC is very quickly reduced. Whether DsbD α-domain interacts with thioredoxin A, the natural partner of DsbD, has been suggested by Collet et al (Collet, Riemer et al. 2002), who describes an in vitro reconstituted periplasmic bacterial disulfide isomerization system. First, in the presence of a catalytic amount of DsbD α-domain alone, the reduction of DsbC took place at a rate comparable to that measured in the presence of all three domains together. This indicates that the activity observed in the presence of all three domains could only be explained by the contribution of the α-domain alone. Second, by mixing stoichiometric quantities of thioredoxin with DsbD α-domain, it was surprisingly found that thioredoxin efficiently reduces α-domain directly in vitro. A very low activity was observed when thioredoxin was incubated with oxidized DsbD γ-domain or with oxidized DsbC. This last observation is significant because it is known that DsbC is kinetically isolated from the oxidation system (periplasmic DsbA), and that DsbC does not interact with cytoplasmic thioredoxin either.

As disclosed herein, a novel powerful redox system can be recreated in the cytoplasm of $E.$ $coli$ trxB$^-$/gor$^-$ double-mutant strain (FA113) by combining an oxidase (thioredoxin A) with an isomerase (ΔssDsbC; mature DsbC minus the signal sequence) and further linking them together in the same compartment by utilizing the DsbD α-domain (ΔssDsbDα), the missing molecular component with the ability to regenerate the foldase enzymatic equipment. In this novel in vivo system, the recombinant disulfide containing eukaryotic protein closes the circuit and DsbD α-domain is the key molecule to fill the gap between the oxidation and isomerization pathways ensuring that the reducing equivalents from thioredoxin to DsbC are flowing in one direction, while the constant transfer of disulfide bridges is taking place in the other direction.

Attempts to mutate the active sites of thioredoxin and DsbC to increase the activity of these enzymes have been reported. (Mossner, Huber-Wunderlich et al. 1998; Bessette, Aslund et al. 1999; Bessette, Qiu et al. 2001). The wild type thioredoxin has an active site with a very low redox potential (−270 mV), a value that is in good agreement with its primary function as a reductase in bacteria. It was reported that improved oxidase activity of thioredoxin A can be achieved by replacing the wild type thioredoxin active site motif CGPC (SEQ ID NO: 48) with bacterial glutaredoxin A's active site motif CPYC (SEQ ID NO: 49). Such change modifies the active site redox potential of thioredoxin from −270 mV (wild type) to −195 mV (glutaredoxin-type), and the mutated glutaredoxin-type thioredoxin becomes a better oxidase. The glutaredoxin-type mutant was able to generate better yields of disulfide-rich proteins when this thioredoxin mutant and the disulfide rich proteins were co-overexpressed in the same system (Bessette, Aslund et al. 1999).

Another thioredoxin mutant of interest is the PDI-like thioredoxin, a thioredoxin including the eukaryotic protein disulfide isomerase active site motif. It has been previously shown that replacing the wild type thioredoxin active site motif with the eukaryotic protein disulfide isomerase sequence CGHC (SEQ ID NO: 50) increases the active site redox potential from −270 mV to approximately −229 mV. The change in redox potential renders the PDI-type thioredoxin a more effective enzyme in the FA113 system, not only a better oxidase than wild type thioredoxin but also a better reductase than the glutaredoxin-type thioredoxin mutant.

Active site mutants of DsbC have also been described. The DsbC active site CGYC (SEQ ID NO: 44) was replaced with CGFC (SEQ ID NO: 45) or CTFC (SEQ ID NO: 46) which were found to increase isomerase activity. The yield of a multiple disulfide-bond protein generated in the FA113 strain has been shown to increase when these active site DsbC mutants were co-overexpressed (Bessette, Qiu et al. 2001).

Origami and Rosetta-gami strains are double-mutants in trxB and gor gene products that render the two main reducing enzymatic pathways in $E.$ $coli$ cytoplasm inoperable. This makes the cytoplasmic microenvironment more oxidative which, ultimately, makes this compartment a more suitable place for disulfide bond formation.

The Origami and Rosetta-gami strains have growth rates and biomass yields close to those obtained by $E.$ $coli$ wild type strains, making it attractive for large-scale production and purification of recombinant CN.

For recombinant production of CN in $E.$ $coli$, a system consisting of Origami B(DE3)pLysS expression host in combination with pET32a vector with a strong T7lac promoter (Novagen) has been employed. Origami B host strains carry the same trxB/gor mutations as the original Origami strains (FA113), except that they are derived from a lacZY mutant of BL21. Thus, the Origami B strains combine the desirable characteristics of BL21 (deficient in ompT and ion proteases), Tuner and Origami hosts into a single strain.

It has been found that mutations in both the thioredoxin reductase (trxB) and glutathione reductase (gor) genes greatly promote disulfide bond formation in the cytoplasm. Expression in Origami (DE3) yields 10-fold more active protein than in another host even though overall expression levels are similar (Prinz, Aslund et al. 1997).

In the absence of IPTG (isopropyl-beta-D-thiogalactopyranoside) inducer, there is a detectable level of expression of T7 RNA polymerase from the lacUV5 promoter in the DE3 lysogens, resulting in a basal expression of the recombinant protein. Such low level of recombinant protein expression in $E.$ $coli$ may interfere with the normal growth processes of the cell and may, therefore, be "toxic" to the bacteria. One approach to control basal expression is to use vectors that contain a T7lac promoter (Studier, Rosenberg et al. 1990; Dubendorff and Studier 1991). These plasmids contain a lac operator sequence just downstream of the T7 promoter and carry the natural promoter and coding sequence for the lac repressor (lacI), oriented so that the T7lac and lacI promoters diverge. The lac repressor in the vector acts both at the lacUV5 promoter level in the host chromosome to repress transcription of T7RNA polymerase gene by the host polymerase and at the T7lac promoter in the vector to block transcription of the eukaryotic gene by any T7RNA polymerase that is produced.

Reducing basal eukaryotic protein expression may be accomplished by expressing in host strains that contain a compatible chloramphenicol-resistance plasmid from which is expressed a small amount of T7 lysozyme, a natural inhibitor of T7RNA polymerase (Studier 1991). A pLysS host has little effect on growth rate and overall pLysS increases the tolerance of λDE3 lysogens for plasmids with toxic inserts: Unstable plasmids become stable, and plasmids that would not otherwise be established can be maintained and expressed. The presence of pLysS has the further advantage of facilitating the preparation of cell extracts because cells are less resistant to freezing and thawing cycles and lyse easily.

The Tuner strain and derivatives (Origami B and Rosetta-gami B) are lacY1 deletion mutants of BL21 that enable adjustable levels of protein expression. The lac permease (lacY1) mutation allows a uniform entry of IPTG (a lactose derivative) into the cell, which produces a concentration-dependant, homogenous level of induction. By adjusting the concentration of IPTG, expression can be regulated from a very low up to high levels; however the optimal level of eukaryotic protein expression may be achieved at a significantly lower level of IPTG than is normally used. This approach offers cost savings with respect to IPTG.

An important feature of the Origami and Rosetta-gami strains is the ability to provide sufficient oxidizing power to catalyze disulfide bond formation of heterologous recombinant proteins. However, such a system lacks isomerization power. Disulfide bond formation of recombinant proteins takes place at an accelerated rate in Origami/Rosetta-gami cytoplasm compared to wild type *E. coli*, but there is no enzymatic equipment to ensure the correct match and to generate a product with identical disulfide pattern as in the native conformers.

Disulfide bond isomerization, and not disulfide bond formation, is limiting for folding of multiple disulfide-bond proteins in the periplasm of *E. coli* wild type cells. Origami cells have no enzymatic equipment in the cytoplasm to either ensure the correct pairing of disulfide bridges or to reshuffle the incorrectly formed ones into the correct position. Thus, further engineering of the host protein may be needed to increase the level of isomerization activity in the cytoplasm.

Origami *E. coli* strain (FA113) may be modified to cytoplasmically overexpress the DsbC isomerase (DsbC without its signal sequence; "ΔssDsbC") and the DsbD α-domain (DsbD without a signal sequence; "ΔssDsbDα"), the latter functioning to reduce cysteines of the active site of DsbC isomerase. Although not wishing to be bound by any theory, it is believed that DsbD α-domain is the key molecule to fill the gap between the novel oxidation (TrxA) and isomerization (DsbC) pathways in the cytoplasm that keeps the reducing equivalents from thioredoxin to DsbC flowing in one direction and the constant transfer of disulfide bridges in the other direction. The combination of these two features creates a system with the capacity for auto-regeneration.

Increased expression of disulfide-bridge containing proteins may be obtained by using mutant trxA and dsbC gene products. Active site mutants with increased oxidase and isomerase activity have been reported (Mossner, Huber-Wunderlich et al. 1998; Bessette, Aslund et al. 1999; Bessette, Qiu et al. 2001). Active site mutant thioredoxins with glutaredoxin A active-site motif CPYC (SEQ ID NO: 49) and eukaryotic PDI active site motif CGHC (SEQ ID NO: 50) are preferred. Active site mutant DsbC isomerases with CGFC (SEQ ID NO: 45) and CTFC (SEQ ID NO: 46) active site motifs are preferred.

Methods of Use

Eukaryotic proteins produced as described herein may be used for treatment of various diseases and conditions for which the native protein may be used. Such proteins can be administered as a pharmaceutical or medicament formulated with a pharmaceutically acceptable carrier. Accordingly, the eukaryotic proteins may be used in the manufacture of a medicament or pharmaceutical composition.

Homodimeric and monomeric disintegrins described herein (e.g. VN) may be used for any purposes for which native homodimeric disintegrins may be employed. Such uses are described in U.S. patent publication no. 2003/0186884, published Oct. 2, 2003.

In addition, homodimeric and monomeric disintegrins may be used to modulate the adhesion, motility, and invasiveness of integrin expressing tumor cells. When formulated as a pharmaceutically acceptable composition, such proteins can be used to treat patients by inhibiting or disrupting disease processes associated with a ligand binding to an αvβ3 or αvβ5 integrin.

Homodimeric and monomeric disintegrins described herein (e.g. VN) may be used in methods to decrease the motility of an αvβ3 integrin expressing cell, the method comprising cross-linking at least two αvβ3 integrins on the integrin expressing cells thereby inhibiting the motility of said cells. Such crosslinking is believed to disrupt FAK signaling and activates tyrosine phosphorylation of FAK and CAS. Moreover, the crosslinking is believed to induce an alteration in cell morphology, including changes of cytoskeletal or focal adhesion structures. In a preferred embodiment, αvβ3 integrin expressing cell is a tumor cell.

Homodimeric and monomeric disintegrins described herein (e.g. VN) may be used to inhibit the adhesion of integrin expressing cells to vitronectin by exposing the cells to the homodimeric and monomeric disintegrin. The homodimeric and monomeric disintegrin is believed to inhibits adhesion by binding to an integrin, in particular αvβ3 or αvβ5 integrin.

Homodimeric and monomeric disintegrins described herein (e.g. VN) may be formulated as compositions for the treatment of thrombotic diseases in mammals, alone or in conjunction with one or more thrombolytic agents. In particular, such compositions have utility in treating or preventing arterial, venous and microvascular thrombosis and thromboembolism. Such compositions also have utility in treating stroke, transient ischemic attacks, arteriosclerosis, atherosclerosis, pulmonary embolism, aneurisms and angina. In particular, such compositions have utility in preventing or treating myocardial infarctions.

Homodimeric and monomeric disintegrins described herein (e.g. VN) may be used to inhibit metastasis in melanoma, carcinoma and sarcoma patients. In particular embodiments Homodimeric and monomeric disintegrins may be used to prevent metastasis in breast cancer patients.

Homodimeric and monomeric disintegrins described herein (e.g. VN) may be used to treat osteoporosis. Compositions and methods for treatment of osteoporosis employing an amount of a homodimeric and monomeric disintegrin effective to inhibit bone resorption by osteoclasts may be used.

Homodimeric and monomeric disintegrins described herein (e.g. VN) may be used to promote wound healing. Homodimeric and monomeric disintegrins may inhibit cell-cell and cell-extracellular matrix interactions (including interaction with fibronectin), thus promoting wound repair, including keloid formation. Compositions containing homodimeric and monomeric disintegrins may be used to prevent adhesion formation when administered to a patient in need of such treatment.

Pharmaceutical compositions containing homodimeric and monomeric disintegrins should comprise at a minimum an amount of protein effective to achieve the desired effect (i.e., prevent thrombus formation, prevent metastasis in carcinoma patients, prevent adhesion formation, etc.) and a suitable carrier or excipient. Generally, in these compositions, homodimeric and monomeric disintegrins are present in an amount sufficient to provide about 0.01 mg/kg to about 50 mg/kg per day, preferably about 0.1 mg/kg to about 5.0 mg/kg per day, and most preferably about 0.1 mg/kg to about 0.5 mg/kg per day. Such compositions have particular utility in the prevention of thrombus formation.

Homodimeric and monomeric disintegrins may be administered in combination with at least one thrombolytic agent present in an amount effective to achieve thrombolysis. Suitable thrombolytic agents include, but are not limited to, the following: anisoylated plasminogen streptokinase activator complex (APSAC); tissue-type plasminogen activator (tPA); urokinase-type plasminogen activator (uPA); and fibrolase, a snake venom fibrinolytic agent as described in U.S. Pat. No. 4,610,879 to Markland, Jr. et al.

Homodimeric and monomeric disintegrins may be administered by a variety of heretofore known means suitable for delivery thereof into the blood stream in substantial amounts. Intravenous administration of homodimeric and monomeric disintegrins in a suitable liquid vehicle or excipient is presently contemplated as the preferred route of administration. Homodimeric and monomeric disintegrins are soluble in water, and may therefore be effectively administered in a suitable aqueous solution (e.g., phosphate buffered saline). Alternatively, Homodimeric and monomeric disintegrins may be administered orally (in the form of tablets or capsules formulated with a suitable binder or excipient material, or in the form of aqueous or oily suspensions, solutions, emulsions, syrups or elixirs) or as a parenteral suspension. As is well known in the art, adjuvants such as local anesthetics, preservatives, buffering agents, lubricants, wetting agents, colorants, flavorings, fillers and diluents may suitably be included in any of these formulations.

The versatility of the invention is illustrated by the following Examples which illustrate preferred embodiments of the invention and are not limiting of the claims or specification in any way.

EXAMPLES

Example 1

Expression of Contortrostatin in Origami B Strain of E. coli

The Origami strain of bacteria (Novagen) that is based on FA113 double mutant was employed for recombinant CN production in bacteria.

Figure 6:
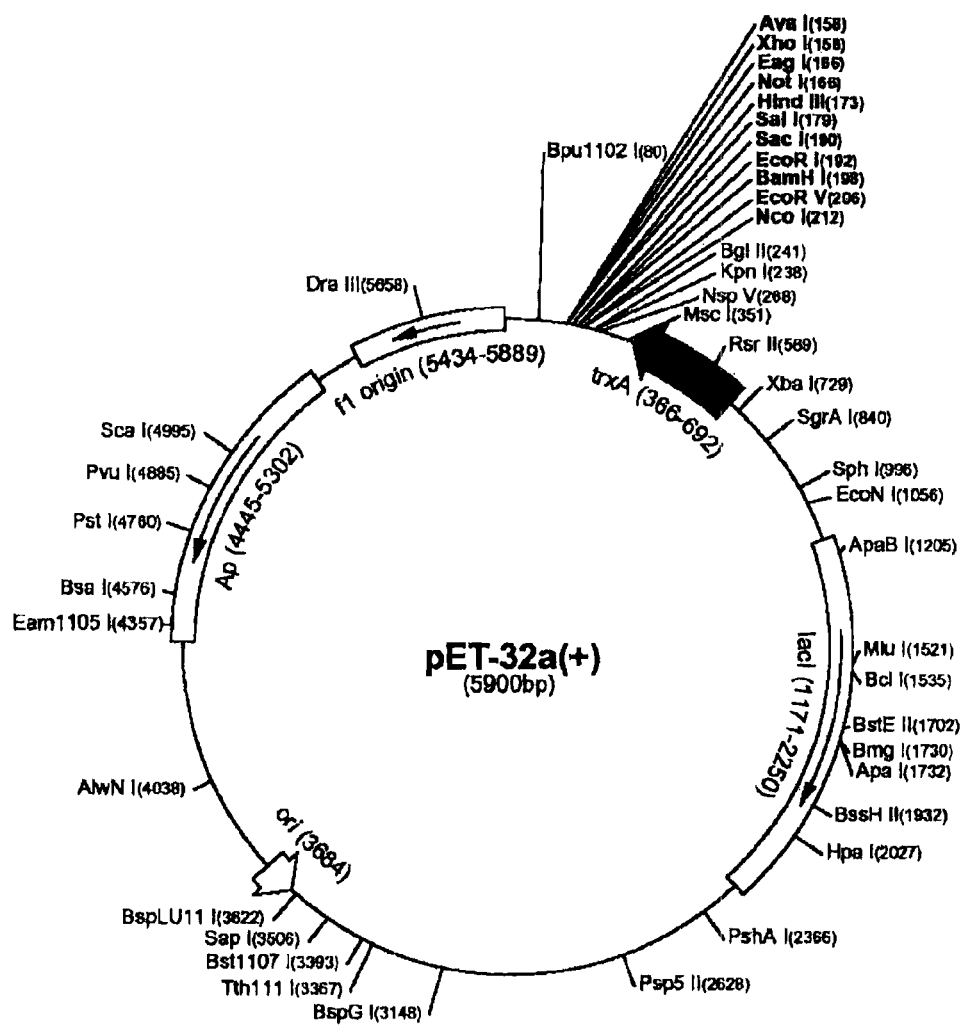
FIG. 6 shows a map of the pET32a vector (from Novagen).

The pET32a vector map shown in FIG. 6 (Novagen, Inc.) has been used for expressing peptide sequences fused downstream of a 109 amino acid thioredoxin wild type protein sequence (LaVallie, DiBlasio et al. 1993). Cloning sites are available for producing fusion proteins also containing cleavable His-tag sequence and S-tag sequence for detection and purification. As disclosed herein, disintegrins including recombinant CN sequences can be expressed as a fusion with thioredoxin to obtain an accelerated disulfide bond formation and an enhanced solubility of eukaryotic protein.

The sequence HKGPAT (SEQ ID NO: 47), which represents the C-terminal amino acid sequence of the monomeric disintegrin, echistatin, was included at the C-terminal end of the CN disintegrin domain sequence. This construct is a chimera that combines by the means of genetic engineering the sequences of two snake venom disintegrins with different originis: echistatin (a viperid disintegrin) and contortrostatin (a crotalid disintegrin). For this reason, this disintegrin construct that carries a C-terminal graft is referred to as "Vicrostatin" or "VN." CN disintegrin domain without the HKGPAT (SEQ ID NO: 47) sequence is referred to as "rCN" or "rCN construct." The amino acid sequence of vicrostatin is shown below as SEQ ID NO: 5

GDAPANPCCDAATCKLTTGSQCADG-
LCCDQCKFMKEGTVCRRARGDDLDDY CNGIS-
AGCPRNPHKGPAT (SEQ ID NO: 5).

The sequence of VN results from its expression as a fusion to thioredoxin and post expression processing as described below.

Contortrostatin wild type disintegrin domain or the disintegrin domain with echistatin C-terminal graft was directionally cloned by PCR into the pET32a vector, downstream of the thioredoxin sequence. The set of restriction enzymes used for cloning was: BglII/NcoI. The oligonucleotide primers employed for cloning were as follows:

CNfor1—forward primer for rCN (disintegrin domain) and VN (disintegrin domain) introducing BglII restriction site
5'GTTCCAGATCTCGAGAATCTTTACTTC-
CAAGGAGACGCTCCTGCAAATCCG TGCTGC-
GATGCTGCA3' (SEQ ID NO: 6)

CNback1—reverse primer for rCN (disintegrin domain) introducing the NcoI restriction site
5'GTTATTCGCCATGGCTTAGGCATG-
GAAGGGATTTCTGGGACAGCCAGCAG A3' (SEQ ID NO: 7)

CNback2—reverse primer for VN (disintegrin domain) introduction the NcoI restriction site
5'GTTATTCGCCATGGCTTAAGTAGCTG-
GACCCTTGTGGGGATTTCTGGGACA GCCA
GCAGATATGCC3' (SEQ ID NO:8)

The forward primer introduces a unique TEV protease cleavage site, which makes possible the removal of the thioredoxin fusion partner after purification of the fusion protein by Ni-column chromatography. The TEV protease recognizes with high specificity the canonical ENLYFQG (SEQ ID NO: 53) amino acid sequence engineered between recombinant CN and the thioredoxin fusion partner in this construct and following cleavage leaves a glycine at the N-terminus of rCN and VN. The reverse primer grafts the HKGPAT (SEQ ID NO: 47) segment to the C-terminus of the fusion protein. Thus, two recombinant fusion proteins, designated Trx-rCN and Trx-VN, were generated using the above described cloning strategy.

The initial cloning was carried out in the DH5a strain, which is recA⁻ endA⁻ and has high transformation efficiency and good plasmid yield. After validating the cloning by sequencing the constructs retrieved from DH5a transformants, the vector was used to transform the expression host, Origami B(DE3)pLysS, for expression optimization.

The Origami B/pET32a system produced up to 20 mg/L of recombinant CN (both Trx-rCN and Trx-VN constructs) without optimization. A single colony of transformed Origami B cells was used to inoculate a primary culture containing 10 mL LB broth with carbenicillin (100 µg/mL), tetracycline (12.5 µg/mL), kanamycin (15 µg/mL) and chloramphenicol (34 µg/mL). The culture was grown overnight to high turbidity and was used to inoculate 1 L of fresh LB broth with all 4 antibiotics. The first culture was used to inoculate a larger volume of LB broth plus antibiotics which was grown at 37° C. with shaking at 250 rpm to an $OD_{600}$ of 1-2. At this point, 1 mM IPTG was added and the cells further grown for another 3-5 hours at 37° C. with shaking at 250 rpm.

The cells were harvested and resuspended in 5 mL of cold 20 mM Tris-HCl, pH 7.5, and lysed by sonication. The insoluble cellular debris was removed by centrifugation at 40,000×g and the total soluble protein fraction collected. The total soluble protein fractions retrieved from cell lysates and analyzed by SDS-PAGE (FIG. 8) show that the fusion proteins (Trx-rCN and Trx-VN) were the prevalent species in this cell fraction. The fusion proteins in the total soluble protein fractions were subjected proteolysis by recombinant TEV protease following the manufacturer's protocol (Invitrogen) so as to cleave rCN or VN from its fusion partner, thioredoxin. Following TEV protease treatment (monitored by SDS-PAGE), the protein lysates were sterilized by passage through a 0.22 µm filter and further passed through a 30 kDa molecular cut-off filter (Millipore, Mass.). The recombinant disintegrin species (rCN or VN) contained in the filtrate were further recovered by reverse phase HPLC purification. Alternatively, the fusion proteins containing a His-tag sequence were initially purified by Ni-chelation affinity chromatography using a commercially available His*Bind resin kit (Novagen). After buffer exchange (removal of imidazole excess), the fusion proteins were subjected to overnight proteolysis at room temperature using TEV protease in the presence of a very small amount of DTT or GSH/GSSG to keep the TEV protease (a cysteine-protease) in a reduced (active) state. When proteolysis was complete (assessed by SDS-PAGE), the recombinant CN species (rCN or VN) were recovered by reverse phase HPLC purification.

C18-Reverse Phase HPLC was employed to purify recombinant CN constructs following TEV cleavage of the fusion protein. The HPLC column conditions used for rCN and VN were the same as for native CN. HPLC was conducted using a Vydac C18 column (218TP54, Temecula Calif.) in a solution of 0.1% TFA in water. A ten-minute rinse (at 1 ml/ml) of the column with the loading solution was followed by a linear gradient (0-100%) elution over 50 minutes with a mobile phase containing 80% acetonitrile in 0.1% TFA. Under these conditions, native CN and both forms of recombinant CN elute at 41% acetonitrile. The eluted material analyzed by reducing SDS-PAGE showed that VN as a single band with a molecular weight of ~8 kDa, slightly larger than native CN, which agrees with the primary structure containing five additional amino acids. The recovered rCN was almost identical in size to native CN.

HPLC purified rCN and VN were recognized by a polyclonal antisera raised against native CN in both ELISA and Western blotting assays (data not shown).

Example 2

Biological Activity of Recombinant Contortrostatin Constructs

A. In Vitro Functional Assays

The recombinant CN products were evaluated for biological activity by a platelet aggregation inhibition assay. According to this assay, CN binding to GPIIb/IIIa (integrin αIIbβ3) in an RGD dependent manner inhibits ADP induced platelet aggregation (Trikha, Rote et al. 1994). In this assay, potential inhibitors are added to fresh platelet-rich plasma, and after minute, ADP is added to a final concentration of 1 M to induce aggregation. If inhibitor is present, functional aggregation will not occur. The $IC_{50}$ is defined as the concentration at which 50% of the activity is inhibited, and is used as a measure of the potency of an inhibitor.

Figure 9:
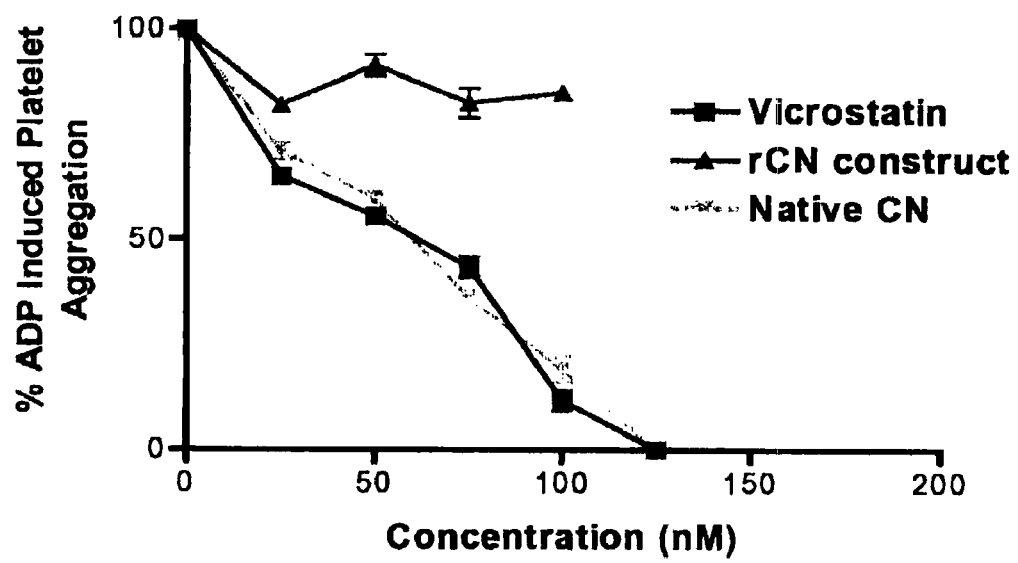
FIG. 9 shows inhibition of ADP-induced platelet aggregation by Vicrostatin (VN), rCN construct, and native CN. Different concentrations of native CN, Vicrostatin (VN), or rCN conformer were incubated with platelet-rich plasma. Addition of ADP induces platelet aggregation; VN, rCN conformer, or native CN were added one minute prior to ADP. Both native CN and VN inhibit aggregation with an $IC_{50}$ of ~60 nM, indicating that VN interacts with platelets identically to native CN. The rCN construct shows platelet inhibitory activity in the micromolar range but not in the nanomolar range.

It was shown that VN exhibited an $IC_{50}$ of 59 nM in the platelet inhibition assay, which is almost identical to that observed for native CN. The rCN conformer however did not inhibit platelet aggregation, even at low µM concentrations which are effective for small, synthetic RGD peptides. The effects of rCN, VN and native CN in the ADP-induced platelet aggregation functional assay are shown in FIG. 9.

Figure 10:
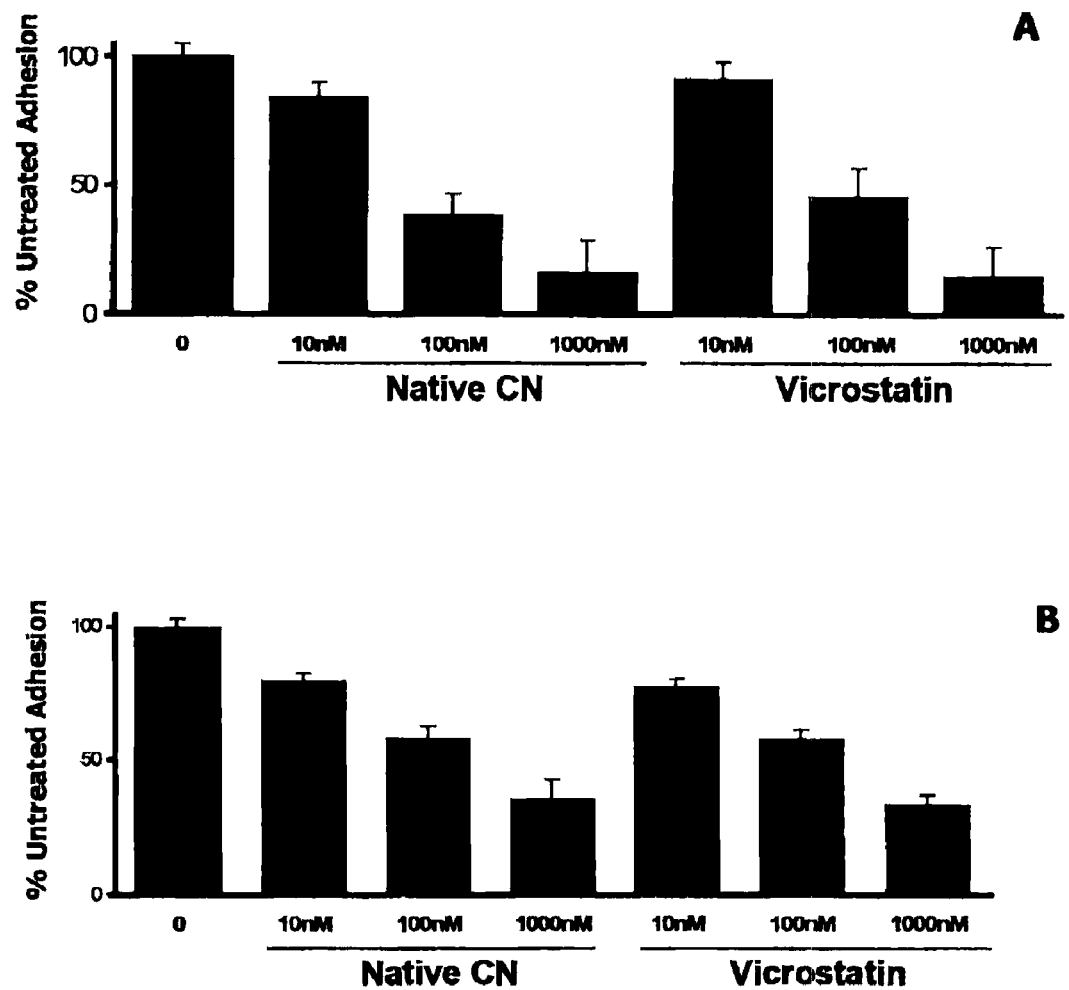
FIG. 10 shows inhibition of MDA-MB-435 breast carcinoma cell adhesion to immobilized fibronectin (Fn) or vitronectin (Vn). Pretreatment of MDA-MB-435 cells (Panel A) with various concentrations (0-1000 nM) of either native CN or VN for 30 min inhibited adhesion of MDA-MB-435 cells (100 μl of cells, $10^5$ cells/ml) to immobilized fibronectin (Fn). Pretreatment of MDA-MB-435 cells (Panel B) with various concentrations (0-1000 nM) of either CN or VN for 30 min inhibited adhesion of MDA-MB-435 cells (100 μl of cells, $10^5$ cells/ml) to immobilized vitronectin (Vn). Pretreated cells were allowed to adhere for 1 hr at 25° C., and after non-adherent cells were washed away, the number of adherent cells for each condition was estimated using the MTS cell viability assay. Vicrostatin (VN) and native CN show a similar inhibitory profile.
Figure 11:
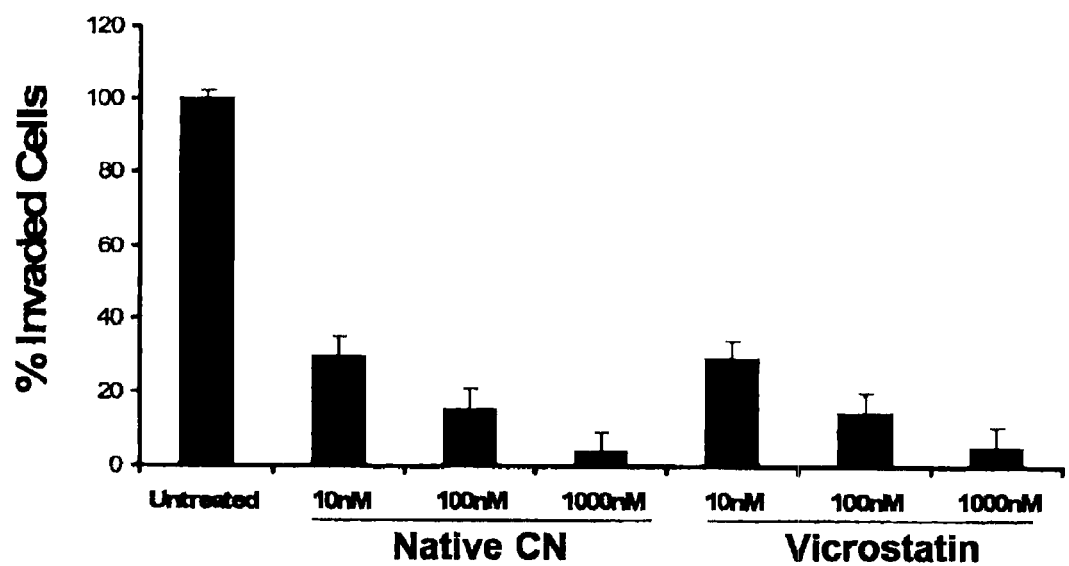
FIG. 11 shows inhibition of MDA-MB-435 breast carcinoma cell invasion through an artificial basement membrane. The cells were incubated in the presence of various concentrations (10, 100, 1000 nM) of either native CN or Vicrostatin for 30 min at 25° C. and then allowed to migrate in the Boyden chamber for 8 hr. Vicrostatin and native CN show a similar inhibitory profile.

Furthermore, the chimeric recombinant disintegrin VN showed similar results in several other in vitro integrin-based functional assays: inhibition of MDA-MB-435 carcinoma cell adhesion to immobilized fibronectin (Fn) and vitronectin (Vn), or inhibition of MDA-MB-435 cell invasion through an artificial basement membrane (Matrigel) in a modified Boyden chamber. For the cell adhesion assay, the pretreatment MDA-MB-435 breast carcinoma cells with various concentrations (0-1000 nM) of either native CN or VN for 30 min inhibited adhesion of MDA-MB-435 cells (100 µl of cells, 105 cells/ml) to either immobilized fibronectin (Fn) or vitronectin (Vn). Pretreated cells were allowed to adhere for 1 hr at 25° C., and after non-adherent cells were washed away, the number of adherent cells for each condition was estimated using the MTS cell viability assay. In the cell invasion assay, an invasion chamber consisting of cell culture inserts that fit into 24-well tissue culture plate has been utilized. The inserts contain an 8 µm-pore size polycarbonate membrane, over which a thin layer of ECMatrix™ was applied. The ECMatrix™ serves as an in vitro reconstituted basement membrane and is a solid gel of ECM proteins prepared from the Engelbreth Holm-Swarm (EHS) mouse tumor. The ECM layer occludes the membranes pores, blocking non-invasive cells to migrate through. The cells were incubated in the presence of various concentrations (10, 100, 1000 nM) of either native CN or Vicrostatin for 30 min at 25° C. and then allowed to migrate in the Boyden chamber for 8 hr. At the 8 hr time point the cells that invaded through the pores into the lower chamber were measured. The numbers of invaded cells for each condition were approximated by quantitating the retrieved labeled DNA using a fluorescent plate reader. The results were calculated in % invasion, where the untreated control was considered as 100% invasion. In all these in vitro functional assays, only Vicrostatin (VN) showed the same potency and exhibited and $IC_{50}$ almost identical to that of native CN (FIGS. 10 and 11). In all in vitro functional assays tested, rCN construct was inactive in the nanomolar range (data not shown).

B. Preparation of Recombinant Disintegrin Containing Liposomes

Figure 12:
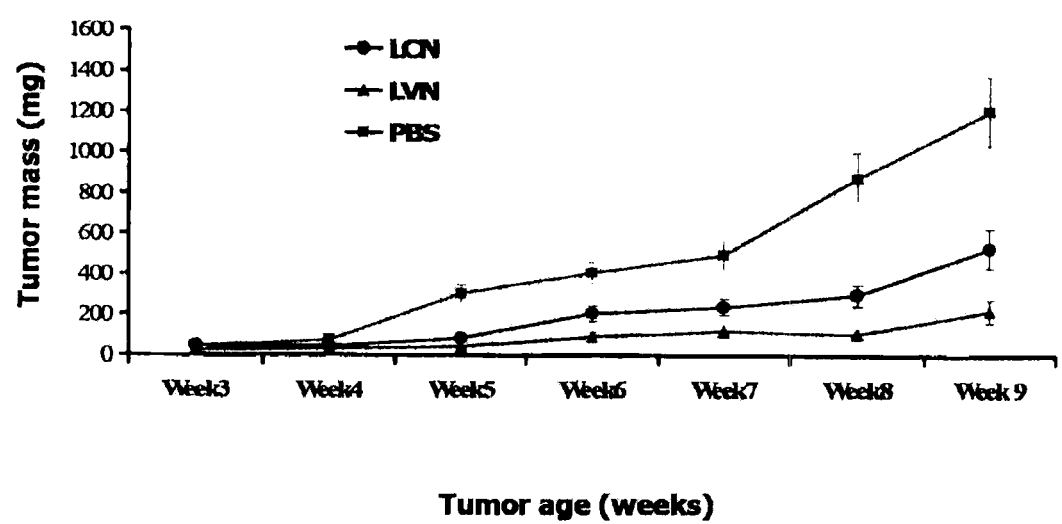
FIG. 12 shows growth of MDA-MB-435 tumors in a mouse xenograft model following administration of native CN and Vicrostatin (VN) containing liposomes: LCN and LVN, respectively. Animals were treated with LCN or LVN (105 μg, twice weekly, i.v. administration). PBS treated control animals were also included. Both T/C values were ~0.27; the tumor growth delay at 400 mg (T-C) was 31 days for each treatment group.

Endotoxin-free VN containing liposomes (referred to as LVN) and endotoxin-free native CN containing liposomes (referred to as LCN) were prepared utilizing a probe sonication previously described (Fujii, Chang et al. 1997). Briefly, the lipids (disteroylphosphatidylcholine, cholesterol and polyethylene glycol derivatized lipid) were dissolved in a chloroform/methanol solution. Thin lipid films were created by pipetting aliquots of the lipid solution into round bottom glass tubes followed by solvent evaporation at 65° C. under a stream of nitrogen gas. The films were placed under vacuum for at least 24 hours to remove residual organic solvent. Liposomes formed following hydration of the lipid films with native CN or VN dissolved in 10 mM sodium phosphate, 9% sucrose, pH 7.2. The mixture was incubated at 65° C. for 5-10 minutes. Hydration was followed by probe sonication until the suspension was translucent. The resultant suspension contained liposomes entrapping CN/VN and unencapsulated CN/VN. The unencapsulated fractions were removed by ultrafiltration. Following clean-up, the suspension was sterilized by passage through a 0.22 μm filter.

The concentration of liposome entrapped CN/VN was determined by disruption of the liposomes with chloroform/methanol/water (10:40:50) followed by centrifugation at 14,000×g. The supernatant was analyzed for CN/VN concentration using BCA protein assay (Smith, Krohn et al. 1985). The encapsulation efficiency was assessed by BCA protein determination following disruption of the LrCN with a solution of $H_2O$:methanol:chloroform.

It was observed that 72% of the recombinant protein VN in the encapsulation solution was entrapped within the liposomes, as compared to 80% with native CN. LVN showed identical stability and size distribution (average particle size 140 nm) as encapsulated native CN.

C. Tumor Therapy Using Recombinant Disintegrin-Containing Liposomes

Biological activity of liposome encapsulated CN was evaluated as previously described (Swenson, Costa et al. 2004). Briefly, three groups of five nude mice had MDA-MB- 435 human mammary carcinoma cells implanted in the mammary fat pad. Two weeks following implantation, small tumors were palpable and treatment was commenced. Animals were treated with LCN or LVN (105 µg, twice weekly, i.v. administration); a PBS treated control was included. A significant inhibitory effect on tumor growth by LVN was observed (FIG. 12). The functional activity of VN was indicated by its in vivo cancer therapeutic effect, which was found to be similar to native CN.

D. Anti-Angiogenic Activity of Recombinant Disintegrin-Containing Liposomes

Previous in vivo studies with native CN and encapsulated native CN (LCN) demonstrated a dramatic inhibitory effect on angiogenesis in growing tumors (Zhou, Nakada et al. 1999; Zhou, Sherwin et al. 2000; Markland, Shieh et al. 2001; Golubkov, Hawes et al. 2003; Swenson, Costa et al. 2004). Consequently, the effect of LVN on tumor angiogenesis in the MDA-MB-435 breast cancer model was examined by histochemical identification of blood vessels with anti-CD31 (anti-PECAM-1) monoclonal antibody. CD31 has been reported to be highly expressed in the angiogenic vasculature with approximately one million copies reported on the surface of endothelial cells (Newman 1994). CD31 also has been reported to be involved with the initial formation and stabilization of cell-cell contacts at lateral junctions of endothelial cells, the maintenance of the vascular permeability barrier, the regulation of cell migration, and the formation of new blood vessels during angiogenesis (Newman, Berndt et al. 1990; Ferrero, Ferrero et al. 1995; DeLisser, Christofidou-Solomidou et al. 1997). These combined properties of CD31 make it an optimal reporter molecule for determinations of angiogenic growth.

Briefly, tumors from treated and untreated mice from the LCN/LVN efficacy studies in the MDA-MB-435 animal tumor model were fixed in 4% normal buffered formalin and embedded in paraffin blocks as previously described (Shi, Key et al. 1991). The paraffin blocks were cut into 5 µm sections and placed on glass slides. Tissue sections underwent deparaffinazation, rehydration, and antigen retrieval as described previously (Pileri, Roncador et al. 1997). Endogenous peroxidase activity was blocked by exposure of the sections to 3% $H_2O_2$. Specimens were blocked with normal goat serum (1:20) for 30 minutes, followed by incubation with the primary antibody for 1 hour. Rabbit monoclonal antibody to CD31 (Sigma) was used as a primary antibody to detect small vessels. The secondary (detection) goat anti-rabbit antibody conjugated with peroxidase (Zymed) was then applied to the samples and incubated for ten minutes at room temperature followed by removal of unbound antibody by multiple washes with PBS. Detection of the secondary antibody using 3,3'-diaminobenzidine (DAB) as the chromogen, was performed following the manufacturers instructions (Zymed HistoMouse Max). Slides were counterstained with hematoxylin. Quantitation of the stained vessels was performed using "hot spot" analysis (Gasparini, Weidner et al. 1993), with "hot spots" being defined as areas of high vessel density (Weidner, Folkman et al. 1992; Swenson, Costa et al. 2004). Areas showing positive staining (100× magnification) were quantitated in terms of pixels within a given hot spot using SimplePCI advanced imaging software (C-Imaging Systems, Cranberry Township, Pa.).

Figure 13:
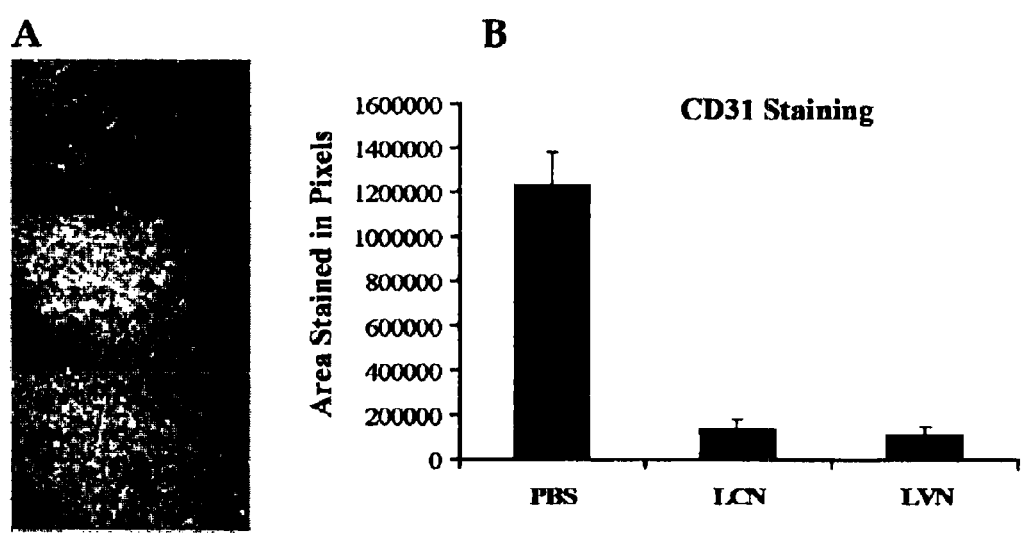
FIGS. 13A and 13B show the anti-angiogenic effects of CN and VN as demonstrated by CD31 immunostaining of tissue sections from MDA-MB-435 tumors taken from xenografted mice treated with CN and VN containing liposomes.

Vessel detection by CD31 in MDA-MB-435 tumor sections is shown in FIGS. 13A and 13B. A bar graph summary in FIG. 14B indicates differences in positive staining in each of the treatment groups: PBS, intravenous liposomal encapsulated native CN (LCN) and intravenous liposomal encapsulated VN (referred to as LVN). In both the LCN, and LVN treated tumors, there is a statistically significant (p<0.0005) reduction of microvascular density, which corresponds to a 90% reduction in angiogenesis in the LCN group and 92% reduction in the LVN group. The reduction in angiogenesis, as observed by CD31 immunostaining in all treatment groups in the MDA-MB-435 breast cancer xenograft model indicates that LVN is an effective inhibitor of angiogenesis.

E. Structural Analysis of Recombinant Disintegrin

Figure 14A:
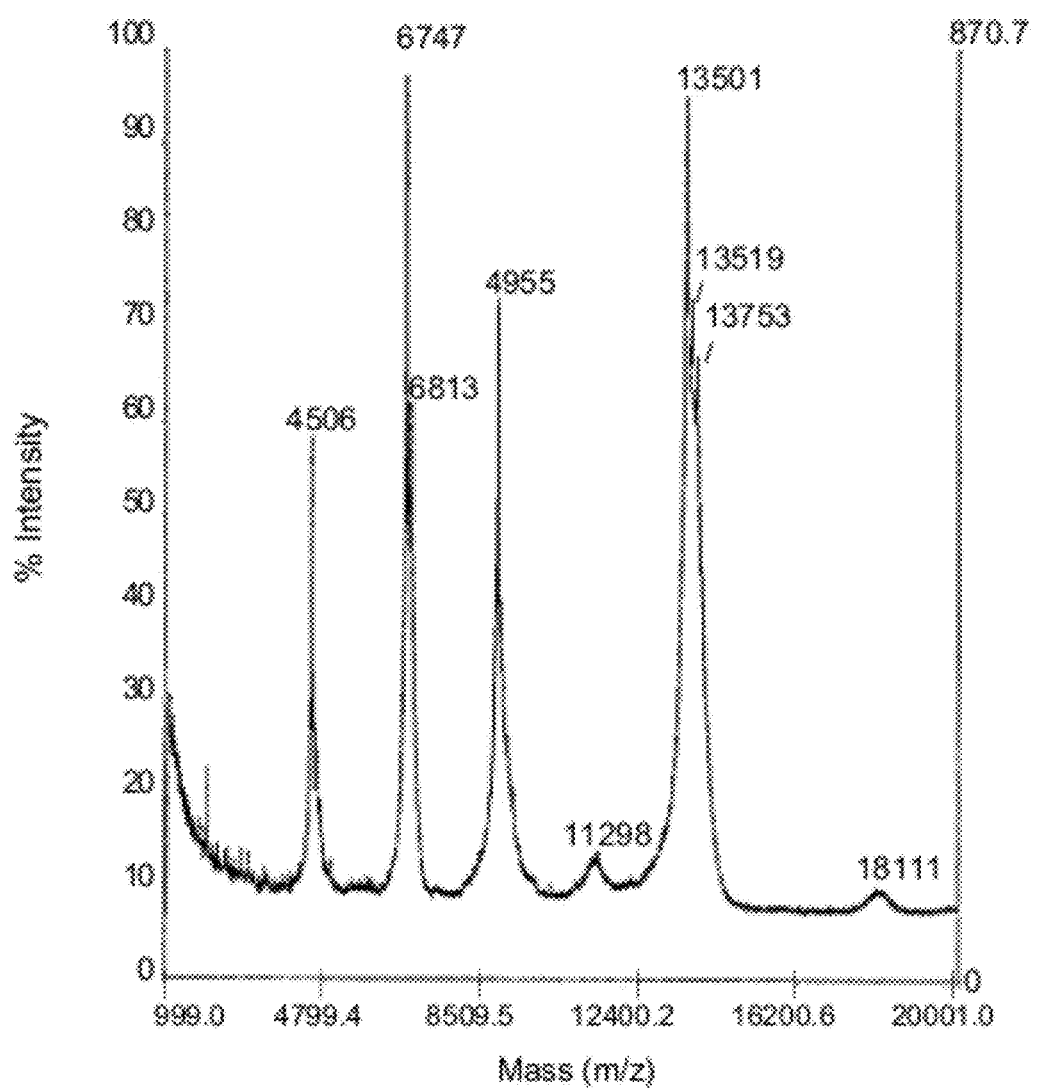
Figure 14B:
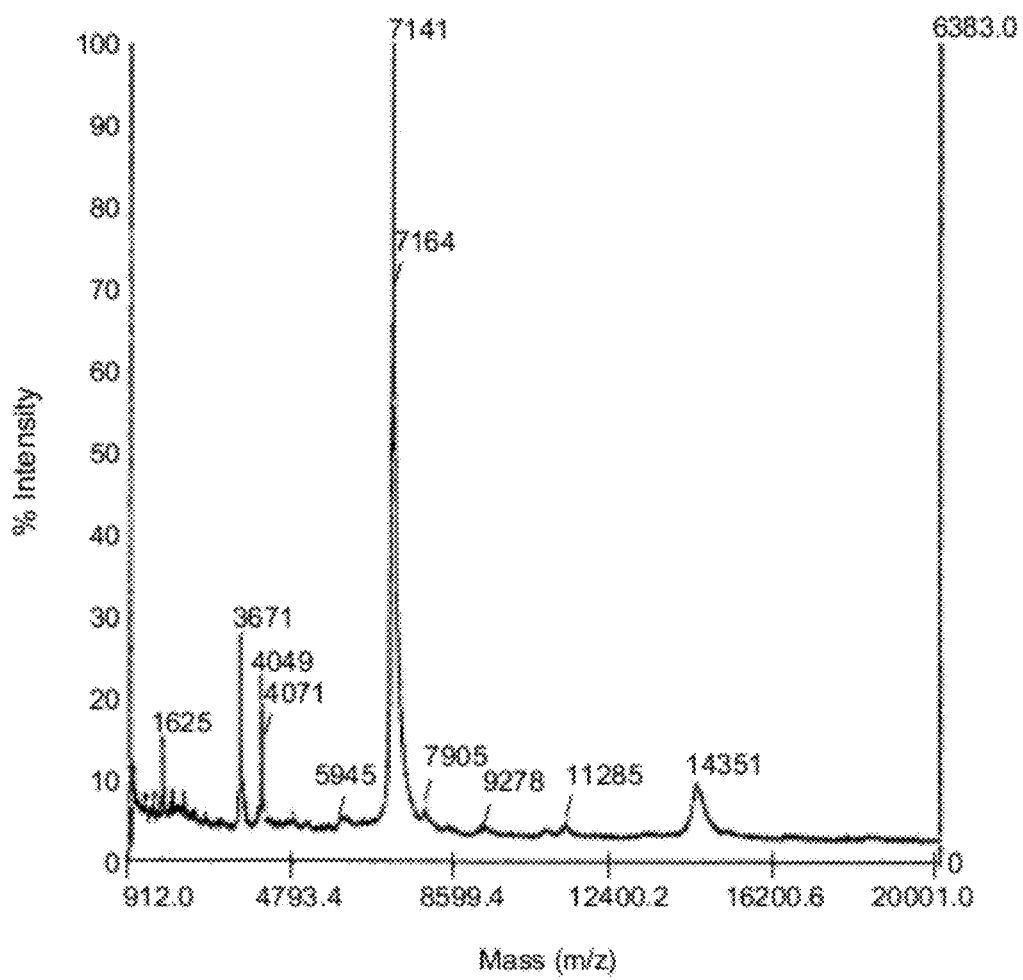
FIG. 14B shows quantitation of stained microvessels with LCN showing 90% inhibition and LVN showing 92% inhibition of tumor-induced angiogenesis (both compared to the PBS treated control animals).

The structure of native CN and VN was evaluated by mass spectrometry. MALDI-TOF mass spectrometry was performed using a matrix of α-cyano-4-hydroxycinnamic acid. Native CN with MALDI-TOF is shown in FIG. 14A and VN with MALDI-TOF is shown in FIG. 14B (a monomeric peak with Mr of 7143.41 is seen). These results indicate that VN is a monomer rather than a dimer as observed for native CN.

Electron spray ionization mass spectrometry was also used to evaluate native CN and VN. FIG. 15A shows a big peak of 13507.0, for CN representing the dimer, and two smaller peaks probably CN from which a single amino acid has been cleaved. FIG. 15B shows a single peak of 7146.0, for VN, confirming that it is a monomer.

Mass spectrometry data showed that VN is a monomeric structure unlike the dimer form of native CN. Because the biological activities measured for CN as described above reside in the C-terminal portion of the molecule, this indicates that VN folded correctly at least in the C-terminal part of the molecule, making the correct disulfide bridge combinations and preserving the integrin binding loop that exists in the native conformer. However, the failure to obtain the native dimer configuration indicates that the N-terminal portion of VN folded in a different manner than native CN, which compromised the ability of the N-terminal cysteines of VN to participate in intermolecular disulfide bond formation. This was confirmed by the detection of at least one free thiol in VN. The first cysteine residue (Cys-7) which pairs in the native state with the seventh cysteine (Cys-30) in CN are the furthest apart of the cysteines that bridge in CN. Difficulty inherent in bridging the C7 and C30 cysteines in CN is a possible explanation for the failure of VN to form dimers.

Example 3

Optimizing Codon Usage

A potential issue with Origami *E. coli* strain (FA113) is its lack of codon usage optimization. In many organisms, not all of the 61 tRNA species are used equally. The so-called major codons are those that occur in highly expressed genes, whereas the minor or rare codons tend to be in genes expressed at lower levels. Which of the 61 codons are the rare ones depends strongly on the organism.

Eukaryotic proteins tend to translate inefficiently in *E. coli* because of mismatched codon use that hampers protein production in heterologus expression systems (Makrides 1996). The codon usage per organism can be found in codon usage databases well known in the art and available online. The codon usage in *E. coli* is shown in FIG. 16. Genes in this figure are clustered into three classes. Class I genes are involved in most metabolic processes. Class II genes correspond to genes highly and continuously expressed during exponential growth. Class III genes are implicated in horizontal transfer of DNA. The distribution of codons in class III genes is more or less even, whereas it is extremely biased in class II genes—in particular, codons terminated in A are selected against—(Guerdoux-Jamet, Henaut et al. 1997). Usually, the frequency of the codon usage reflects the abundance of their cognate tRNAs. Therefore, when the codon usage of the protein to be expressed differs significantly from the average codon usage of the expression host, this could cause problems during expression.

The following codon usage problems may be encountered:
interrupted translation—which leads to a variety of truncated protein products
frame shifting—which lead to mistranslation of protein products
misincorporation of amino acids—for instance, lysine for arginine as a result of the AGA codon, and this can be detected by mass spectrometry since it causes a decrease in the molecular mass of the protein of 28 Da
inhibition of protein synthesis and cell growth—significantly affecting the expression yield As a consequence, the observed levels of expression are often low or even undetectable. Especially in cases where rare codons are present at the 5'-end of the mRNA or where consecutive rare codons are found, expression levels are low and truncated protein products are generated. The 8 least used codons in various organisms are compared in FIG. 17.

For the CN gene, there are 39 codons represented in bold in FIG. 18A that are rarely used in *E. coli*, making CN native gene codon usage difficult with this expression system. Another *E. coli* expression host from Novagen, Rosetta-gami B, optimizes the codon usage by providing tRNA supplementation for AGA, AGG, GGA, ATA, CTA and CCC ones, but not for CGG or ACA. Accordingly, even with the use of the enhanced bacterial host Rosetta-gami B, the CN gene still has two codons for which this heavily engineered *E. coli* provides inadequate support. The CGG is a classical rare codon and thus is preferably replaced in the DNA sequence. The ACA codon codes for threonine, albeit not as rarely used as the rare classified ones (see FIG. 18A), is important because it is very well represented in the native CN gene (there are eleven ACA codons in the encoding sequence). Thus, the ACA codons should be replaced in the coding sequence where possible.

In some embodiments, 8 out of the 11 ACA codons in the disintegrin domain of the CN gene are replaced with homologues more compatible with the host. By using a set of overlapping oligonucleotide primers, the two groups of codons were replaced by PCR (site-directed mutagenesis) to the more used homologues (CGT and ACC/ACT, respectively). The mutated CN gene sequence built by PCR is represented in FIG. 17B. In this figure, the codons shown in bold are the only ACA codons not replaced.

The following overlapping oligonucleotide primers were generated and used to replace the CGG and ACA codons in the wild type CN gene as described above:

CNCGGfor—CN disintegrin domain forward primer that replaces CGG and the eleventh ACA codons:
5'ACCGTATGCCGTAGAGCAAGGGGTGAT-GACCTGGATGATTAC3' (SEQ ID NO: 9)
CNCGGback—CN disintegrin domain reverse primer that replaces CGG and the eleventh ACA codons:
5'TGCTCTACGGCATACGGTTCCT-TCTTTCATAAATTTGCACTG3' (SEQ ID NO: 10)
CNACAfor—CN disintegrin domain forward primer that replaces the eight, ninth and tenth ACA codons:
5'TGCGATGCTGCAACCTGTAAACTGAC-CACCGGGTCACAGTGTGCAGAT3' (SEQ ID NO: 11)
CNACAback—CN disintegrin domain reverse primer that replaces the eight, ninth and tenth ACA codons:
5'CAGTTTACAGGTTGCAGCATCGCAG-CACGGATTTGC3' (SEQ ID NO: 12)

CNMACA 2for—CN metalloprotease domain forward primer that replaces the first two ACA codons:
5'TCTGATGGCAGAAAAATTACCACCAAC-CCTCCGGTTGAG3' (SEQ ID NO: 13)
CNMACA12back—CN metalloprotease domain reverse primer that replaces the first two ACA codons:
5'AATTTTTCTGCCATCAGAGGAATAATG3' (SEQ ID NO: 14)
CNMACA45for—CN metalloprotease domain forward primer that replaces the fourth and fifth ACA codons:
5'CATAGTGCAATAAATCTTTGGGTTG-CAGTTACTATGGCCCATGAG3' (SEQ ID NO: 15)
CNMACA45back—CN metalloprotease domain reverse primer that replaces the fourth and fifth ACA codons:
5'ATTTATTGCACTATGATCCTGAACAAT-TCCGGTAGAAAGCTTCGG3' (SEQ ID NO: 16)

Example 4

Engineered Hosts System

Figure 19:
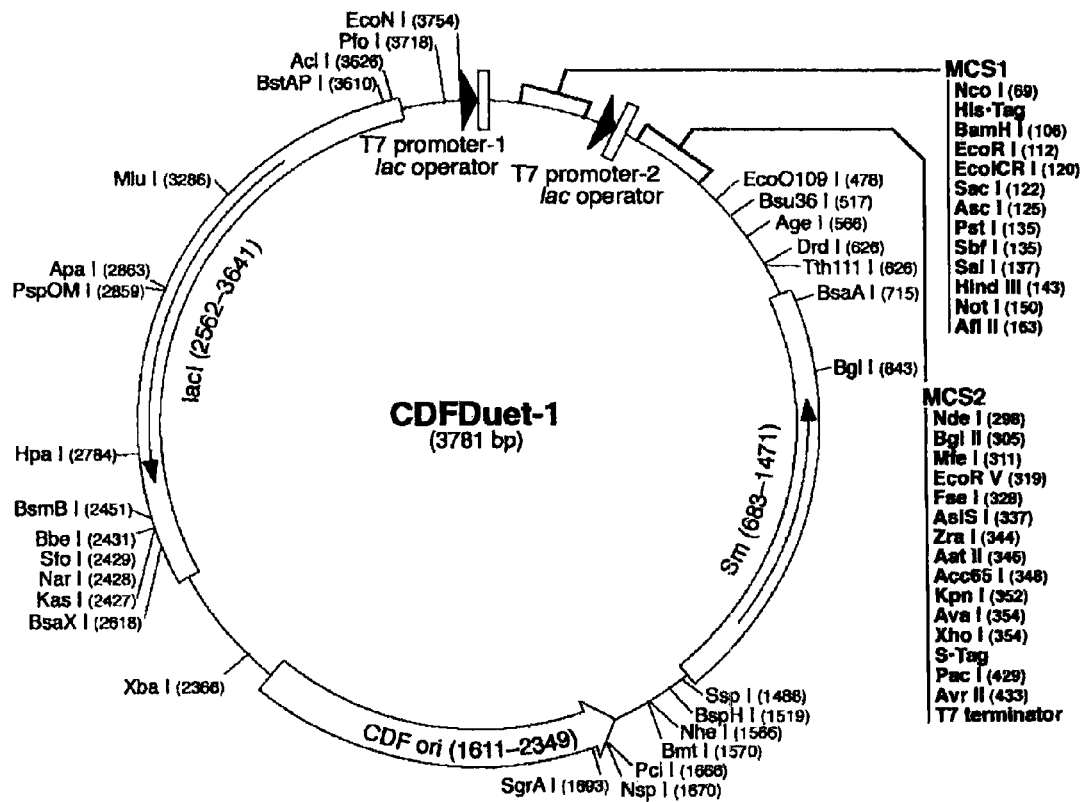
FIG. 19 is a map of the pCDFDuet-1 vector (from Novagen).

An engineered Rosetta-gami B host with disulfide isomerase activity in the cytoplasm and including auto-regenerating capabilities for its oxido-reductive enzymatic equipment in the same compartment may be used for recombinant CN production in bacteria. The host can be engineered to concomitantly overexpress in its cytoplasm the disulfide containing eukaryotic protein fused to thioredoxin along with ΔssDsbC and ΔssDsbDα. This goal can be achieved using a pair of vectors that can coexist together in the same system. The minimum features of this vector set are: the presence of a strong promoter like T7lac, that can be used for all 3 proteins simultaneously, as well as the presence of convenient multiple restriction sites in different MCSs (multiple cloning sites) incorporated in the vectors. Two Novagen vectors (pET32a and pCDFDuet-1) that are compatible with each other by having different replicons, and also compatible with Rosetta-gami expression host, have the afore-mentioned characteristics and may be used in the system described herein. By employing these two vectors, the scenario of using an integrated system, in which the expression of all 3 proteins would be simultaneously controlled by a single strong promoter T7lac, is achieved. The map of pCDFDuet-1 vector as provided by Novagen is shown in FIG. 19.

Several wild type and active site mutated thioredoxin-CN genetic constructs were prepared which express a fusion protein containing thioredoxin at the N-terminus and disintegrin domain (CN), or with the disintegrin domain including echistatin C-terminal graft (VN), or with larger eukaryotic proteins consisting of proprotein, metalloproteinase and disintegrin domains of CN with or without the echistatin C-terminal graft (designated rCN PMD and VN PMD). The broad term "TrxA-disintegrin construct" used below refers to the following constructs prepared as described herein: TrxA-rCN (thioredoxin A fused to CN disintegrin domain), TrxA-VN (thioredoxin A fused to CN disintegrin domain including echistatin C-terminal graft), TrxA-rCN PMD (thioredoxin A fused to a large protein consisting of CN proprotein, metalloproteinase and disintegrin domains), TrxA-VN PMD (thioredoxin A fused to a large protein consisting of CN proprotein, metalloproteinase and disintegrin domains with echistatin C-terminal graft), TrxA (CPYC)-rCN(CPYC disclosed as SEQ ID NO: 49) (an active site mutated thioredoxin A with the CPYC (SEQ ID NO: 49) motif fused to CN disintegrin domain), TrxA (CPYC)-VN(CPYC disclosed as SEQ ID NO: 49) (an active site mutated thioredoxin A including the CPYC (SEQ ID NO: 49) motif fused to CN disintegrin domain with echistatin C-terminal graft), TrxA (CPYC)-rCN PMD (CPYC disclosed as SEQ ID NO: 49) (an active site thioredoxin A including the CPYC (SEQ ID NO: 49) motif fused to a large protein consisting of CN proprotein, metalloproteinase and disintegrin domains), TrxA (CPYC)-VN PMD (CPYC disclosed as SEQ ID NO: 49) (an active site thioredoxin A including the CPYC (SEQ ID NO: 49) motif fused to a large protein consisting of CN proprotein, metalloproteinase, and disintegrin domains with echistatin C-terminal graft), TrxA (CGHC)-rCN(CGHC disclosed as SEQ ID NO: 50) (an active site mutated thioredoxin A including the CGHC (SEQ ID NO: 50) motif fused to CN disintegrin domain), TrxA (CGHC)-VN (CGHC disclosed as SEQ ID NO: 50) (an active site mutated thioredoxin A including the CGHC (SEQ ID NO: 50) motif fused to CN disintegrin domain with echistatin C-terminal graft), TrxA (CGHC)-rCN PMD (CGHC disclosed as SEQ ID NO: 50) (an active site mutated thioredoxin A including the CGHC (SEQ ID NO: 50) motif fused to a large protein consisting of CN proprotein, metalloproteinase and disintegrin domains), and TrxA (CGHC)-VN PMD (CGHC disclosed as SEQ ID NO: 50) (an active site mutated thioredoxin A including the CGHC (SEQ ID NO: 50) motif fused to a large protein consisting of CN proprotein, metalloproteinase and disintegrin domains with echistatin C-terminal graft).

To increase the stability of some recombinant eukaryotic protein transcripts in the cytoplasm of the expression host, especially of those large transcripts containing the proprotein, metalloprotease and disintegrin domains (with or without echistatin C-terminal graft), some recombinant constructs were designed to include nucleotide sequences of various length that can normally be found in the 3' non-translatable regions of CN native mRNA, downstream of the stop codon signaling the end of translation found in the CN native transcript. Several disintegrin constructs were cloned with extra non-coding nucleotide regions modeled from CN native mRNA by using CN cDNA as a template (Zhou, Hu et al. 2000). Native CN cDNA is available in Francis S. Markland laboratory at USC.

The primers that were used to PCR clone downstream of TrxA nucleotide sequence, the CN disintegrin domain sequence with or without the echistatin C-terminal graft or the larger CN sequences consisting of proprotein, metalloprotease, and disintegrin domains with or without echistatin C-terminal graft into the pET32a vector were the following:

CNfor2—forward primer for CN disintegrin domain introducing the NcoI restriction site and the TEV protease cleavage site:
5'GTTCCCCATGGATGAGAATCTTTACTTC-CAAGGAGACGCTCCTGCAAATCCGTGC TGCGAT-GCTGCA3' (SEQ ID NO: 17)

CNfor3—forward primer for full-length CN introducing the NcoI restriction site and the TEV protease cleavage site:
5'GTTCCCCATGGATGAGAATCTTTACTTC-CAAGGAATGATCCAGGTTCTCTTGGTG ACTCTAT-GCTTA3' (SEQ ID NO: 18)

CNback3—reverse primer for CN constructs without echistatin C-terminal graft introducing the EcoRI restriction site:
5'GTTATTCGGAATTCTTAGGCATGGAAGG-GATTTCTGGGACAGCCAGCAGA3' (SEQ ID NO: 19)

CNback4—reverse primer for CN constructs with echistatin C-terminal graft introducing the EcoRI restriction site:
5'GTTATTCGGAATTCTTAAGTAGCTGGAC-CCTTGTGGGGATTTCTGGGACAGCCAG CAGATAT-GCC3' (SEQ ID NO: 20)

The reverse primers used to clone various disintegrin constructs including the non-translatable nucleotide sequences of CN native mRNA into the pET32a vector were the following:

CNback5—reverse primer for generating CN native transcripts introducing the EcoRI restriction site:
5'GTTATTCGGAATTCATATTACA-GAATTTGGATACCATCTGGAAGCTA3' (SEQ ID NO: 21)

CNback6—reverse primer for generating CN native transcripts introducing the EcoRI restriction site:
5'GTTATTCGGAATTCGAATGAGAAT-AGTTTGTTTATTGACGGAAGCAG3' (SEQ ID NO: 22)

The oligonucleotide primers that were used to amplify the active-site thioredoxin mutants and clone them into pET32a vector replacing the wild type TrxA nucleotide sequence were the following:

Trxfor—Trx forward external primer introducing the XbaI restriction site and designed for inserting the 5' end of the active site mutants into pET32a vector:
5'CCCCTCTAGAAATAATTTTGTTTAACT3' (SEQ ID NO: 23)

Trxback—Trx reverse external primer introducing the BglII restriction site and designed for inserting the 3' end of the active site mutants into pET32a vector:
5'TACCCAGATCTGGGCTGTCCATGTGCT3' (SEQ ID NO: 24)

TrxGrxfor—Trx forward primer that mutates TrxA active site to a glutaredoxin-like one:
5'TTCTGGGCAGAGTGGTGCCCGTATTG-CAAAATGATCGCCCCG3' (SEQ ID NO: 25)

TrxGrxback—Trx reverse primer that mutates TrxA active site to a glutaredoxin-like one:
5'GCACCACTCTGCCCAGAAATC3' (SEQ ID NO:26)

TrxPDIfor—Trx forward primer that mutates TrxA active site to a PDI-like one:
5'TTCTGGGCAGAGTGGTGCGGTCATTG-CAAAATGATCGCCCCG3' (SEQ ID NO: 27)

TrxPDIback—Trx forward primer that mutates TrxA active site to a PDI-like one:
5'GCACCACTCTGCCCAGAAATC3' (SEQ ID NO: 28)

For DsbD cloning, the restriction sites employed were NcoI/EcoRI. This restriction enzyme pair was used because it removed the His tag-sequence from the pCDFDuet-1 vector first multiple cloning site, so ΔssDsbD α-domain would be expressed as a non-tagged molecule. For DsbC cloning the NdeI/XhoI restriction enzyme pair was used, so that ΔssDsbC protein would be expressed un-tagged.

Wild type DsbC gene carries an EcoRI restriction site. For this reason, the foldase sequences were cloned by PCR in a stepwise manner as following: the ΔssDsbD α-domain nucleotide sequence was inserted in one multiple cloning site of pCDFDuet-1 vector in the first cloning step, followed by ΔssDsbC nucleotide sequence, which was inserted in the other multiple cloning site of the vector in a second cloning step. The only His-tagged proteins expressed in the system described herein were the TrxA-disintegrin fusion constructs, so they can be easily separated from the other 2 co-overexpressed proteins by employing the Ni-column chromatography purification technique. All TrxA-disintegrin constructs included a TEV protease cleavage-site engineered just upstream of the disulfide containing recombinant protein (eukaryotic protein) nucleotide sequences. All purification steps of TrxA-disintegrin constructs were performed in the identical manner to those described in the section discussing the Origami system. However, some TrxA-disintegrin constructs also carried a formic acid cleavage site (Asp-Pro) instead of a TEV protease cleavage site, also engineered just upstream of the N-terminus of disulfide containing recombinant eukaryotic protein nucleotide sequences. Use of formic acid for hydrolysis reduces costs as compared with other protease cleavage systems such as the TEV proteolysis system.

The oligonucleotide primers that were used to clone various disintegrin constructs engineered to carry an Asp-Pro formic acid cleavage site just upstream of the N-terminus of various CN constructs (with or without multiple domains or echistatin C-terminal graft) into pET32a vector were the following:

CNfor4—forward primer for CN disintegrin domain introducing the NcoI restriction site and the Asp-Pro cleavage site:
5'GTTCCCCATGGATGACCCTGCAAATC-CGTGCTGCGATGCTGCAACA3' (SEQ ID NO: 29)
CNfor5—forward primer for full-length CN introducing the NcoI restriction site and the Asp-Pro cleavage site:
5'GTTCCCCATGGATGACCCTATGATCCAG-GTTCTCTTGGTGACTCTATGCTTA3' (SEQ ID NO: 30)

The oligonucleotide primers that were used to PCR clone the ΔssDsbC, ΔssDsbD α-domain nucleotide sequences as well as their active-site mutants sequences into pCDFDuet-1 vector were the following:

DsbCUP—DsbC forward primer introducing the NdeI restriction site:
5'GTATTCATATGGATGACGCGGCAAT-TCAACAAACGTTA3' (SEQ ID NO: 31)
DsbCDN—DsbC reverse primer introducing the XhoI restriction site:
5'GTTCCCTCGAGTTATTTACCGCTGGT-CATTTTTTGGTG3' (SEQ ID NO: 32)
DsbDUP—DsbD forward primer introducing the NcoI restriction site:
5'GTTATTCGCCATGGGATTATTC-GACGCGCCGGGACGTTCA3' (SEQ ID NO: 33)
DsbDDN—DsbD reverse primer introducing the EcoRI restriction site:
5'GTCTACGAATTCGCTTAAGGCTGTG-GCGCTGCGTTGTTGGC3' (SEQ ID NO: 34)

The overlap extension oligonucleotide primers that were used to generate the DsbC active site mutants were the following:

DsbCTFfor—active site mutated DsbC (CTFC) (SEQ ID NO: 46) overlap extension forward primer:
5'TTTACTGATATTACCTGTACCTTCTGC-CACAAACTGCATGAG3' (SEQ ID NO: 35)
DsbCGFfor—active site mutated DsbC (CGFC) (SEQ ID NO: 45) overlap extension forward primer:
5'TTTACTGATATTACCTGTGGTTTCTGC-CACAAACTGCATGAG3' (SEQ ID NO: 36)
DsbCOEback—active site mutated DsbC overlap extension backward primer:
5'ACAGGTAATATCAGTAAACAC3' (SEQ ID NO:37)

The pET32a and pCDFDuet-1 external and internal oligonucleotide primers that were employed for sequencing were the following:
DuetCDFUP1:
5'GGATCTCGACGCTCTCCCTTA3' (SEQ ID NO: 38)
DuetCDFUP2:
5'TTGTACACGGCCGCATAATCG3' (SEQ ID NO: 39)
DuetCDFDN1:
5'CGATTATGCGGCCGTGTACAA3' (SEQ ID NO: 40)
PETUP1:
5'GGAATTGTGAGCGGATAACAATTC3' (SEQ ID NO: 41)
PETUP2:
5'CGCGGTTCTGGTATGAAAGAAACC3' (SEQ ID NO: 42)
PETDN1:
5'GTTATGCTAGTTATTGCTCAGCGG3' (SEQ ID NO: 43)

The bacterial thiol-disulfide interchange protein DsbD α-domain and disulfide isomerase DsbC nucleotide sequences were directly amplified by PCR from E. coli K-12 MG1655 strain genomic DNA prepared and purified in the Francis S. Markland laboratory at the University of Southern California, using the afore-mentioned oligonucleotide primers. The CN sequences were amplified by PCR from plasmids and/or mutated first to replace all native codons that were rarely used in bacteria or those for which Rosetta-gami B did not provide support. The CN nucleotide sequence encompassing the proprotein, metalloproteinase and disintegrin domain was mutated by utilizing the site-directed mutagenesis technique, employing the overlap extension oligonucleotide primers in several PCR steps.

Following PCR amplification of the wild type full-length CN nucleotide sequence and replacement of optimized codons was completed, and all foldases sequences amplified (with or without active site mutations), these sequences were cloned into pET32a and pCDFDuet-vectors in a stepwise manner. The full-length CN nucleotide sequence with replaced codons further served as templates to build the disintegrin constructs including the echistatin C-terminal graft. The wild type TrxA, the disintegrin nucleotide sequences with or without the echistatin C-terminal graft were directly inserted into the pET32a vector using the BglII/NcoI restriction sites. To build the TrxA-disintegrin constructs with TrxA active site mutants, the TrxA mutants were first separately amplified using the overlap extension primers and then inserted in the pET32a vector to replacing the wild type TrxA sequence using the XbaI/BglII set of restriction enzymes. The pET32a vector including the wild type TrxA nucleotide sequence was used as a template for all the PCR amplification steps necessary to generate TrxA active site mutants. In a further step, after the active site TrxA mutants were inserted into the vector, the disintegrin nucleotide sequences were also inserted in pET32a, by employing the NcoI/EcoRI set of restriction enzymes.

The following active site Trx A mutants were used in the expression system described herein: glutaredoxin-like TrxA (thioredoxin A with a bacterial glutaredoxin A active site) and PDI-like TrxA (thioredoxin A with a eukaryotic protein disulfide isomerase active site).

The active site mutated sequences of ΔssDsbC were directly amplified by PCR from E. coli K-12 MG1655 strain genomic DNA using the overlap extension primers. The following active-site mutants were used in the expression system described herein: ΔssDsbC (CGFC) (SEQ ID NO: 45), and ΔssDsbC (CTFC) (SEQ ID NO: 46). The wild type nucleotide sequences of ΔssDsbD α-domain and ΔssDsbC or the active site mutated sequences of ΔssDsbC were cloned into separate multiple cloning sites of pCDFDuet-1 vector using two sets of restriction enzymes: NcoI/EcoRI and NdeI/XhoI respectively. The pETDuet-1 and pCDFDuet-1 vector constructs were used to co-transform electrocompetent DH5α cells that are further amplified in culture. All constructs were then validated by sequencing and the recombinant plasmids further used to co-transform the Rosetta-gami B expression host.

All growing steps were the same as those previously described for the Origami system, except for the antibody usage. The Rosetta-gami B co-transformants were grown in five antibiotics: carbenicillin (100 μg/mL), spectinomycin (50 μg/mL), tetracycline (12.5 μg/mL), kanamycin (15 μg/mL) and chloramphenicol (34 μg/mL). All processing and purification step of various recombinant proteins were identical to those previously described for the Origami system.

The production level and the biological activity of recombinant disintegrin variants with different co-overexpressed foldases are initially determined after employing the following expression combinations:
1. TrxA-disintegrin+ΔssDsbC+ΔssDsbDα
2. TrxA (CPYC)-disintegrin+ΔssDsbC+ΔssDsbDα (CPYC disclosed as SEQ ID NO: 49)
3. TrxA (CGHC)-disintegrin+ΔssDsbC+ΔssDsbDα (CGHC disclosed as SEQ ID NO: 50)

By comparing the structures and yields of different TrxA-disintegrin fusion proteins, the version that generates the properly folded dimer at the best level of expression is chosen. To further improve the expression level of correctly folded proteins, the best oxidase version, referred to as "best oxidase-disintegrin", is further tested in combination with two mutated variants of DsbC.
4. Best oxidase-disintegrin+ΔssDsbC (CGFC)+ΔssDsbDα (CGFC disclosed as SEQ ID NO: 45)
5. Best oxidase-disintegrin+ΔssDsbC (CTFC)+ΔssDsbDα (CTFC disclosed as SEQ ID NO: 46)

For production of recombinant disintegrins the same steps described in Example 1 were employed. However, the expressed recombinant variants including the proprotein, metalloproteinase and disintegrin domains may undergo a post-translational autocatalytical proteolysis freeing the C-terminal recombinant disintegrin domains with or without echistatin C-terminal graft, disintegrin domains that can be further purified directly from the total soluble protein fraction retrieved form bacteria by reverse-phase HPLC. This desirable event would obviate the need for Ni-column affinity chromatography purification and TEV-protease proteolysis or formic acid hydrolysis intermediary steps employed in recombinant disintegrin production.

Example 5

Optimizing Expression

The system can be optimized to achieve better yields by changing several parameters such as the use of: increased concentrations of carbenicillin (a more stable form of penicillin) that is more resistant to β-lactamase degradation for all growing steps; an optimal IPTG concentration (a feature that can be easily achieved in a Tuner derivative host); and, finally, an optimal induction temperature for generating the best yields. The simplest way to achieve a more homogenous culture and prevent the plasmid loss is to use the more stable antibiotic carbenicillin may be used rather than ampicillin. For tighter regulation of basal expression, a phenomenon that also leads to plasmid instability, the culture medium may be supplemented with 1% glucose to repress induction of the lac promoter by lactose, which is present in most rich media (such as LB). Moreover, addition of small quantities of ethanol, of polyols and sucrose, or low molecular weight thiols can be used to significantly boost the expression of soluble proteins in E. coli (e.g. from several milligrams of recombinant protein to tens or even hundreds of milligrams). Also, codon optimization can be used as already discussed. In an effort to optimize the codon usage, the Rosetta-gami B(DE3) pLysS expression host, a strain supplemented with rare tRNAs, may be preferentially employed instead of Origami B(DE3)pLysS.

Example 6

Expression System Combinations

The following elements may be used in the methods of the invention. "TP" means eukaryotic protein.
1. TrxA-TP or TrxA (CPYC)-TP or TrxA (CGHC)-TP (CPYC and CGHC disclosed as SEQ ID NOS: 49 and 50, respectively)
2. Integrin binding (e.g. HKGPAT; SEQ ID NO: 47) C-terminal sequence for TP
3. "Tag" sequence for item no. 1.
4. Cleavage site sequence for item no. 1.
5. ΔssDsbC
6. ΔssDsbDα
7. trxB mutant
8. gor mutant
9. ompT mutant
10. ion mutant The methods may include any combination of 1-10 above for expressing TP. In another approach, any of the following elements may be combined for expressing a eukaryotic protein that is not fused to thioredoxin.
1. Eukaryotic protein unfused to thioredoxin
2. Integrin binding (e.g. HKGPAT; SEQ ID NO: 47) C-terminal sequence for TP
3. Tag sequence for item no. 1.
4. Cleavage site sequence for item no. 1.
5. ΔssDsbC
6. ΔssDsbDα
7. trxB mutant
8. gor mutant
9. ompT mutant
10. ion mutant

REFERENCES

Bader, M., W. Muse, et al. (1999). "Oxidative protein folding is driven by the electron transport system." *Cell* 98(2): 217-27.

Bader, M. W., T. Xie, et al. (2000). "Disulfide bonds are generated by quinone reduction." *J Biol Chem* 275 (34): 26082-8.

Bardwell, J. C., J. O. Lee, et al. (1993). "A pathway for disulfide bond formation in vivo." *Proc Natl Acad Sci USA* 90 (3): 1038-42.

Bardwell, J. C., K. McGovern, et al. (1991). "Identification of a protein required for disulfide bond formation in vivo." *Cell* 67 (3): 581-9.

Becker, G. W. and H. M. Hsiung (1986). "Expression, secretion and folding of human growth hormone in *Escherichia coli*. Purification and characterization." *FEBS Lett* 204(1): 145-50.

Bessette, P. H., F. Aslund, et al. (1999). "Efficient folding of proteins with multiple disulfide bonds in the *Escherichia coli* cytoplasm." *Proc Natl Acad Sci USA* 96(24): 13703-8.

Bessette, P. H., J. Qiu, et al. (2001). "Effect of sequences of the active-site dipeptides of DsbA and DsbC on in vivo folding of multidisulfide proteins in *Escherichia coli*." *J Bacteriol* 183(3): 980-8.

Bilgrami, S., S. Tomar, et al. (2004). "Crystal structure of schistatin, a disintegrin homodimer from saw-scaled viper (*Echis carinatus*) at 2.5 A resolution." *J Mol Biol* 341 (3): 829-37.

Calvete, J. J., M. Jurgens, et al. (2000). "Disulphide-bond pattern and molecular modelling of the dimeric disintegrin EMF-10, a potent and selective integrin alpha5beta1 antagonist from *Eristocophis macmahoni* venom." *Biochem J* 345 Pt 3: 573-81.

Collet, J. F. and J. C. Bardwell (2002). "Oxidative protein folding in bacteria." *Mol Microbiol* 44(1): 1-8.

Collet, J. F., J. Riemer, et al. (2002). "Reconstitution of a disulfide isomerization system." *J Biol Chem* 277(30): 26886-92.

DeLisser, H. M., M. Christofidou-Solomidou, et al. (1997). "Involvement of endothelial PECAM-1/CD31 in angiogenesis." *Am J Pathol* 151 (3): 671-7.

Dubendorff, J. W. and F. W. Studier (1991). "Controlling basal expression in an inducible T7 expression system by blocking the target T7 promoter with lac repressor." *J Mol Biol* 219(1): 45-59.

Ferrero, E., M. E. Ferrero, et al. (1995). "The platelet endothelial cell adhesion molecule-1 (PECAMI) contributes to endothelial barrier function." *FEBS Lett* 374(3): 323-6.

Fujii, G., J. E. Chang, et al. (1997). "The formation of amphotericin B ion channels in lipid bilayers." *Biochemistry* 36(16): 4959-68.

Fujii, Y., D. Okuda, et al. (2003). "Crystal structure of trimestatin, a disintegrin containing a cell adhesion recognition motif RGD." *J Mol Biol* 332(5): 1115-22.

Gasparini, G., N. Weidner, et al. (1993). "Intratumoral microvessel density and p53 protein: correlation with metastasis in head-and-neck squamous-cell carcinoma." *Int J Cancer* 55(5): 739-44.

Goldstone, D., P. W. Haebel, et al. (2001). "DsbC activation by the N-terminal domain of DsbD." *Proc Natl Acad Sci USA* 98(17): 9551-6.

Golubkov, V., D. Hawes, et al. (2003). "Anti-angiogenic activity of contortrostatin, a disintegrin from *Agkistrodon contortrix contortrix* snake venom." *Angiogenesis* 6(3): 213-24.

Gordon, E. H., M. D. Page, et al. (2000). "*Escherichia coli* DipZ: anatomy of a transmembrane protein disulphide reductase in which three pairs of cysteine residues, one in each of three domains, contribute differentially to function." *Mol Microbiol* 35(6): 1360-74.

Gould, R. J., M. A. Polokoff, et al. (1990). "Disintegrins: a family of integrin inhibitory proteins from viper venoms." *Proc Soc Exp Biol Med* 195(2): 168-71.

Goulding, C. W., M. R. Sawaya, et al. (2002). "Thiol-disulfide exchange in an immunoglobulin-like fold: structure of the N-terminal domain of DsbD." *Biochemistry* 41 (22): 6920-7.

Grauschopf, U., J. R. Winther, et al. (1995). "Why is DsbA such an oxidizing disulfide catalyst?" *Cell* 83 (6): 947-55.

Guddat, L. W., J. C. Bardwell, et al. (1997). "The uncharged surface features surrounding the active site of *Escherichia coli* DsbA are conserved and are implicated in peptide binding." *Protein Sci* 6(6): 1148-56.

Guerdoux-Jamet, P., A. Henaut, et al. (1997). "Using codon usage to predict genes origin: is the *Escherichia coli* outer membrane a patchwork of products from different genomes?" *DNA Res* 4(4): 257-65.

Haebel, P. W., D. Goldstone, et al. (2002). "The disulfide bond isomerase DsbC is activated by an immunoglobulin-fold thiol oxidoreductase: crystal structure of the DsbC-DsbDalpha complex." *Embo J* 21 (18): 4774-84.

Jurado, P., D. Ritz, et al. (2002). "Production of functional single-chain Fv antibodies in the cytoplasm of *Escherichia coli.*" *J Mol Biol* 320(1): 1-10.

Katzen, F. and J. Beckwith (2000). "Transmembrane electron transfer by the membrane protein DsbD occurs via a disulfide bond cascade." *Cell* 103 (5): 769-79.

Katzen, F. and J. Beckwith (2003). "Role and location of the unusual redox-active cysteines in the hydrophobic domain of the transmembrane electron transporter DsbD." *Proc Natl Acad Sci USA* 100 (18): 10471-6.

Kurokawa, Y., H. Yanagi, et al. (2000). "Overexpression of protein disulfide isomerase DsbC stabilizes multiple-disulfide-bonded recombinant protein produced and transported to the periplasm in *Escherichia coli.*" *Appl Environ Microbiol* 66(9): 3960-5.

Kurokawa, Y., H. Yanagi, et al. (2001). "Overproduction of bacterial protein disulfide isomerase (DsbC) and its modulator (DsbD) markedly enhances periplasmic production of human nerve growth factor in *Escherichia coli.*" *J Biol Chem* 276(17): 14393-9.

LaVallie, E. R., E. A. DiBlasio, et al. (1993). "A thioredoxin gene fusion expression system that circumvents inclusion body formation in the *E. coli* cytoplasm." *Biotechnology* (N Y) 11 (2): 187-93.

Levy, R., R. Weiss, et al. (2001). "Production of correctly folded Fab antibody fragment in the cytoplasm of *Escherichia coli* trxB gor mutants via the coexpression of molecular chaperones." *Protein Expr Purif* 23(2): 338-47.

Makrides, S. C. (1996). "Strategies for achieving high-level expression of genes in *Escherichia coli.*" *Microbiol Rev* 60 (3): 512-38.

Markland, F. S., K. Shieh, et al. (2001). "A novel snake venom disintegrin that inhibits human ovarian cancer dissemination and angiogenesis in an orthotopic nude mouse model." *Haemostasis* 31 (3-6): 183-91.

Martin, J. L. (1995). "Thioredoxin—a fold for all reasons." *Structure* 3 (3): 245-50.

Martin, J. L., J. C. Bardwell, et al. (1993). "Crystal structure of the DsbA protein required for disulphide bond formation in vivo." *Nature* 365(6445): 464-8.

Maskos, K., M. Huber-Wunderlich, et al. (2003). "DsbA and DsbC-catalyzed oxidative folding of proteins with complex disulfide bridge patterns in vitro and in vivo." *J Mol Biol* 325(3): 495-513.

McCarthy, A. A., P. W. Haebel, et al. (2000). "Crystal structure of the protein disulfide bond isomerase, DsbC, from *Escherichia coli.*" *Nat Struct Biol* 7(3): 196-9.

McLane, M. A., C. Marcinkiewicz, et al. (1998). "Viper venom disintegrins and related molecules." *Proc Soc Exp Biol Med* 219(2): 109-19.

Missiakas, D., C. Georgopoulos, et al. (1994). "The *Escherichia coli* dsbC (xprA) gene encodes a periplasmic protein involved in disulfide bond formation." *Embo J* 13(8): 2013-20.

Moiseeva, N., S. D. Swenson, et al. (2002). "Purification, crystallization and preliminary X-ray analysis of the disintegrin contortrostatin from *Agkistrodon contortrix contortrix* snake venom." *Acta Crystallogr D Biol Crystallogr* 58 (Pt 12): 2122-4.

Mossner, E., M. Huber-Wunderlich, et al. (1998). "Characterization of *Escherichia coli* thioredoxin variants mimicking the active-sites of other thiol/disulfide oxidoreductases." *Protein Sci* 7(5): 1233-44.

Moura-da-Silva, A. M., A. Linica, et al. (1999). "Jararhagin ECD-containing disintegrin domain: expression in *escherichia coli* and inhibition of the platelet-collagen interaction." *Arch Biochem Biophys* 369(2): 295-301.

Newman, P. J. (1994). "The role of PECAM-1 in vascular cell biology." *Ann N Y Acad Sci* 714: 165-74. Newman, P. J., M. C. Berndt, et al. (1990). "PECAM-1 (CD31) cloning and relation to adhesion molecules of the immunoglobulin gene superfamily." *Science* 247(4947): 1219-22.

Niewiarowski, S., M. A. McLane, et al. (1994). "Disintegrins and other naturally occurring antagonists of platelet fibrinogen receptors." *Semin Hematol* 31 (4): 289-300.

Pileri, S. A., G. Roncador, et al. (1997). "Antigen retrieval techniques in immunohistochemistry: comparison of different methods." *J Pathol* 183(1): 116-23.

Prinz, W. A., F. Aslund, et al. (1997). "The role of the thioredoxin and glutaredoxin pathways in reducing protein disulfide bonds in the *Escherichia coli* cytoplasm." *J Biol Chem* 272(25): 15661-7.

Raina, S, and D. Missiakas (1997). "Making and breaking disulfide bonds." *Annu Rev Microbiol* 51: 179-202.

Rietsch, A., D. Belin, et al. (1996). "An in vivo pathway for disulfide bond isomerization in *Escherichia coli*." *Proc Natl Acad Sci USA* 93(23): 13048-53.

Savage, B., U. M. Marzec, et al. (1990). "Binding of the snake venom-derived proteins applaggin and echistatin to the arginine-glycine-aspartic acid recognition site(s) on platelet glycoprotein IIb.IIIa complex inhibits receptor function." *J Biol Chem* 265(20): 11766-72.

Scarborough, R. M., J. W. Rose, et al. (1991). "Barbourin. A GPIIb-IIIa-specific integrin antagonist from the venom of Sistrurus m. barbouri." *J Biol Chem* 266(15): 9359-62.

Schmitmeier, S., F. S. Markland, et al. (2000). "Anti-invasive effect of contortrostatin, a snake venom disintegrin, and TNF-alpha on malignant glioma cells." *Anticancer Res* 20 (6B): 4227-33.

Shi, S. R., M. E. Key, et al. (1991). "Antigen retrieval in formalin-fixed, paraffin-embedded tissues: an enhancement method for immunohistochemical staining based on microwave oven heating of tissue sections." *J Histochem Cytochem* 39(6): 741-8.

Smith, P. K., R. I. Krohn, et al. (1985). "Measurement of protein using bicinchoninic acid." *Anal Biochem* 150(1): 76-85.

Stewart, E. J., F. Aslund, et al. (1998). "Disulfide bond formation in the *Escherichia coli* cytoplasm: an in vivo role reversal for the thioredoxins." *Embo J* 17(19): 5543-50.

Studier, F. W. (1991). "Use of bacteriophage T7 lysozyme to improve an inducible T7 expression system." *J Mol Biol* 219(1): 37-44.

Studier, F. W., A. H. Rosenberg, et al. (1990). "Use of T7 RNA polymerase to direct expression of cloned genes." *Methods Enzymol* 185: 60-89.

Swenson, S., F. Costa, et al. (2004). "Intravenous liposomal delivery of the snake venom disintegrin contortrostatin limits breast cancer progression." *Mol Cancer Ther* 3(4): 499-511.

Trikha, M., Y. A. De Clerck, et al. (1994). "Contortrostatin, a snake venom disintegrin, inhibits beta 1 integrin-mediated human metastatic melanoma cell adhesion and blocks experimental metastasis." *Cancer Res* 54(18): 4993-8.

Trikha, M., W. E. Rote, et al. (1994). "Purification and characterization of platelet aggregation inhibitors from snake venoms." *Thromb Res* 73(1): 39-52.

Venturi, M., C. Seifert, et al. (2002). "High level production of functional antibody Fab fragments in an oxidizing bacterial cytoplasm." *J Mol Biol* 315(1): 1-8.

Walker, K. W. and H. F. Gilbert (1994). "Effect of redox environment on the in vitro and in vivo folding of RTEM-1 beta-lactamase and *Escherichia coli* alkaline phosphatase." *J Biol Chem* 269(45): 28487-93.

Wang, Y., L. Jing, et al. (2002). "A unique approach for high level expression and production of a recombinant cobra neurotoxin in *Escherichia coli*." *J Biotechnol* 94 (3): 235-44.

Weidner, N., J. Folkman, et al. (1992). "Tumor angiogenesis: a new significant and independent prognostic indicator in early-stage breast carcinoma." *J Natl Cancer Inst* 84(24): 1875-87.

Wierzbicka-Patynowski, I., S, Niewiarowski, et al. (1999). "Structural requirements of echistatin for the recognition of alpha(v)beta(3) and alpha(5)beta(1) integrins." *J Biol Chem* 274(53): 37809-14.

Zapun, A., J. C. Bardwell, et al. (1993). "The reactive and destabilizing disulfide bond of DsbA, a protein required for protein disulfide bond formation in vivo." *Biochemistry* 32(19): 5083-92.

Zapun, A., D. Missiakas, et al. (1995). "Structural and functional characterization of DsbC, a protein involved in disulfide bond formation in *Escherichia coli*." *Biochemistry* 34(15): 5075-89.

Zhang, S. P., G. Zubay, et al. (1991). "Low-usage codons in *Escherichia coli*, yeast, fruit fly and primates." *Gene* 105 (1): 61-72.

Zhou, Q., P. Hu, et al. (2000). "Molecular cloning and functional expression of contortrostatin, a homodimeric disintegrin from southern copperhead snake venom." *Arch Biochem Biophys* 375(2): 278-88.

Zhou, Q., M. T. Nakada, et al. (1999). "Contortrostatin, a dimeric disintegrin from *Agkistrodon contortrix contortrix*, inhibits angiogenesis." *Angiogenesis* 3(3): 259-69.

Zhou, Q., M. T. Nakada, et al. (2000). "Contortrostatin, a homodimeric disintegrin, binds to integrin alphavbetaα5." *Biochem Biophys Res Commun* 267(1): 350-5.

Zhou, Q., R. P. Sherwin, et al. (2000). "Contortrostatin, a dimeric disintegrin from *Agkistrodon contortrix contortrix*, inhibits breast cancer progression." *Breast Cancer Res Treat* 61 (3): 249-60.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

The invention claimed is:

1. A method of inhibiting binding between a cell expressing integrin receptors specific for one or more integrins selected from the group consisting of αIIbβ3, αvβ3, αvβ5, or α5β1, said method comprising contacting the cell with a peptide, which comprises the amino acid sequence as set forth in SEQ ID NO: 5.

2. The method of claim 1 wherein said integrin receptor is specific for the αvβ3 integrin.

3. The method of claim 1, wherein said inhibiting, inhibits or decreases tumor metastasis and neovascularization in a cancer patient suffering from melanoma, carcinoma, or sarcoma.

4. The method of claim 1, further comprising administering an effective amount of at least one thrombolytic agent to lyse thrombi.

5. The method of claim 4, wherein said thrombolytic agent is selected from the group consisting of anisoylated plasminogen streptokinase activator complex (APSAC), tissue-type plasminogen activator (tPA), urokinase-type plasminogen activator (uPA); and fibrolase.

* * * * *